US011434330B2

(12) United States Patent
Thompson et al.

(10) Patent No.: US 11,434,330 B2
(45) Date of Patent: *Sep. 6, 2022

(54) POLYROTAXANES BEARING MIXED CYCLODEXTRIN SPECIES AND USES THEREOF

(71) Applicant: Purdue Research Foundation, West Lafayette, IN (US)

(72) Inventors: David H. Thompson, West Lafayette, IN (US); Seok-Hee Hyun, West Lafayette, IN (US); Yawo Mondjinou, West Lafayette, IN (US); Christopher Collins, West Lafayette, IN (US)

(73) Assignee: Purdue Research Foundation, West Lafayette, IN (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/768,365

(22) PCT Filed: Oct. 14, 2016

(86) PCT No.: PCT/US2016/057202
§ 371 (c)(1),
(2) Date: Apr. 13, 2018

(87) PCT Pub. No.: WO2017/066689
PCT Pub. Date: Apr. 20, 2017

(65) Prior Publication Data
US 2021/0040270 A1 Feb. 11, 2021

Related U.S. Application Data

(60) Provisional application No. 62/241,413, filed on Oct. 14, 2015.

(51) Int. Cl.
C08G 83/00 (2006.01)
A61K 31/724 (2006.01)
A61K 51/06 (2006.01)
C08K 5/053 (2006.01)
C08K 5/17 (2006.01)
C08L 5/16 (2006.01)
A61P 43/00 (2006.01)

(52) U.S. Cl.
CPC .......... *C08G 83/007* (2013.01); *A61K 31/724* (2013.01); *A61K 51/06* (2013.01); *C08K 5/053* (2013.01); *C08K 5/17* (2013.01); *C08L 5/16* (2013.01); *A61P 43/00* (2018.01)

(58) Field of Classification Search
CPC combination set(s) only.
See application file for complete search history.

(56) References Cited

FOREIGN PATENT DOCUMENTS

JP 2018-532036 A 11/2018
WO WO-2014182804 A1 11/2014
WO WO-2017066689 A1 4/2017

OTHER PUBLICATIONS

Collins et al. "Synthesis, Characterization, and Evaluation of Pluronic-Based β-Cyclodextrin Polyrotaxanes for Mobilization of Accumulated Cholesterol from Niemann-Pick Type C Fibroblasts", Biochemistry 2013, 52, 3242-3253 (Year: 2013).*
Ramerez et al. "Quantitative role of LAL, NPC2, and NPC1 in lysosomal cholesterol processing defined by genetic and pharmacological manipulations", Journal of Lipid Research vol. 52, 2011, pp. 688-698 (Year: 2011).*
Zhou "Gd3+-1,4,7,10-Tetraazacyclododecane-1,4,7-triacetic-2-hydroxypropyl-β-cyclodextrin/Pluronic Polyrotaxane as a Long Circulating High Relaxivity MRI Contrast Agent", ACS Appl. Mater. Interfaces 2015, 7, 22272-22276 (Year: 2015).*
Zhao et al. "Organogel Formation by a Cholesterol-Stoppered Bistable [2]Rotaxane and Its Dumbbell Precursor", J. Am. Chem. Soc. 2008, 130, 6348-6350 (Year: 2008).*
"European Application Serial No. 16856354.2, Extended European Search Report dated Apr. 24, 2019", 8 pgs.
Collins, et al., "Synthesis, Characterization, and Evaluation of Pluronic-Based β-Cyclodextrin Polyrotaxanes for Mobilization of Accumulated Cholesterol from Niemann-Pick Type C Fibroblasts", Biochemistry, vol. 52, (Apr. 5, 2013), 3242-3253.
"European Application Serial No. 16856354.2, Communication pursuant to Rules 161(2) and 162 EPC dated May 28, 2018", 3 pgs.
"European Application Serial No. 16856354.2, Response filed Nov. 26, 2018 to Communication pursuant to Rules 161(2) and 162 EPC dated May 28, 2018", 7 pgs.
"International Application Serial No. PCT/US2016/057202, International Preliminary Report on Patentability dated Apr. 26, 2018", 7 pgs.
"International Application Serial No. PCT/US2016/057202, International Search Report dated Jan. 12, 2017", 2 pgs.
"International Application Serial No. PCT/US2016/057202, Written Opinion dated Jan. 12, 2017", 5 pgs.
Liu, et al., "Therapeutic potential of cyclodextrins in the treatment of Niemann?Pick type C disease", Clin Lipidol. vol. 7(3), 289-301, (2012), 289-301.
Tamura, et al., "Lysosomal-specific Cholesterol Reduction by Biocleavable Polyrotaxanes for Ameliorating Niemann-Pick Type C Disease", Scientific Reports, vol. 4, 4356, (2014), 8 pgs.
Tamura, et al., "Polyrotaxanes Ameliorate Impaired Autophagy In NPC Disease", JBC, vol. 290 (15), (2015), 9442-9454 pgs.
"European Application Serial No. 16856354.2, Response filed Nov. 11, 2019 to Extended European Search Report dated Apr. 24, 2019", 12 pgs.

(Continued)

Primary Examiner — James W Rogers
(74) Attorney, Agent, or Firm — Schwegman Lundberg & Woessner, P.A.

(57) ABSTRACT

Various embodiments of the present invention are directed to polyrotaxanes comprising a poloxamer core and at least one cyclodextrin and methods for treating Niemann-Pick type C (NPC) and imaging (e.g., MRI) using the polyrotaxanes of the various embodiments of the present invention.

12 Claims, 9 Drawing Sheets

(56) References Cited

OTHER PUBLICATIONS

"Japanese Application Serial No. 2018-539241, Voluntary Amendment filed Oct. 9, 2019", w/English Claims, 10 pgs.
"European Application Serial No. 16856354.2, Communication Pursuant to Article 94(3) EPC dated Jun. 15, 2020", 3 pgs.
"Japanese Application Serial No. 2018-539241, Notification of Reasons for Rejection dated Jul. 6, 2020", (w/ English Translation), 11 pgs.
Mondjinou, Y. A., et al., "Synthesis of 2-Hydroxypropyl-β-cyclodextrin/ Pluronic-Based Polyrotaxanes via Heterogeneous Reaction as Potential Niemann-Pick Type C Therapeutics", *Biomacromolecules*, 14(12), (Dec. 9, 2013), 4189-4197.
"Canadian Application Serial No. 3,002,168, Office Action dated Jun. 10, 2021", 4 pgs.
"European Application Serial No. 16856354.2, Response filed Oct. 23, 2020 to Communication Pursuant to Article 94(3) EPC dated Jun. 15, 2020", 74 pgs.
"Japanese Application Serial No. 2018-539241, Response filed Jan. 6, 2021 to Notification of Reasons for Rejection dated Jul. 6, 2020", w/ English translation, 26 pgs.
"Canadian Application Serial No. 3,002,168, Response filed Oct. 5, 2021 to Office Action dated Jun. 10, 2021", 181 pgs.

\* cited by examiner

POLYROTAXANES BEARING MIXED CYCLODEXTRIN SPECIES AND USES THEREOF

CROSS-REFERENCE TO RELATED APPLICATIONS

This application is the U.S. National Stage Filing under 35 U.S.C. § 371 of International Application No. PCT/US2016/057202, filed on Oct. 14, 2016, and published as WO 2017/066689 A1 on Apr. 20, 2017, which claims the benefit of U.S. Provisional Appl. Ser. No. 62/241,413, filed Oct. 14, 2015, the entirety of which are incorporated by reference as if fully set forth herein.

STATEMENT OF GOVERNMENT SUPPORT

This invention was made with government support under grant TR001108 awarded by the National Institutes of Health. The government has certain rights in the invention.

BACKGROUND OF THE INVENTION

Therapeutic agents and imaging contrast agents sometimes suffer drawbacks stemming from high clearance and/or high toxicity. For example, even though some studies have shown that β-cyclodextrin (β-CD) and its derivatives, including hydroxypropyl-β-cyclodextrin (HP-β-CD), may be useful in the treatment of the typically fatal disease Niemann-Pick type C (NPC), high dosages of the administered β-CDs or derivatives thereof are required since their persistence in the bloodstream is brief (>90% is cleared within 24 hours). With regard to imaging contrast agents, a majority of clinically used contrast agents, though they may have high paramagnetism, excellent relaxation enhancement, and stability, they suffer from rapid clearance from the body, such that they are ineffective, e.g., for angiographic enhancement. In some instances, nanoparticulate platforms used as carriers of, e.g., $Gd^{3+}$, though they have better pharmacokinetics than other clinically used contrast agents, suffer from issues such as acute toxicity and poor water accessibility. There is therefore a need in the art for therapeutic agents for treating, e.g., NPC, and imaging contrast agents that do not suffer from the drawbacks enumerated herein.

BRIEF DESCRIPTION OF THE FIGURES

The figures illustrate generally, by way of example, but not by way of limitation, various embodiments discussed in the present document.

DETAILED DESCRIPTION OF THE INVENTION

Figure 1:
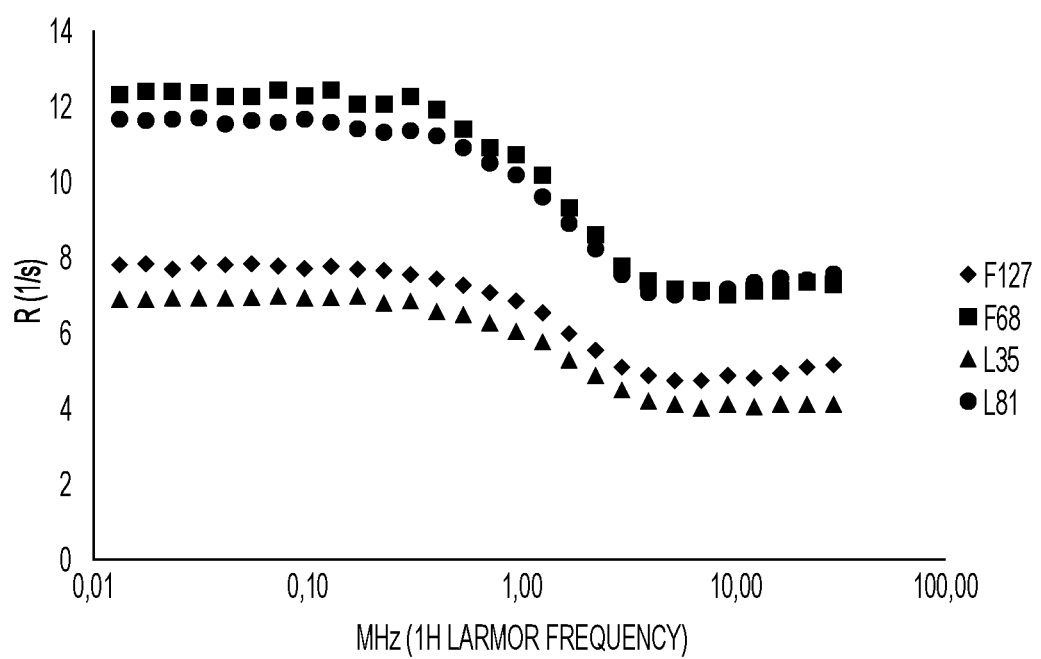
FIG. 1 is a $^1$H NMRD spectra of $Gd^{3+}$—HP-β-CD/SBE-β-CD based polyrotaxanes, where $PR_1$, $PR_2$, $PR_3$, and $PR_5$ correspond to the polyrotaxane prepared with F127, F68, L35, L81 Pluronic® copolymers.

Reference will now be made in detail to certain embodiments of the disclosed subject matter, examples of which are illustrated in part in the accompanying drawings. While the disclosed subject matter will be described in conjunction with the enumerated claims, it will be understood that the exemplified subject matter is not intended to limit the claims to the disclosed subject matter.

The therapeutic agents and imaging contrast agents of the various embodiments of the present invention are based on a class of supramolecular materials known as polyrotaxanes having one or more macrocylic hosts "threaded" onto the "axle" of the polyrotaxane, as shown in Scheme 1 below. It has been unexpectedly found that as the number of macrocyclic hosts present in the polyrotaxanes described herein increases, the dose of polyrotaxane that one needs to use to achieve therapeutic efficacy or for imaging purposes decreases, in some cases significantly. While not wishing to be bound by any specific theory, it is believed that as the number of macrycyclic hosts increases, the more "rod-like" the polyrotaxanes of the various embodiments described herein become and, as a result, one observes significant improvements in the concentration-dependent molar relaxivity of the polyrotaxanes. Improvements in the concentration-dependent molar relaxivity leads to, in some embodiments, polyrotaxanes that are significantly improved imaging agents that are able to enhance contrast, thereby giving greater discrimination in anatomy.

A polyrotaxane is a macrocylic host molecule or molecules that is/are "threaded" onto a polymer chain of compatible dimensions via host-guest hydrophobic interactions, with the ends of the polymer chain being capped with endcapping groups. A schematic representation of a polyrotaxane is given in Scheme 1:

Scheme 1

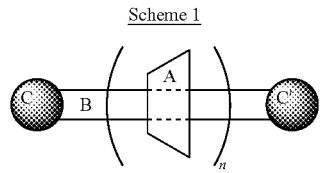

or a salt thereof (e.g., a pharmaceutically acceptable salt thereof), wherein C and C' are the same or different and represent endcapping groups; B represents the "polymer chain of compatible dimensions" to which the endcapping groups are covalently attached; A represents the macrocyclic host molecule that is "threaded" onto the polymer chain B; and n is an integer from 1 to 100 (e.g., 1 to 75, 1 to 50, 1 to 30, 5 to 15, 5 to 12, 10 to 30, 10 to 50, 1 to 20, 1 to 15, 5 to 15, 3 to 11, 1 to 12, 2 to 12 or 2 to 18), wherein n represents the number of macrocyclic host molecules A that are "threaded" onto the polymer chain B.

In some embodiments, all of the macrocyclic host molecules A are the same. In other embodiments, one or more of the macrocyclic host molecules A are different. A schematic representation of a polyrotaxane where one or more of the macrocyclic host molecules A are different is shown in Schemes IA and IB:

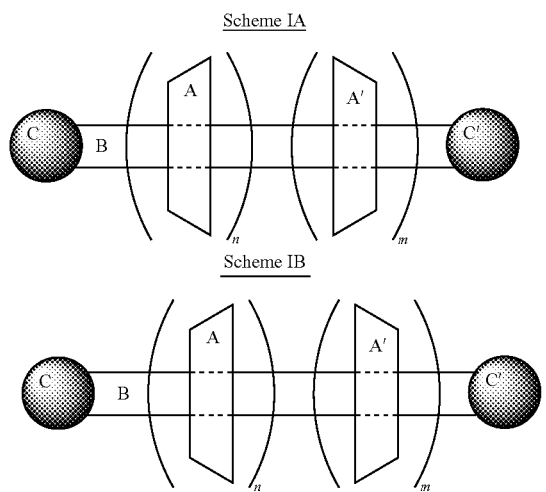

Scheme IA

Scheme IB wherein m and n can be the same or different; n is an integer from 0 to 100 (e.g., 1 to 75, 1 to 50, 0 to 30, 1 to 30, 5 to 15, 5 to 12, 10 to 30, 10 to 50, 1 to 20, 1 to 15, 5 to 15, 3 to 11, 1 to 12, 2 to 12 or 2 to 18); m is an integer from 0 to 100 (e.g., 1 to 75, 1 to 50, 0 to 30, 1 to 30, 5 to 15, 5 to 12, 10 to 30, 10 to 50, 1 to 20, 1 to 15, 5 to 15, 3 to 11, 1 to 12, 2 to 12 or 2 to 18); and wherein m and n represent the number of macrocyclic host molecules A' and A, respectively, that are "threaded" onto the polymer chain B. It is clear, therefore, that when the macrocyclic host molecules are different, they can be present in varying molar ratios determined by the ratio of n to m. In some embodiments, the ratio can be between 1:0 to 0:1, including 1:1. Although two specific orientations of A and A' are given in Schemes IA and IB, it should be understood that A and A' can be in all possible orientations including the orientation shown in Scheme IC, wherein each m and n can be the same or different:

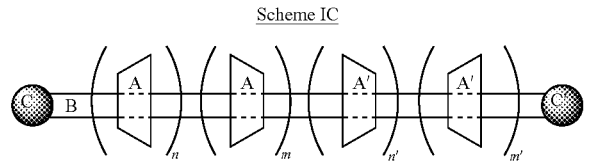

Scheme IC wherein m, m', n, and n' can be the same or different; m is an integer from 0 to 100 (e.g., 1 to 75, 1 to 50, 0 to 30, 1 to 30, 5 to 15, 5 to 12, 10 to 30, 10 to 50, 1 to 20, 1 to 15, 5 to 15, 3 to 11, 1 to 12, 2 to 12 or 2 to 18); n is an integer from 0 to 100 (e.g., 1 to 75, 1 to 50, 0 to 30, 1 to 30, 5 to 15, 5 to 12, 10 to 30, 10 to 50, 1 to 20, 1 to 15, 5 to 15, 3 to 11, 1 to 12, 2 to 12 or 2 to 18); m' is an integer from 0 to 100 (e.g., 1 to 75, 1 to 50, 0 to 30, 1 to 30, 5 to 15, 5 to 12, 10 to 30, 10 to 50, 1 to 20, 1 to 15, 5 to 15, 3 to 11, 1 to 12, 2 to 12 or 2 to 18); and n' is an integer from 0 to 100 (e.g., 1 to 75, 1 to 50, 0 to 30, 1 to 30, 5 to 15, 5 to 12, 10 to 30, 10 to 50, 1 to 20, 1 to 15, 5 to 15, 3 to 11, 1 to 12, 2 to 12 or 2 to 18).

In some embodiments, the orientation of the macrocyclic host molecules (A) and (A') can be as shown in Scheme IC, herein, where m, m', n, and n' are non-zero and about 85% (e.g. from about 65% to about 90%; about 75% to about 90%; or about 80% to about 90%) of the macrocyclic host molecules have the "tail-to-tail" orientation of $(A)_n$ and $(A)_m$ and about 15% (e.g., about 10% to about 35%; about 10% to about 25%; or about 10% to about 20%) of the macrocyclic host molecules have the "head-to-head" orientation of $(A')_{n'}$ and $(A')_{m'}$.

The macrocyclic host molecule (A) and (A)' can be any suitable macrocyclic host molecule, so long as the macrocylic host molecule or molecules can "thread" onto a polymer chain of compatible dimensions via host-guest hydrophobic interactions. For suitable macrocyclic host molecules, see, e.g., C. J. Collins et al., *Biochemistry* 52: 3242-3253 (2013), which is incorporated by reference as if fully set forth herein. In some embodiments, the macrocyclic host molecule (A) and (A') can be a cyclodextrin. As used herein, the term "cyclodextrin" broadly refers to macrocyclic oligosaccharides produced by the cyclization (e.g., enzymatic cyclization) of 6, 7, or 8 (+)-glucopyranoside units linked by, e.g., α-1,4-bonds to generate α-, β-, or γ-CD, respectively.

Cyclodextrins have a toroidal topology with a hydrophobic internal cavity. β-CD, and its derivatives, have garnered attention due to their use in the pharmaceutical and food industry as solubilizing agents, permeability enhancers, and active ingredient stabilizers.

In some embodiments, the macrocyclic host molecule (A) and (A') has the general formula (I) or (Ia):

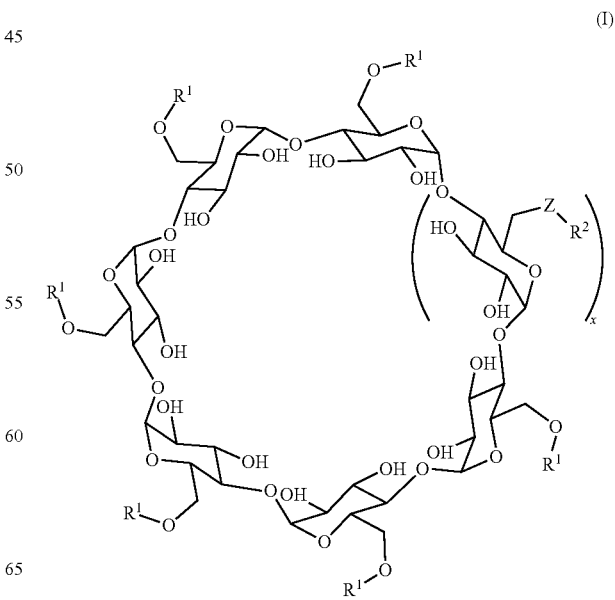

(I)

(Ia)

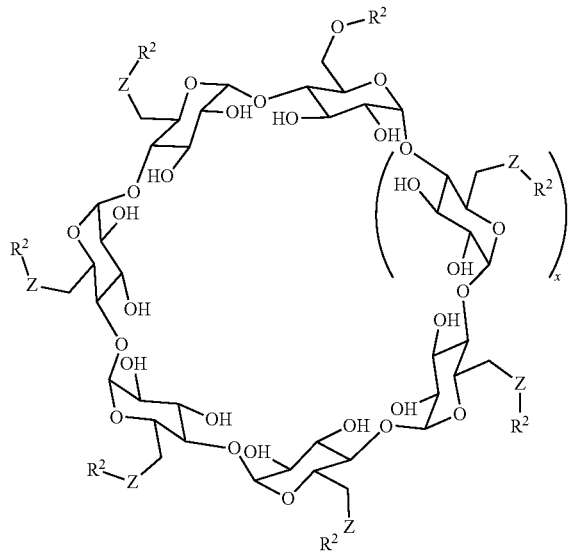

wherein each Z is independently O (oxygen), NH, or an azido group ($-N_3$ or $-N=N^+=N^-$); each $R^1$ and $R^2$ is independently hydrogen or a substituted or unsubstituted $(C_1-C_{20})$hydrocarbyl group (e.g., substituted or unsubstituted $(C_1-C_{12})$hydrocarbyl group; substituted or unsubstituted $(C_1-C_6)$hydrocarbyl group; or a substituted or unsubstituted $(C_1-C_3)$hydrocarbyl group), interrupted by 0 to 20 (e.g., 0-5 or 0-3) groups chosen from —O—, —NH—, and —S—; and x is an integer from 0 to 8 (e.g., 0-3, 1-8 and 1-3; in some embodiments x can be 0). It should be understood that when Z is an azido ($-N_3$) group, $R^2$ is absent. In some embodiments, each $R^1$ and $R^2$ is independently hydrogen or a $(C_1-C_{20})$hydrocarbyl group substituted with a drug radical, any suitable reporter group radical (e.g., an imaging contrast agent radical such as a radionuclide chelating moiety comprising a radionuclide or a paramagnetic nuclide chelating moiety comprising a paramagnetic nuclide; examples of chelating moieties include DOTA and DO3A radicals) or combinations thereof. In circumstances where x is 1, Z is an azido ($-N_3$) group, each $R^1$ is hydrogen, and $R^2$ is absent, the macrocyclic host molecule (A) or (A') is known as azido-β-cyclodextrin.

In other embodiments, wherein each Z is independently O (oxygen), NH, or an azido group ($-N_3$ or $-N=N^+=N^-$); each $R^1$ and $R^2$ is independently hydrogen or a substituted or unsubstituted $(C_1-C_{20})$hydrocarbyl group (e.g., substituted or unsubstituted $(C_1-C_{12})$hydrocarbyl group; substituted or unsubstituted $(C_1-C_6)$hydrocarbyl group; or a substituted or unsubstituted $(C_1-C_3)$hydrocarbyl group), interrupted by 0 to 5 (e.g., 0-3) groups chosen from —O—, —NH—, and —S—; and x is an integer from 1 to 8 (e.g., 1-3). It should be understood that when Z is an azido ($-N_3$) group, $R^2$ is absent. In some embodiments, each $R^1$ and $R^2$ is independently hydrogen or a $(C_1-C_{20})$hydrocarbyl group substituted with a drug radical, an imaging contrast agent radical (e.g., a radionuclide chelating moiety comprising a radionuclide or a paramagnetic nuclide chelating moiety comprising a paramagnetic nuclide) or combinations thereof. In circumstances where x is 1, Z is an azido ($-N_3$) group, each $R^1$ is hydrogen, and $R^2$ is absent, the macrocyclic host molecule (A) or (A') is known as azido-β-cyclodextrin.

In some embodiments, each $R^1$ is independently a substituted or unsubstituted $(C_1-C_{20})$alkyl group (e.g., substituted or unsubstituted $(C_1-C_{12})$ alkyl group; substituted or unsubstituted $(C_1-C_6)$ alkyl group; or a substituted or unsubstituted $(C_1-C_3)$ alkyl group), interrupted by 0 to 5 (e.g., 0-3) groups chosen from —O—, —NH—, and —S—; and x is an integer from 1 to 3. In some embodiments, each $R^1$ is a substituted $(C_1-C_{20})$alkyl group. In some embodiments, the substituent on the $(C_1-C_{20})$alkyl group is a sulfonate ($-SO_3^-$) group. In still other embodiments, $R^1$ is a butylsulfonate group ($-CH_2CH_2CH_2CH_2SO_3$). The sulfonate ($-SO_3$) and butylsulfonate groups ($-CH_2CH_2CH_2CH_2SO_3$) can be associated with any suitable counterion, including sodium ($Na^+$), potassium ($K^+$), and lithium ($Li^+$) cations. Even though monocations are listed herein, polycations are also contemplated herein, including calcium ($Ca^{2+}$) and magnesium ($Mg^{2+}$) dications.

In some embodiments, in the context of the compounds of the formula (I) wherein each Z is independently O or NH; each $R^1$ is independently hydrogen or a substituted or unsubstituted $(C_1-C_{20})$hydrocarbyl group, interrupted by 0 to 5 groups chosen from —O—, —NH—, and —S—; x is an integer from 1 to 3; and $R^2$ is substituted or unsubstituted $(C_1-C_{20})$hydrocarbyl group, interrupted by 0 to 5 groups chosen from —O—, —NH—, and —S—, with the proviso that at least one $R^2$ is $(C_1-C_{20})$hydrocarbyl group, interrupted by 0 to 5 groups chosen from —O—, —NH—, and —S—, substituted with a group $C(S)N(R)_2$, wherein one R is hydrogen and the other is an aryl group substituted with a radionuclide chelating moiety.

In some embodiments, each $R^1$ is hydrogen or a radical having the formula:

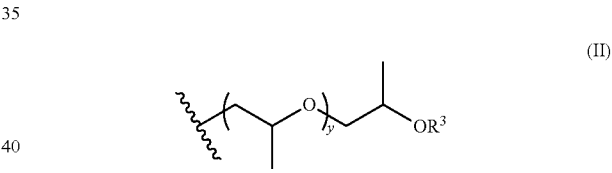

(II)

wherein y is an integer from 0 to 10 (e.g., an integer from 1 to 8, 1 to 5 or 1 to 3) and $R^3$ is hydrogen or a substituted or unsubstituted $(C_1-C_3)$hydrocarbyl group.

In other embodiments $R^1$ and $R^2$ are each, independently, hydrogen or a radical of the formula (II), wherein $R^3$ is hydrogen; Z is O; x is an integer from 1 to 3; and y is an integer from 0 to 3.

In some embodiments, the compound of the formula (I) is hydroxypropyl-β-cyclodextrin (HP-β-CD). HP-β-CD is an attractive precursor for polyrotaxane synthesis, since it is approved by the FDA as an inactive pharmaceutical ingredient and is substantially more water soluble at room temperature (0.65 g/mL in water) than β-CD. Such solubility in aqueous solution makes it a good candidate for designing well-tolerated polyrotaxanes, such as those described herein, that could enhance the pharmacokinetics and biodistribution of HP-β-CD in models of, e.g., NPC disease.

In some embodiments, each $R^1$ is independently hydrogen or a substituted or unsubstituted $(C_1-C_{20})$hydrocarbyl group, interrupted by 0 to 5 (e.g., 0-3) groups chosen from —O—, —NH—, and —S—; Z is —NH—; and $R^2$ is a $(C_1-C_{20})$ hydrocarbyl group, interrupted by 0 to 5 (e.g., 0-3) groups chosen from —O—, —NH—, and —S—, substituted with a group $C(S)N(R)_2$, wherein R is hydrogen or substituted aryl (e.g., aryl substituted with a chelating moiety).

In some embodiments, each $R^1$ is independently hydrogen or a substituted or unsubstituted $(C_1\text{-}C_{20})$hydrocarbyl group, interrupted by 0 to 5 (e.g., 0-3) groups chosen from —O—, —NH—, and —S—; Z is —NH—; $R^2$ is a $(C_1\text{-}C_{20})$hydrocarbyl group, interrupted by 0 to 5 (e.g., 0-3) groups chosen from —O—, —NH—, and —S—, substituted with a group $C(S)N(R)_2$, wherein R is hydrogen or substituted aryl (e.g., aryl substituted with a chelating moiety); and x is 1.

In some embodiments, each $R^1$ is independently hydrogen or a substituted or unsubstituted $(C_1\text{-}C_{20})$hydrocarbyl group, interrupted by 0 to 20 (e.g., 0-5 or 0-3) groups chosen from —O—, —NH—, and —S—; Z is —NH—; $R^2$ is a $(C_1\text{-}C_{20})$ hydrocarbyl group, interrupted by 0 to 20 (e.g., 0-3) groups chosen from —O—, —NH—, and —S—, substituted with a group $C(S)N(R)_2$, wherein R is hydrogen or substituted aryl (e.g., aryl substituted with a chelating moiety); and x is 1.

In some embodiments, for compounds of the formula (I) or (Ia), each $R^2$ is independently hydrogen or a substituted or unsubstituted $(C_1\text{-}C_{20})$hydrocarbyl group, interrupted by 0 to 20 (e.g., 0-5 or 0-3) groups chosen from —O—, —NH—, and —S—; Z is —NH—, substituted with a group $C(S)N(R)_2$, wherein R is hydrogen or substituted aryl (e.g., aryl substituted with a chelating moiety); and x is 1.

In other embodiments, each $R^1$ is hydrogen; $R^2$ is a substituted or unsubstituted $(C_1\text{-}C_{20})$hydrocarbyl group, interrupted by 0 to 5 (e.g., 0-3) groups chosen from —O—, —NH—, and —S—; Z is —NH—; and x is 1. In still other embodiments, each $R^1$ is hydrogen; Z is —NH—; x is 1; $R^2$ is a $(C_1\text{-}C_{20})$hydrocarbyl group, interrupted by 0 to 5 (e.g., 0-3) groups chosen from —O—, —NH—, and —S—, substituted with a group $C(S)N(R)_2$, wherein R is hydrogen or substituted aryl (e.g., aryl substituted with a chelating moiety). A non-limiting example of such an $R^2$ group is one having the formula (III):

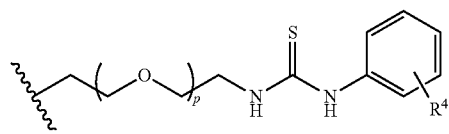

(III)

wherein p is an integer from 1 to 10 (e.g., 1 to 5 or 1 to 3); and $R^4$ is a chelating moiety (e.g., a 1,4,7,10-tetraazacyclododecane-1,4,7,10-tetraacetic acid (DOTA) radical). In some embodiments, the group having the formula (III) is a group of the formula (IIIa):

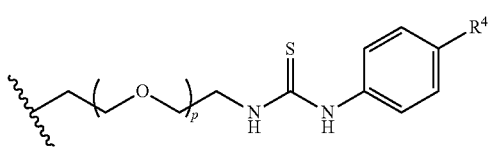

(IIIa)

wherein p is an integer from 1 to 10 (e.g., 1 to 5 or 1 to 3); and $R^4$ is a chelating moiety (e.g., a DOTA radical).

In other embodiments, in compounds of the formula (I) or (Ia), $R^2$ has the formula (IIb):

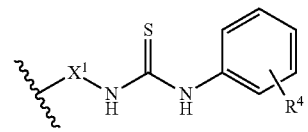

(IIIb)

wherein $X^1$ represents a suitable linker, including a short-chain polypeptide (e.g., a polypeptide having up to 20 amino acids or from about 5 to about 20 amino acids), a short-chain carbohydrate (e.g., a carbohydrate having up to 20 saccharide units or from about 5 to about 20 saccharide units), a polyester or a polyamide; and $R^4$ is a chelating moiety (e.g., a 1,4,7,10-tetraazacyclododecane-1,4,7,10-tetraacetic acid (DOTA) radical).

In other embodiments, in compounds of the formula (I) or (Ia), $R^2$ has the formula (IIIc):

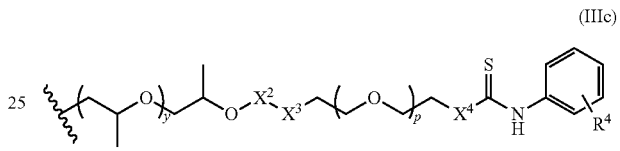

(IIIc)

wherein y is an integer from 0 to 10; p is an integer from 1 to 10; $X^2$ represents a suitable linker, including a $(C_1\text{-}C_6)$ acyl (e.g., C=O), a short-chain polypeptide (e.g., a polypeptide having up to 20 amino acids or from about 5 to about 20 amino acids), a short-chain carbohydrate (e.g., a carbohydrate having up to 20 saccharide units or from about 5 to about 20 saccharide units), a polyester or a polyamide; $X^3$ and $X^4$ are each, independently, —O—, —NH—, a carbamyl group (e.g., —OC(O)N(R)—, wherein R is defined herein), a heterocyclyl group, —S—S—, an ester (e.g., —C(O)O—), or an amide (C(O)N(R), wherein R is defined herein); and $R^4$ is a chelating moiety (e.g., a 1,4,7,10-tetraazacyclododecane-1,4,7,10-tetraacetic acid (DOTA) radical).

In some embodiments, when the macrocyclic host molecule (A) or (A') comprises an $R^2$ group comprising a radical of a chelating moiety (e.g., a DOTA radical), the polyrotaxanes described herein are useful as MRI contrast agents, when the chelating moiety comprises a radionuclide, as the term is defined herein.

The polymer chain (B), sometimes referred to as an "axle" herein, can be any suitable polymer chain, so long as the polymer chain can "thread" through a macrocylic host molecule or molecules and can interact with the polymer chain via host-guest hydrophobic interactions. For suitable polymer chains, see, e.g., C. J. Collins et al., *Biochemistry* 52: 3242-3253 (2013), which is incorporated by reference as if fully set forth herein. In some embodiments, suitable polymer chains "dethread" from the "axle" under certain conditions (e.g., under physiological conditions or in the presence of enzymes, when enzymes enzymatically remove the endcapping groups (C and C'), e.g., in NPC cells), such that the macrocyclic host molecule is released. The polymer chain (B) is a polymer chain of compatible dimensions. Suitable polymer chains (B) include, but are not limited to, those based on amine-terminated poly (tetrahydrofuran) and amine-terminated poly (ethylene glycol). See, e.g., Nakazono, K., et al., *Macromolecules* 43: 691-696 (2009), which is incorporated by reference as if fully set forth herein. Other suitable polymer chains (B) include carbohydrates, polypeptides, polycarbonate, polyamide, and polyester polymers. The polymer chain (B) can be attached (e.g., covalently) to the endcapping groups C and C' by any suitable linking group, including a carbamyl group, a heterocyclyl group (e.g., a 1,2,3-triazolyl group), disulfide, amide, ester or the like.

Suitable polymer chains (B) also include, but are not limited to, those based on polyalkylene oxide polymer chains that may be referred to herein, in some instances, as a "poloxamer core." Examples of polyalkylene oxide (e.g., random copolymer, di-block copolymer or tri-block copolymer arrangement) polymer chains (B) include those having the formula (IV):

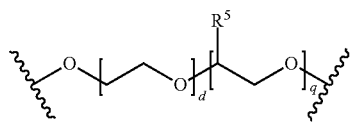

wherein each $R^5$ is independently a substituted or unsubstituted $(C_1-C_{20})$hydrocarbyl group (e.g., substituted or unsubstituted $(C_1-C_{12})$hydrocarbyl group; substituted or unsubstituted $(C_1-C_6)$hydrocarbyl group; or a substituted or unsubstituted $(C_1-C_3)$hydrocarbyl group); d is an integer from about 1 to about 800 (e.g., about 6 to about 200; about 20 to about 200; about 20 to about 150; about 100 to about 500; about 250 to about 750; about 150 to about 400; about 250 to about 600 or about 300 to about 700); and q is an integer from about 6 to about 800 (e.g., about 10 to about 100; about 10 to about 75; about 10 to about 50; about 100 to about 500; about 250 to about 750; about 150 to about 400; about 250 to about 600 or about 300 to about 700).

In some embodiments, each $R^5$ is independently a substituted or unsubstituted $(C_1-C_{20})$alkyl group (e.g., substituted or unsubstituted $(C_1-C_{12})$ alkyl group; substituted or unsubstituted $(C_1-C_6)$ alkyl group; or a substituted or unsubstituted $(C_1-C_3)$ alkyl group). In some embodiments, $R^5$ is methyl.

In some embodiments, d+q is from about 10 to about 800 (e.g., about 100 to about 500; about 250 to about 750; about 150 to about 400; about 250 to about 600 or about 300 to about 700). In other embodiments, d+q are such that the molecular weight of the polyalkylene oxide polymer chain (B) is from about 2 kD to about 50 kD (e.g., about 10 kD to about 35 kD, about 10 kD to about 20 kD, about 15 kD to about 25 kD or about 15 kD to about 30 kD).

Examples of polyalkylene oxide polymer chains (B) include polyalkylene oxide polymer chains based on poloxamers such as the PLURONIC® surfactants, a family of poly(ethylene glycol)-poly(propylene glycol)-poly(ethylene glycol) (PEG-PPG-PEG) triblock copolymers. PLURONIC® surfactants themselves, enjoy a wide range of applications due to their favorable biocompatibility and low toxicity. Examples of PLURONIC® surfactants include, but are not limited to PLURONIC® F127; PLURONIC® F68; PLURONIC® L35; PLURONIC® L64; and PLURONIC® L81.

The groups C and C' are the same or different and represent any suitable endcapping groups. For suitable endcapping groups, see, e.g., C. J. Collins et al., *Biochemistry* 52: 3242-3253 (2013), which is incorporated by reference as if fully set forth herein. The endcapping groups function generally to prevent the macrocyclic host molecule (A) or (A') from "dethreading" from the polymer chain (B) by, e.g., providing sufficient steric bulk. In some embodiments, the endcapping groups prevent the macrocyclic host molecule (A) or (A') from "dethreading" from the polymer chain (B) until an appropriate "trigger" is applied that removes the endcapping groups (e.g., under physiological conditions or in the presence of enzymes, when enzymes enzymatically remove the endcapping groups (C and C'), e.g., in NPC cells).

The groups C and C' are covalently attached to the polymer chain via a suitable linking group. Suitable endcapping groups include, but are not limited to, groups of the formula (IV):

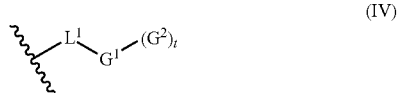

wherein $L^1$ is a $(C_1-C_6)$hydrocarbylene group; $G^1$ is a substituted or unsubstituted $(C_1-C_6)$hydrocarbylene group, interrupted by 0 to 5 (e.g., 0-3) groups chosen from —O—, —NH—, and —S—; $G^2$ is substituted or unsubstituted $(C_0-C_6)$hydrocarbylene-$(C_6-C_{50})$hydrocarbyl group (e.g., substituted or unsubstituted $(C_1-C_6)$hydrocarbylene-$(C_6-C_{50})$hydrocarbyl group), interrupted by 0 to 5 (e.g., 0-3) groups chosen from —O—, —NH—, and —S—, wherein the $(C_5-C_{50})$hydrocarbyl group is sterically bulky; and t is an integer from 2 to 5 (e.g., 2). In some embodiments, the $(C_6-C_{50})$hydrocarbyl group (e.g., $(C_6-C_{30})$hydrocarbyl; $(C_6-C_{20})$hydrocarbyl or $(C_5-C_{15})$hydrocarbyl) can be substituted or unsubstituted and can be, for example, a fluorescent moiety (e.g., fluorescein or a fluoresceinyl radical), a steroid (e.g., cholesterol or a cholesteryl radical), a short-chain polypeptide, a short-chain carbohydrate or an aryl group (e.g., a substituted aryl group).

In other embodiments, $L^1$ is a $(C_1-C_6)$hydrocarbylene group; $G^1$ is a substituted or unsubstituted $(C_1-C_5)$hydrocarbylene group, interrupted by 0 to 5 (e.g., 0-3) —NH— groups; $G^2$ is substituted or unsubstituted $(C_6-C_{50})$hydrocarbylene-$(C_1-C_5)$hydrocarbyl group, interrupted by 0 to 5 (e.g., 0-3) —NH— groups, wherein the $(C_6-C_{50})$hydrocarbyl group is sterically bulky; and t is an integer from 2 to 5 (e.g., 2).

In some embodiments, $L^1$ is a $(C_1-C_3)$hydrocarbylene group; $G^1$ is a substituted or unsubstituted $(C_1-C_3)$hydrocarbylene group, interrupted by 0 to 5 (e.g., 0-3) groups chosen from —O—, —NH—, and —S—; $G^2$ is substituted or unsubstituted $(C_1-C_3)$hydrocarbylene-$(C_6-C_{50})$hydrocarbyl group, interrupted by 0 to 5 (e.g., 0-3) groups chosen from —O—, —NH—, and —S—, wherein the $(C_6-C_{50})$hydrocarbyl group is sterically bulky; and t is an integer from 2 to 5 (e.g., 2).

In still other embodiments, $L^1$ is $(C_1-C_6)$acyl (e.g., C=O); $G^1$ is a substituted or unsubstituted $(C_1-C_3)$hydrocarbylene group, interrupted by 0 to 5 (e.g., 0-3) —NH— groups; $G^2$ is substituted or unsubstituted $(C_1-C_3)$hydrocarbylene-$(C_6-C_{50})$hydrocarbyl group, interrupted by 0 to 5 (e.g., 0-3) —NH— groups, wherein the $(C_6-C_{50})$hydrocarbyl group is sterically bulky; and t is an integer from 2 to 5 (e.g., 2).

In some examples, $G^1$ and $G^2$, together, form a radical having the formula:

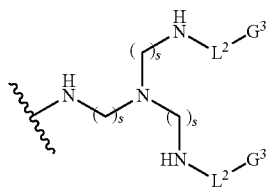

wherein each $L^2$ is independently a bond or $(C_1-C_6)$acyl (e.g., C=O); each $G^3$ is a substituted or unsubstituted $(C_6-C_{50})$hydrocarbyl group, interrupted by 0 to 5 (e.g., 0-3) groups chosen from —O—, —NH—, and —S— (e.g., —O—), wherein the $(C_6-C_{50})$hydrocarbyl group is sterically bulky; and each s is independently an integer from 1 to 6 (e.g., 2 to 5 or 2 to 3).

In other examples, $G^1$ and $G^2$, together, form a radical having the formula:

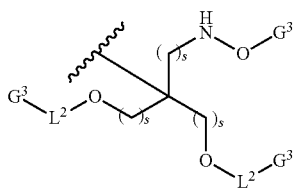

wherein each $L^2$ is independently a bond or $(C_1-C_6)$acyl (e.g., C=O); each $G^3$ is a substituted or unsubstituted $(C_6-C_{50})$hydrocarbyl group, interrupted by 0 to 5 (e.g., 0-3) groups chosen from —O—, —NH—, and —S— (e.g., —O—), wherein the $(C_6-C_{50})$hydrocarbyl group is sterically bulky; and each s is independently an integer from 1 to 6 (e.g., 2 to 5 or 2 to 3).

In some embodiments, the group $G^3$ is a substituted or unsubstituted —O—$(C_6-C_{50})$alkyl group or a substituted or unsubstituted $(C_6-C_{12})$aryl group, wherein the $(C_6-C_{50})$alkyl group and the $(C_5-C_{12})$aryl group are sterically bulky. In other embodiments, the group $G^3$ is a substituted or unsubstituted —O—$(C_6-C_{50})$alkyl group, wherein, in some examples, the $(C_6-C_{50})$alkyl group is a cholesteryl group:

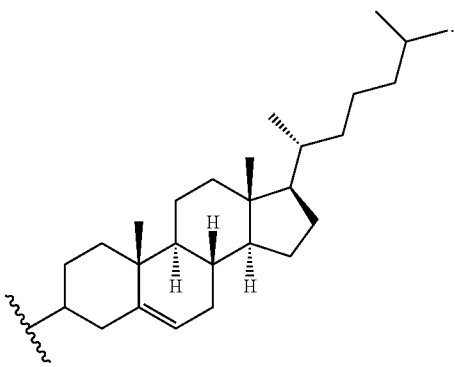

In other embodiments, $G^3$ is a substituted phenyl group, wherein the phenyl group is substituted with at least two substituents (e.g., $NO_2$). In some embodiments, the substituted phenyl group is a trisubstituted phenyl group such as a 2,4,6-trinitro phenyl group:

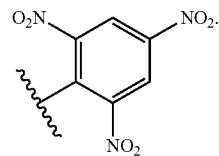 [SMILES: *c1c([N+](=O)[O-])cc([N+](=O)[O-])cc1[N+](=O)[O-]]

In still other embodiments, the group $G^3$ is a peptide or carbohydrate having sufficient steric bulk to prevent the macrocyclic host molecule (A) or (A') from "dethreading" from the polymer chain (B). For example, the peptide or carbohydrate, or any of the endcapping groups described herein, have a steric bulk as defined by their effective diameter of from about 2 nm to about 50 nm (e.g., from about 4 nm to about 10 nm; about 2 nm to about 15 nm; or about 3 nm to about 12 nm).

In yet other embodiments, the group $G^3$ can be a fluorescent moiety (e.g., fluorescein or a fluoresceinyl radical), a steroid (e.g., cholesterol or a cholesteryl radical), a short-chain polypeptide, a short-chain carbohydrate, an aryl group (e.g., a substituted aryl group) or a cyclodextrin group, such as an α- or a β-cyclodextrin.

In some embodiments, the polyrotaxanes of the various embodiments of the present invention are compounds of the formula (V), (VI), (VII), (VIII) or combinations thereof:

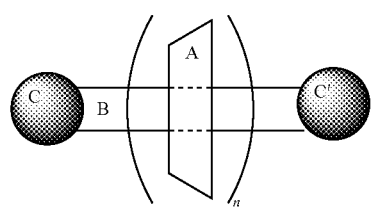

(V)

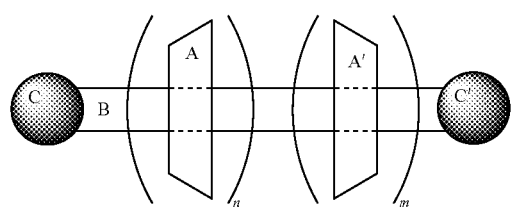

(VI)

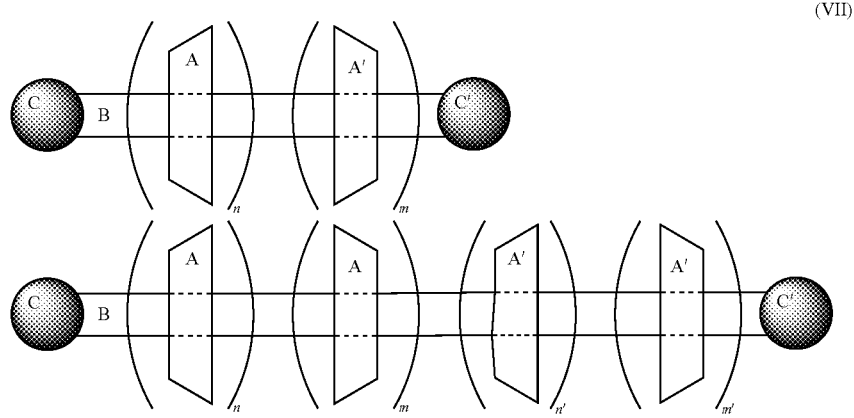

wherein A, A', B, C, C', n, m, n', and m' are as defined herein. In some examples, C and C' are the same or different and comprise a peptide or carbohydrate having sufficient steric bulk to prevent polyrotaxanes A and A' from "dethreading" from the polymer chain (B) or C' and C' are the same or different and comprise groups of the formula:

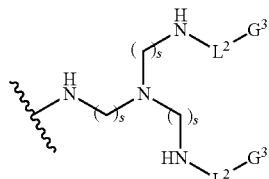

wherein each s is 2, each $L^2$ is a bond or C=O, and each $G^3$ is a cholesteryl group, a 2,4,6-trinitro phenyl group or a peptide or carbohydrate having sufficient steric bulk to prevent the macrocyclic host molecule (A) or (A') from "dethreading" from the polymer chain (B); B represents a "polymer chain of compatible dimensions" of the formula:

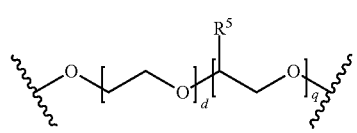

wherein $R^5$ is methyl and d and q are as defined herein, to which the endcapping groups are covalently attached to the polymer chain via any suitable linking group (e.g., $L^1$ herein), including a suitable $(C_1\text{-}C_6)$hydrocarbylene group, such as a $(C_1\text{-}C_6)$acyl group; and A represents the macrocyclic host molecule of the general formula (I) or (Ia):

(I)

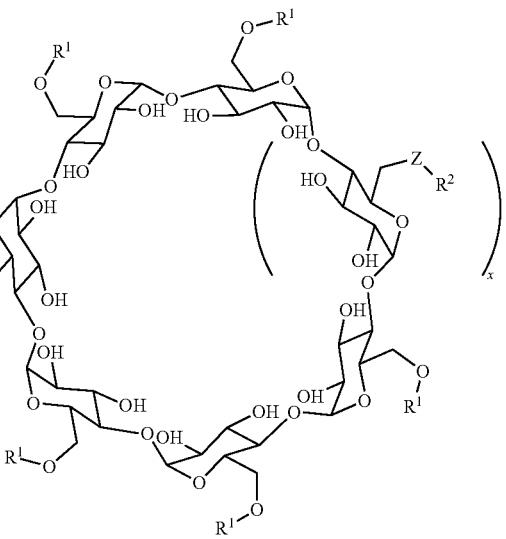

(Ia)

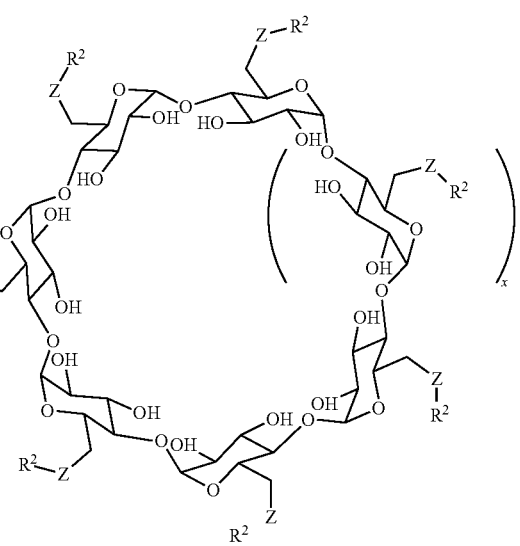

wherein $R^1$, $R^2$, Z, and x are as defined herein, wherein the macrocyclic host molecule is "threaded" onto the polymer chain B; n is an integer from 0 to 30 (e.g., 0 to 20, 0 to 15, 0 to 12, 2 to 12 or 2 to 18); and m is an integer from 0 to 30 (e.g., 0 to 20, 0 to 15, 0 to 12, 2 to 12 or 2 to 18), wherein wherein m and n represent the number of macrocyclic host molecules A' and A, respectively, that are "threaded" onto the polymer chain B. See, e.g., C. J. Collins et al., *Biochemistry* 52: 3242-3253 (2013), which is incorporated by reference as if fully set forth herein.

In some embodiments, the polyrotaxanes of the various embodiments of the present invention are HPβCD/ SBEβCD-F127; HPβCD/SBEβCD-F68; HPβCD/SBEβCD-L35; —HPβCD/SBEβCD-L64; or HPβCD/SBEβCD-L81, wherein the polyrotaxane has a weight average molecular weight of about 20,000 g/mol to about 50,000 g/mol as determined by GPC analysis. In some embodiments, the polyrotaxanes of the various embodiments of the present invention comprise from about 1 to about 10 HPβCD molecules and from about 1 to about 10 SBEβCD-F68.

Those of ordinary skill in the art will recognize that compounds described herein (e.g., the macrocyclic host molecule (A) or (A')) contain chiral centers. All diastereomers of the compounds described herein are contemplated herein, as well as racemates.

The polyrotaxanes of the various embodiments of the present invention are useful for treating Niemann-Pick type C (NPC) disease. NPC is a lysosomal storage disorder disease caused by accumulation of unesterified cholesterol and sphingolipids in the lysosomes of brain, liver, spleen, and lung cells. Aberrant accumulation of cholesterol in NPC cells has been shown to originate from mutation of the genes encoding either the membrane-bound NPC1 or the soluble NPC2 proteins required for cholesterol efflux from the lysosome. Unfortunately, the treatment options are limited for this typically fatal disease. Several studies have shown that s-cyclodextrin (β-CD) and its derivatives, including hydroxypropyl-β-cyclodextrin (HP-β-CD), are able to mobilize the removal of stored cholesterol from lysosomal compartments. Some groups have shown that the subcutaneous injection of HP-β-CD (4.0 mg/kg of body weight) into npc1$^{-/-}$ mice produced an improvement in their survival, hepatopathology, and neuropathology. Although these results are promising, it is still unclear how HP-β-CD solubilizes cholesterol from cells in human NPC1 disease. Furthermore, high dosages of the administered HP-β-CDs are required since their persistence in the bloodstream is brief (>90% is cleared within 24 h) due to their appreciable water solubility and relatively low molecular weight (=1460 g·mol$^{-1}$).

The polyrotaxanes of the various embodiments of the present invention can be long circulating; biocompatible; and can substantially increase cholesterol clearance from cells, such as NPC cells. Further, upon removal of the endcapping groups, they can deliver multiple "copies" of, e.g., HP-β-CD to the lysosomes of NPC cells. Analysis of certain polyrotaxanes of the various embodiments of the present invention in NPC2–/– fibroblast cells using filipin staining revealed that they promote the removal of aberrantly accumulated cholesterol from these cells. See Examples herein.

In some embodiments, therefore, the present invention contemplates methods for treating NPC comprising administering a therapeutically effective amount of at least one polyrotaxane of the various embodiments of the present invention or a composition (e.g., a pharmaceutical composition) comprising at least one polyrotaxane of the various embodiments of the present invention to a subject in need thereof.

In other embodiments, the present invention contemplates methods of removing cholesterol from the cells of an animal comprising administering a therapeutically effective amount of at least one polyrotaxane of the various embodiments of the present invention or a composition (e.g., a pharmaceutical composition) comprising at least one polyrotaxane of the various embodiments of the present invention to a subject in need thereof.

In some embodiments, the polyrotaxane contemplated for use in the methods for treating NPC or removing cholesterol from cells of an animal include, but are not limited to, polyrotaxanes having the general formula:

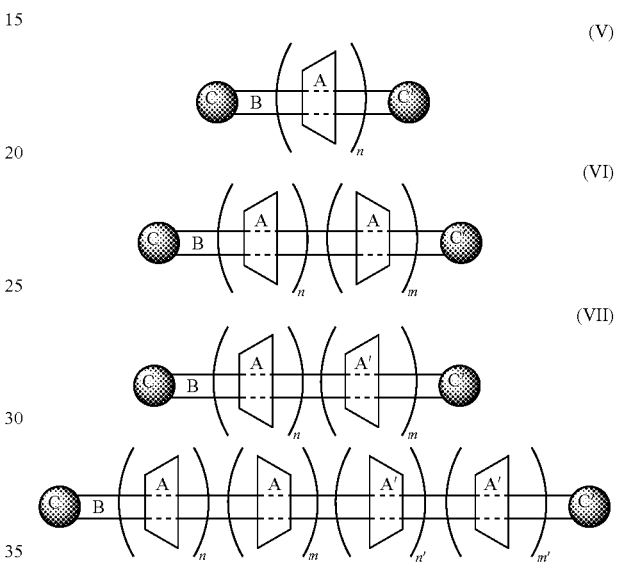

or combinations thereof or salts thereof, wherein A, A', B, C, C', n, m, n', and m' are as defined herein. In some embodiments, n is an integer from 0 to 30; m is an integer from 0 to 30 (e.g., n is an integer from 1 to 30; and m is an integer from 1 to 30); C and C' are the same or different and represent endcapping groups of the formula:

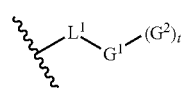

wherein L$^1$ is a (C$_1$-C$_5$)hydrocarbylene group, G$^1$ is a substituted or unsubstituted (C$_1$-C$_6$)hydrocarbylene group, interrupted by 0 to 5 groups chosen from —O—, —NH—, and —S—, G$^2$ is substituted or unsubstituted (C$_1$-C$_6$)hydrocarbylene-(C$_6$-C$_{50}$)hydrocarbyl group, interrupted by 0 to 5 groups chosen from —O—, —NH—, and —S—, wherein the (C$_6$-C$_{50}$)hydrocarbyl group is sterically bulky, and t is an integer from 2 to 5; B represents a polymer chain of the formula:

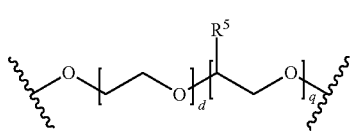

wherein each $R^5$ is independently a substituted or unsubstituted $(C_1-C_{20})$hydrocarbyl group, d is an integer from about 100 to about 800, and q is an integer from about 1 to about 800, wherein the polymer chain and the endcapping groups are covalently attached via any suitable linking group, including a suitable $(C_1-C_{20})$hydrocarbyl group (e.g., substituted or unsubstituted $(C_1-C_{12})$hydrocarbyl group; substituted or unsubstituted $(C_1-C_6)$hydrocarbyl group; or a substituted or unsubstituted $(C_1-C_3)$hydrocarbyl group), such as a $(C_1-C_6)$acyl group; and A represents the macrocyclic host molecule of the general formula (I) or (Ia):

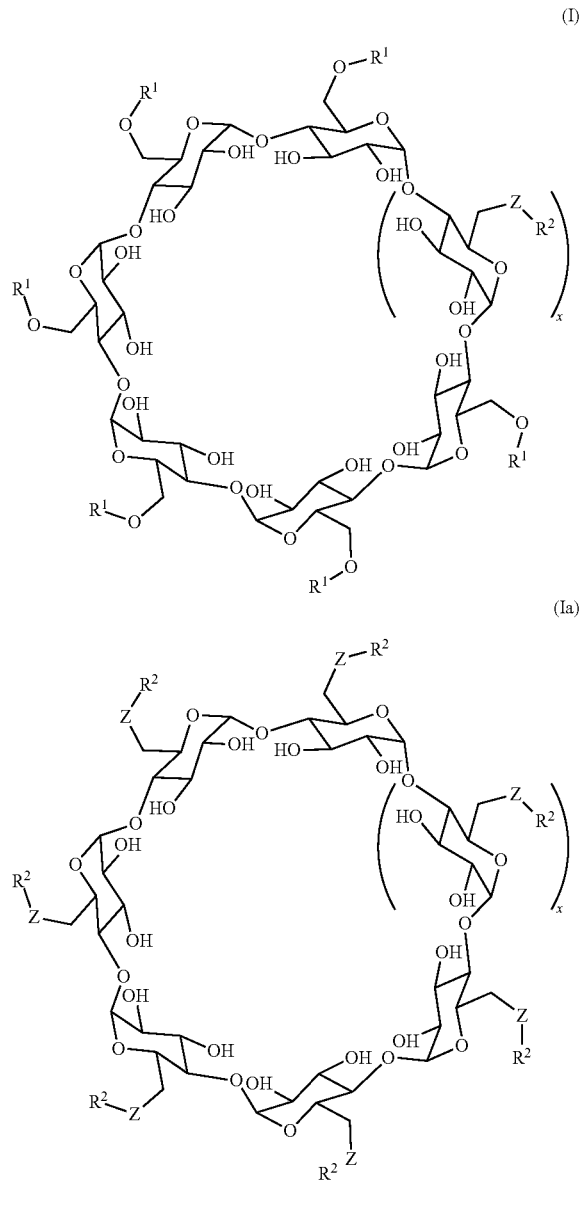

wherein each Z is O or $-N_3$, each $R^1$ is independently hydrogen or a substituted or unsubstituted $(C_1-C_{20})$hydrocarbyl group, interrupted by 0 to 5 groups chosen from $-O-$, $-NH-$, and $-S-$; x is an integer from 1 to 3; and $R^2$ is absent when Z is $-N_3$ or is substituted or unsubstituted $(C_1-C_{20})$hydrocarbyl group, interrupted by 0 to 5 groups chosen from $-O-$, $-NH-$, and $-S-$.

In some embodiments, C and C' are the same or different and represent endcapping groups of the formula:

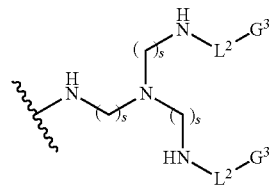

wherein each s is 2, each $L^2$ is a bond or $C=O$, and each $G^3$ is a cholesteryl group or a 2,4,6-trinitro phenyl group;

B represents a "polymer chain of compatible dimensions" of the formula:

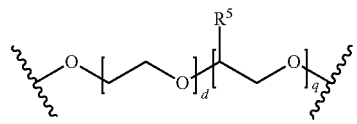

wherein $R^5$ is methyl and d and q are as defined herein, to which the endcapping groups are covalently attached to the polymer chain via any suitable linking group (e.g., $L^1$ herein), including a suitable $(C_1-C_6)$hydrocarbylene group, such as a $(C_1-C_6)$acyl group; and A represents the macrocyclic host molecule of the general formula (I) or (Ia):

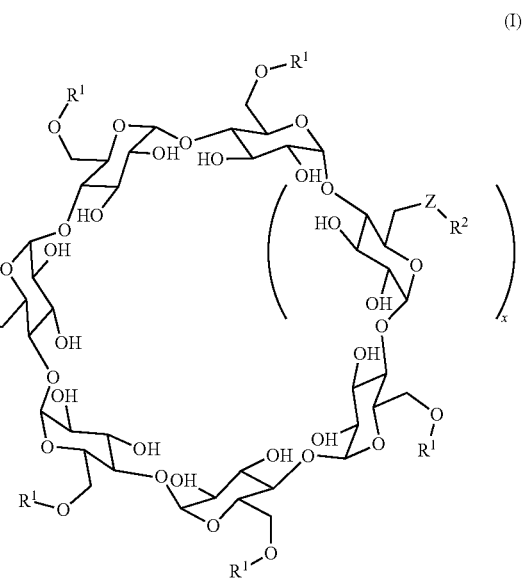

-continued

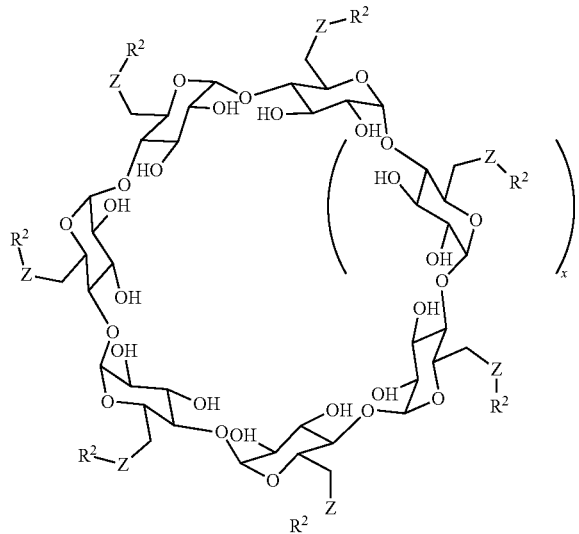

(Ia)

wherein each Z is O or —N₃, each $R^1$ is independently hydrogen or a substituted or unsubstituted $(C_1-C_{20})$hydrocarbyl group, interrupted by 0 to 5 groups chosen from —O—, —NH—, and —S—; x is an integer from 1 to 3; and $R^2$ is absent when Z is —N₃ or is substituted or unsubstituted $(C_1-C_{20})$hydrocarbyl group, interrupted by 0 to 5 groups chosen from —O—, —NH—, and —S—.

In some embodiments, x is 1; Z is O; $R^2$ is H; and $R^1$ is H.

In other embodiments, x is 1; Z is O; $R^2$ is substituted or unsubstituted $(C_1-C_6)$ alkyl group; and $R^1$ is substituted or unsubstituted $(C_1-C_6)$ alkyl group. In some embodiments, the $(C_1-C_6)$ alkyl group is substituted with —OH or —SO₃⁻.

In still other embodiments, x is 1; Z is —N₃; $R^2$ is absent; and $R^1$ is H.

Magnetic Resonance Imaging (MRI) is a powerful tool for high-resolution three-dimensional (3D) medical imaging of anatomical structures and specific organs or tissues within the body. MRI has advantages such as an absence of ionizing radiation, high contrast, high spatial resolution and excellent depth profiling capabilities. MRI has extensive applications in the diagnosis of various neurological, cardiovascular and oncological diseases. The quality and contrast of MRI images can be improved by the use of MRI contrast agents that enhance the image contrast within the tissue of interest by altering the longitudinal ($T_1$) and transverse ($T_2$) relaxation rates of the surrounding water protons. Contrast agents can be classified into either $T_1$ agents such as gadolinium (III) chelates, which increase the $T_1$ relaxation rate and produce a positive image contrast, or $T_2$ agents, such as supermagnetic iron oxide nanoparticles, which increase the $T_2$ relaxation rate and produce a negative image contrast.

A majority of clinically used contrast agents are $Gd^{3+}$ chelates, which are favored due to their high paramagnetism, excellent relaxation enhancement, and stability. Unfortunately, most clinically approved contrast agents suffer from rapid clearance from the body and ineffective contrast enhancement hence making them ineffective for angiographic enhancement. Thus, the use of macromolecules, macromolecular assemblies, and nanoparticles as carriers for contrast agents are attractive due to their long circulating properties and potential for tissue selectivity through the use of targeting ligands. Not only do such materials have better pharmacokinetics, they potentially can also carry a much higher $Gd^{3+}$ loading. Platforms such as dendrimers, polymers, liposomes, inorganic particles, and supramolecular assemblies, have been used as carriers of $Gd^{3+}$; however, most of these carriers suffer from issues such as acute toxicity and poor water accessibility due to $Gd^{3+}$ localization within the particle core.

In some embodiments, the present invention contemplates a polyrotaxane comprising a poloxamer core and at least one cyclodextrin comprising at least one nuclide chelating moiety. The polyrotaxanes of the various embodiments of the present invention can function as multivalent $Gd^{3+}$ carriers. For example, when the macrocyclic host molecule (A) comprises an $R^2$ group comprising a chelating moiety (e.g., a DOTA radical), the polyrotaxanes described herein are useful as imaging agents for MRI, when the chelating moiety comprises a nuclide, as the term is defined herein.

In some embodiments, therefore, the present invention contemplates methods for imaging comprising administering an amount sufficient for imaging of a polyrotaxane according to the various embodiments of the present invention or a composition comprising an amount sufficient for imaging of a polyrotaxane according to the various embodiments of the present invention, to a subject in need thereof.

In some embodiments, the polyrotaxanes useful in the method for imaging include, but are not limited to, polyrotaxanes having the general formula

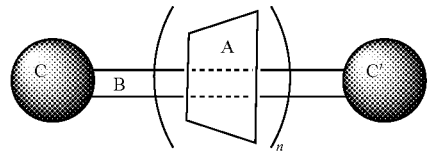

or a salt thereof,
wherein:
n is an integer from 1 to 30;
C and C' are the same or different and represent endcapping groups of the formula:

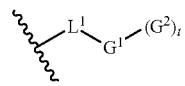

wherein $L^1$ is a $(C_1-C_6)$hydrocarbylene group, $G^1$ is a substituted or unsubstituted $(C_1-C_6)$hydrocarbylene group, interrupted by 0 to 5 groups chosen from —O—, —NH—, and —S—, $G^2$ is substituted or unsubstituted $(C_1-C_6)$hydrocarbylene-$(C_6-C_{50})$hydrocarbyl group, interrupted by 0 to 5 groups chosen from —O—, —NH—, and —S—, wherein the $(C_6-C_{50})$hydrocarbyl group is sterically bulky, and t is an integer from 2 to 5;
B represents a polymer chain of the formula:

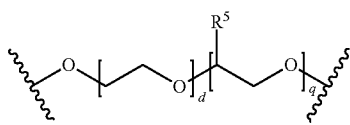

wherein each $R^5$ is independently a substituted or unsubstituted $(C_1-C_{20})$hydrocarbyl group, d is an integer from about 1 to about 800, and q is an integer from about 1 to about 800, wherein the polymer chain and the endcapping groups are covalently attached via any suitable linking group, including a suitable $(C_1-C_{20})$hydrocarbyl group (e.g., substituted or unsubstituted $(C_1-C_{12})$hydrocarbyl group; substituted or unsubstituted $(C_1-C_5)$hydrocarbyl group; or a substituted or unsubstituted $(C_1-C_3)$hydrocarbyl group), such as a $(C_1-C_6)$ acyl group; and A represents the macrocyclic host molecule of the general formula (I) or (Ia):

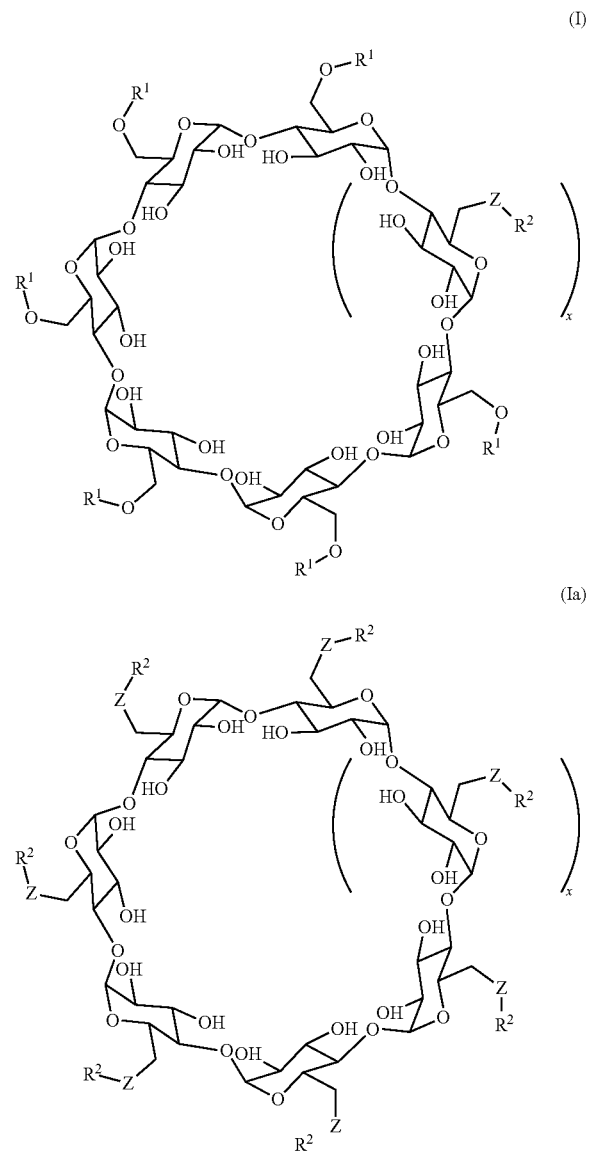

wherein each Z is independently O or NH, each $R^1$ is independently hydrogen or a substituted or unsubstituted $(C_1-C_{20})$hydrocarbyl group, interrupted by 0 to 5 groups chosen from —O—, —NH—, and —S—; x is an integer from 1 to 3; and $R^2$ is substituted or unsubstituted $(C_1-C_{20})$ hydrocarbyl group, interrupted by 0 to 5 groups chosen from —O—, —NH—, and —S—; with the proviso that at least one $R^2$ is $(C_1-C_{20})$hydrocarbyl group, interrupted by 0 to 5 groups chosen from —O—, —NH—, and —S—, substituted with a group C(S)N(R)$_2$, wherein one R is hydrogen and the other is an aryl group substituted with a radionuclide chelating moiety.

Embodiments of the present invention contemplate methods of making the rotaxanes of the various embodiments of the present invention by combining/contacting a suitable polymer chain (B) with a suitable macrocyclic host molecule (A) and/or (A') (e.g., under heterogeneous conditions) under non-aqueous conditions (e.g., in the presence of a non-polar solvent, such as diethyl ether, hexane or the like). In some embodiments, a suitable polymer chain (B) and a suitable macrocyclic host molecule (A) and/or (A') are contacted for an amount of time sufficient (e.g., 48 hours) for the macrocyclic host molecule (A) or (A') to "thread" onto the polymer chain (B), such that at least one (e.g., 1 to 30, 1 to 20, 1 to 15, 5 to 15, 3 to 11, 1 to 12, 2 to 12 or 2 to 18) macrocyclic host molecule is threaded onto the polymer chain. The ends of the polymer chain (B), comprising that at least one (e.g., 1 to 30, 1 to 20, 1 to 15, 5 to 15, 3 to 11, 1 to 12, 2 to 12 or 2 to 18) macrocyclic host molecule threaded onto the polymer chain are subsequently "capped" using the capping methods described herein or those known in the art. See, e.g., C. J. Collins et al., *Biochemistry* 52: 3242-3253 (2013), which is incorporated by reference as if fully set forth herein.

Pharmaceutical Compositions

Various embodiments of the present invention also contemplate pharmaceutical compositions comprising one or more compounds of the various embodiments of the present invention and one or more pharmaceutically acceptable excipients. A "pharmaceutical composition" refers to a chemical or biological composition suitable for administration to a subject (e.g., an animal, such as, but not limited to, a mammal). Such compositions may be specifically formulated for administration via one or more of a number of routes, including but not limited to buccal, cutaneous, epicutaneous, epidural, infusion, inhalation, intraarterial, intracardial, intracerebroventricular, intradermal, intramuscular, intranasal, intraocular, intraperitoneal, intraspinal, intrathecal, intravenous, oral, parenteral, pulmonary, rectally via an enema or suppository, subcutaneous, subdermal, sublingual, transdermal, and transmucosal. In addition, administration can by means of capsule, drops, foams, gel, gum, injection, liquid, patch, pill, porous pouch, powder, tablet, or other suitable means of administration.

A "pharmaceutical excipient" or a "pharmaceutically acceptable excipient" comprises a carrier, sometimes a liquid, in which an active therapeutic agent is formulated. The excipient generally does not provide any pharmacological activity to the formulation, though it may provide chemical and/or biological stability, and release characteristics. Examples of suitable formulations can be found, for example, in Remington, The Science And Practice of Pharmacy, 20th Edition, (Gennaro, A. R., Chief Editor), Philadelphia College of Pharmacy and Science, 2000, which is incorporated by reference in its entirety.

As used herein "pharmaceutically acceptable carrier" or "excipient" includes any and all solvents, dispersion media, coatings, antibacterial and antifungal agents, isotonic and absorption delaying agents that are physiologically compatible. In one embodiment, the carrier is suitable for parenteral administration. Alternatively, the carrier can be suitable for intravenous, intraperitoneal, intramuscular, sublingual, or oral administration. Pharmaceutically acceptable carriers include sterile aqueous solutions or dispersions and sterile powders for the extemporaneous preparation of sterile injectable solutions or dispersion. The use of such media and agents for pharmaceutically active substances is well known in the art. Except insofar as any conventional media or agent is incompatible with the active compound, use thereof in the pharmaceutical compositions of the invention is contemplated. Supplementary active compounds can also be incorporated into the compositions.

Pharmaceutical compositions may be sterile and stable under the conditions of manufacture and storage. The composition can be formulated as a solution, microemulsion, liposome, or other ordered structure suitable to high drug concentration. The carrier can be a solvent or dispersion medium containing, for example, water, ethanol, polyol (e.g., glycerol, propylene glycol, and liquid polyethylene glycol), and suitable mixtures thereof. The proper fluidity can be maintained, for example, by the use of a coating such as lecithin, by the maintenance of the required particle size in the case of dispersion and by the use of surfactants.

In many cases, it will be preferable to include isotonic agents, for example, polysaccharides, polyalcohols such as mannitol, sorbitol, or sodium chloride in the composition. Prolonged absorption of the injectable compositions can be brought about by including in the composition an agent which delays absorption, for example, monostearate salts and gelatin. Moreover, the compounds described herein can be formulated in a time release formulation, for example in a composition that includes a slow release polymer. The active compounds can be prepared with carriers that will protect the compound against rapid release, such as a controlled release formulation, including implants and microencapsulated delivery systems. Biodegradable, biocompatible polymers may be used, such as ethylene vinyl acetate, polyanhydrides, polyglycolic acid, collagen, polyorthoesters, polylactic acid and polylactic, polyglycolic copolymers (PLG). Many methods for the preparation of such formulations are known to those skilled in the art.

Oral forms of administration are also contemplated herein. The pharmaceutical compositions of the present invention may be orally administered as a capsule (hard or soft), tablet (film coated, enteric coated or uncoated), powder or granules (coated or uncoated) or liquid (solution or suspension). The formulations may be conveniently prepared by any of the methods well-known in the art. The pharmaceutical compositions of the present invention may include one or more suitable production aids or excipients including fillers, binders, disintegrants, lubricants, diluents, flow agents, buffering agents, moistening agents, preservatives, colorants, sweeteners, flavors, and pharmaceutically compatible carriers.

For each of the recited embodiments, the compounds can be administered by a variety of dosage forms as known in the art. Any biologically-acceptable dosage form known to persons of ordinary skill in the art, and combinations thereof, are contemplated. Examples of such dosage forms include, without limitation, chewable tablets, quick dissolve tablets, effervescent tablets, reconstitutable powders, elixirs, liquids, solutions, suspensions, emulsions, tablets, multi-layer tablets, bi-layer tablets, capsules, soft gelatin capsules, hard gelatin capsules, caplets, lozenges, chewable lozenges, beads, powders, gum, granules, particles, microparticles, dispersible granules, cachets, douches, suppositories, creams, topicals, inhalants, aerosol inhalants, patches, particle inhalants, implants, depot implants, ingestibles, injectables (including subcutaneous, intramuscular, intravenous, and intradermal), infusions, and combinations thereof.

Other compounds which can be included by admixture are, for example, medically inert ingredients (e.g., solid and liquid diluent), such as lactose, dextrosesaccharose, cellulose, starch or calcium phosphate for tablets or capsules, olive oil or ethyl oleate for soft capsules and water or vegetable oil for suspensions or emulsions; lubricating agents such as silica, talc, stearic acid, magnesium or calcium stearate and/or polyethylene glycols; gelling agents such as colloidal clays; thickening agents such as gum tragacanth or sodium alginate, binding agents such as starches, arabic gums, gelatin, methylcellulose, carboxymethylcellulose or polyvinylpyrrolidone; disintegrating agents such as starch, alginic acid, alginates or sodium starch glycolate; effervescing mixtures; dyestuff; sweeteners; wetting agents such as lecithin, polysorbates or laurylsulphates; and other therapeutically acceptable accessory ingredients, such as humectants, preservatives, buffers and antioxidants, which are known additives for such formulations.

Liquid dispersions for oral administration can be syrups, emulsions, solutions, or suspensions. The syrups can contain as a carrier, for example, saccharose or saccharose with glycerol and/or mannitol and/or sorbitol. The suspensions and the emulsions can contain a carrier, for example a natural gum, agar, sodium alginate, pectin, methylcellulose, carboxymethylcellulose, or polyvinyl alcohol.

The amount of active compound in a therapeutic composition according to various embodiments of the present invention may vary according to factors such as the disease state, age, gender, weight, patient history, risk factors, predisposition to disease, administration route, pre-existing treatment regime (e.g., possible interactions with other medications), and weight of the individual. Dosage regimens may be adjusted to provide the optimum therapeutic response. For example, a single bolus may be administered, several divided doses may be administered over time, or the dose may be proportionally reduced or increased as indicated by the exigencies of therapeutic situation.

"Dosage unit form," as used herein, refers to physically discrete units suited as unitary dosages for the mammalian subjects to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of sensitivity in individuals. In therapeutic use for treatment of conditions in mammals (e.g., humans) for which the compounds of the present invention or an appropriate pharmaceutical composition thereof are effective, the compounds of the present invention may be administered in an effective amount. The dosages as suitable for this invention may be a composition, a pharmaceutical composition or any other compositions described herein.

For each of the recited embodiments, the dosage is typically administered once, twice, or thrice a day, although more frequent dosing intervals are possible. The dosage may be administered every day, every 2 days, every 3 days, every 4 days, every 5 days, every 6 days, and/or every 7 days (once a week). In one embodiment, the dosage may be administered daily for up to and including 30 days, preferably between 7-10 days. In another embodiment, the dosage may be administered twice a day for 10 days. If the patient requires treatment for a chronic disease or condition, the dosage may be administered for as long as signs and/or symptoms persist. The patient may require "maintenance treatment" where the patient is receiving dosages every day for months, years, or the remainder of their lives. In addition, the composition of this invention may be to effect prophylaxis of recurring symptoms. For example, the dosage may be administered once or twice a day to prevent the onset of symptoms in patients at risk, especially for asymptomatic patients.

The compositions described herein may be administered in any of the following routes: buccal, epicutaneous, epidural, infusion, inhalation, intraarterial, intracardial, intracerebroventricular, intradermal, intramuscular, intranasal, intraocular, intraperitoneal, intraspinal, intrathecal, intravenous, oral, parenteral, pulmonary, rectally via an enema or suppository, subcutaneous, subdermal, sublingual, transdermal, and transmucosal. The preferred routes of administration are buccal, oral, and intravenous. The administration can be local, where the composition is administered directly, close to, in the locality, near, at, about, or in the vicinity of, the site(s) of disease, e.g., inflammation, or systemic, wherein the composition is given to the patient and passes through the body widely, thereby reaching the site(s) of disease. Local administration can be administration to the cell, tissue, organ, and/or organ system, which encompasses and/or is affected by the disease, and/or where the disease signs and/or symptoms are active or are likely to occur. Local administration can also be administration to the cell, tissue, organ, and/or organ system, which requires imaging (e.g., magnetic resonance imaging).

Administration can be topical with a local effect, composition is applied directly where its action is desired. Administration can be enteral wherein the desired effect is systemic (non-local), composition is given via the digestive tract. Administration can be parenteral, where the desired effect is systemic, composition is given by other routes than the digestive tract.

The term "therapeutically effective amount" as used herein, refers to that amount of one or more compounds of the various embodiments of the present invention that elicits a biological or medicinal response in a tissue system, animal or human, that is being sought by a researcher, veterinarian, medical doctor or other clinician, which includes alleviation of the symptoms of the disease or disorder being treated. In some embodiments, the therapeutically effective amount is that which may treat or alleviate the disease or symptoms of the disease at a reasonable benefit/risk ratio applicable to any medical treatment. However, it is to be understood that the total daily usage of the compounds and compositions described herein may be decided by the attending physician within the scope of sound medical judgment. The specific therapeutically-effective dose level for any particular patient will depend upon a variety of factors, including the condition being treated and the severity of the condition; activity of the specific compound employed; the specific composition employed; the age, body weight, general health, gender and diet of the patient: the time of administration, route of administration, and rate of excretion of the specific compound employed; the duration of the treatment; drugs used in combination or coincidentally with the specific compound employed; and like factors well known to the researcher, veterinarian, medical doctor or other clinician. It is also appreciated that the therapeutically effective amount can be selected with reference to any toxicity, or other undesirable side effect, that might occur during administration of one or more of the compounds described herein.

Definitions

The term "about" as used herein can allow for a degree of variability in a value or range, for example, within 10%, within 5%, or within 1% of a stated value or of a stated limit of a range.

The term "substantially" as used herein refers to a majority of, or mostly, as in at least about 50%, 60%, 70%, 80%, 90%, 95%, 96%, 97%, 98%, 99%, 99.5%, 99.9%, 99.99%, or at least about 99.999% or more.

Values expressed in a range format should be interpreted in a flexible manner to include not only the numerical values explicitly recited as the limits of the range, but also to include all the individual numerical values or sub-ranges encompassed within that range as if each numerical value and sub-range were explicitly recited. For example, a range of "about 0.1% to about 5%" or "about 0.1% to 5%" should be interpreted to include not just about 0.1% to about 5%, but also the individual values (e.g., 1%, 2%, 3%, and 4%) and the sub-ranges (e.g., 0.1% to 0.5%, 1.1% to 2.2%, 3.3% to 4.4%) within the indicated range. The statement "about X to Y" has the same meaning as "about X to about Y," unless indicated otherwise. Likewise, the statement "about X, Y, or about Z" has the same meaning as "about X, about Y, or about Z," unless indicated otherwise.

In this document, the terms "a," "an," or "the" are used to include one or more than one unless the context clearly dictates otherwise. The term "or" is used to refer to a nonexclusive "or" unless otherwise indicated. In addition, it is to be understood that the phraseology or terminology employed herein, and not otherwise defined, is for the purpose of description only and not of limitation. Any use of section headings is intended to aid reading of the document and is not to be interpreted as limiting. Further, information that is relevant to a section heading may occur within or outside of that particular section. Furthermore, all publications, patents, and patent documents referred to in this document are incorporated by reference herein in their entirety, as though individually incorporated by reference. In the event of inconsistent usages between this document and those documents so incorporated by reference, the usage in the incorporated reference should be considered supplementary to that of this document; for irreconcilable inconsistencies, the usage in this document controls.

In the methods described herein, the steps can be carried out in any order without departing from the principles of the invention, except when a temporal or operational sequence is explicitly recited. Furthermore, specified steps can be carried out concurrently unless explicit claim language recites that they be carried out separately. For example, a claimed step of doing X and a claimed step of doing Y can be conducted simultaneously within a single operation, and the resulting process will fall within the literal scope of the claimed process.

As used herein, the term "hydrocarbyl" refers to a functional group derived from a straight chain, branched, or cyclic hydrocarbon, and can be alkyl, alkenyl, alkynyl, aryl, cycloalkyl, or any combination thereof. The hydrocarbyl group can have 1 to 50 carbon atoms ($C_1$-$C_{50}$), 10 to 30 carbon atoms ($C_{10}$-$C_{30}$), 12 to 18 carbon atoms ($C_{12}$-$C_{18}$), 1 to about 20 carbon atoms ($C_1$-$C_{20}$), 1 to 10 carbons ($C_1$-$C_{10}$), 1 to 8 carbon atoms ($C_1$-$C_8$), 1 to 5 carbon atoms ($C_1$-$C_5$) or, in some embodiments, from 1 to 3 carbon atoms ($C_1$-$C_3$).

As used herein, the term "hydrocarbylene" broadly refers to a divalent functional group derived from a straight chain, branched, or cyclic hydrocarbon, such as an alkylene (e.g., —$CH_2$— and —$CH_2CH_2$—), alkenylene (e.g., —CH═CH— and —CH═CH—$CH_3$, wherein, when applicable, the double bond geometry may be E-, Z- or a mixture of E- and Z-), alkynylene (e.g., —C≡C— and —C≡C—CH₃), arylene (e.g., phenylene), cycloalkylene (e.g., cyclopentylene and cyclohexylene), divalent acyl (e.g., —C(=O)— and —CH₂C(=O)—CH₂), or a combination thereof. Hydrocarbylene groups can be unsubstituted or substituted, as defined herein.

The hydrocarbyl group can be substituted or unsubstituted. The term "substituted" as used herein refers to an organic group as defined herein or molecule in which one or more hydrogen atoms contained therein are replaced by one or more non-hydrogen atoms. The term "functional group" or "substituent" as used herein refers to a group that can be or is substituted onto a molecule or onto an organic group. The "substituent" can also be an organic group. Examples of substituents or functional groups include, but are not limited to, a halogen (e.g., F, Cl, Br, and I); an oxygen atom in groups such as hydroxyl groups, alkoxy groups, aryloxy groups, aralkyloxy groups, oxo(carbonyl) groups, carboxyl groups including carboxylic acids, carboxylates, and carboxylate esters; a sulfur atom in groups such as thiol groups, alkyl and aryl sulfide groups, sulfoxide groups, sulfone groups, sulfonyl groups, and sulfonamide groups; a nitrogen atom in groups such as amines, hydroxylamines, nitriles, nitro groups, N-oxides, hydrazides, azides, and enamines; and other heteroatoms in various other groups.

The term "organic group" as used herein refers to but is not limited to, any carbon-containing functional group. For example, an oxygen-containing group such as an alkoxy group, aryloxy group, aralkyloxy group, oxo(carbonyl) group, a carboxyl group including a carboxylic acid, carboxylate, and a carboxylate ester; a sulfur-containing group such as an alkyl and aryl sulfide group; and other heteroatom-containing groups. Non-limiting examples of organic groups include OR, OOR, OC(O)N(R)(R'), CN, CF₃, OCF₃, R, C(O), methylenedioxy, ethylenedioxy, N(R)(R'), SR, SOR, SO₂R, SO₂N(R)(R'), SO₃R, C(O)R, C(O)C(O)R, C(O)CH₂C(O)R, C(S)R, C(O)OR, OC(O)R, C(O)N(R)(R'), OC(O)N(R)(R'), C(S)N(R)(R'), (CH₂)₀₋₂N(R)C(O)R', (CH₂)₀₋₂N(R)N(R)(R'), N(R)N(R)C(O)R', N(R)N(R)C(O)OR', N(R)N(R)CON(R)(R'), N(R)SO₂R', N(R)SO₂N(R)(R'), N(R)C(O)OR', N(R)C(O)R', N(R)C(S)R', N(R)C(O)N(R)(R'), N(R)C(S)N(R)(R'), N(COR)COR', N(OR)R', C(=NH)N(R)(R'), C(O)N(OR)R', or C(=NOR)R; wherein each R and R' can be, independently, hydrogen (in examples that include other carbon atoms) or a carbon-based moiety (e.g., alkyl, cycloalkyl, heterocycloalkyl, aryl, and heteroaryl), and wherein the carbon-based moiety can itself be further substituted.

Organic groups also include chelating moieties, also referred to herein as "nuclide chelating moiety," such as, but not limited to, diethylenetriamine pentaacetic acid (DTPA), 1,4,7,10-tetraazacyclododecane-1,4,7,10-tetraacetic acid (DOTA), triethylenetetramine (TETA), 1,4,7-triazacyclononane-triacetic acid (NOTA), and the like, that are capable of chelating, e.g., a radionuclide or a paramagnetic nuclide. Examples of nuclides include, but are not limited to, In-111, Y-90, F-18, P-32, Sc-47, Cu-62, Cu-64, Cu-67, Ga-67, Ga-68, Y-86, Y-90, Zr-89, Tc-99m, Pd-109, Ag-111, In-111, I-123, I-125, I-131, Sm-153, Gd-155, Gd-157, Th-161, Lu-177, Re-186, Re-188, Pt-197, Pb-212, Bi-212, Bi-213, Ra-223, Ac-225, As-72, As-77, At-211, Au-198, Au-199, Bi-212, Br-75, Br-76B, C-11, Co-55Co, Dy-166, Er-169, F-18, Fe-52, Fe-59, Ga-67, Ga-68, Gd-154-158, Ho-166, I-120, I-121, I-124, In-110, In-111, M194, Lu-177, Mn-51, Mn-52, Mo-99, N-13, O-15, P-32, P-33, Pb-211, Pb-212, Pd-109, Pm-149, Pr-142, Pr-143, Rb-82, Re-189, Rh-105, Sc-47, Se-75, Sr-83, Sr-89, Th-161, Tc-94, Tc-99, Y-86, Y-90 and Zr-89. Examples of paramagnetic nuclides include, but are not limited to $Gd^{3+}$, $Mn^{2+}$, and $Fe^{3+}$.

Non-limiting examples of substituents, J, that can be bonded to a substituted carbon (or other) atom include F, Cl, Br, I, OR, OC(O)N(R')₂, CN, NO, NO₂, ONO₂, azido, CF₃, OCF₃, R', O (oxo), S (thiono), C(O), S(O), methylenedioxy, ethylenedioxy, N(R)₂, SR, SOR, SO₂R', SO₂N(R)₂, SO₃R, C(O)R, C(O)C(O)R, C(O)CH₂C(O)R, C(S)R, C(O)OR, OC(O)R, C(O)N(R)₂, OC(O)N(R)₂, C(S)N(R)₂, (CH₂)₀₋₂N(R)C(O)R, (CH₂)₀₋₂N(R)N(R)₂, N(R)N(R)C(O)R, N(R)N(R)C(O)OR, N(R)N(R)CON(R)₂, N(R)SO₂R, N(R)SO₂N(R)₂, N(R)C(O)OR, N(R)C(O)R, N(R)C(S)R, N(R)C(O)N(R)₂, N(R)C(S)N(R)₂, N(COR)COR, N(OR)R, C(=NH)N(R)₂, C(O)N(OR)R, or C(=NOR)R, wherein R can be hydrogen or a carbon-based moiety, and wherein the carbon-based moiety can itself be further substituted; for example, wherein R can be hydrogen, alkyl, acyl, cycloalkyl, aryl, aralkyl, heterocyclyl, heteroaryl, or heteroarylalkyl, wherein any alkyl, acyl, cycloalkyl, aryl, aralkyl, heterocyclyl, heteroaryl, or heteroarylalkyl or R can be independently mono- or multi-substituted with J; or wherein two R groups bonded to a nitrogen atom or to adjacent nitrogen atoms can together with the nitrogen atom or atoms form a heterocyclyl, which can be mono- or independently multi-substituted with J.

The term "alkyl" and "alkylene," as used herein, refer to substituted or unsubstituted straight chain and branched alkyl and alkylene groups and cycloalkyl and cycloalkylene groups having from 1 to 50 carbon atoms, 10 to 30 carbon atoms, 12 to 18 carbon atoms, 1 to about 20 carbon atoms, 1 to 10 carbons, 1 to 8 carbon atoms, 1 to 5 carbon atoms or, in some embodiments, from 1 to 3 carbon atoms. Examples of straight chain alkyl groups include those with from 1 to 8 carbon atoms such as methyl, ethyl, n-propyl, n-butyl, n-pentyl, n-hexyl, n-heptyl, n-octyl groups. Examples of branched alkyl groups include, but are not limited to, isopropyl, iso-butyl, sec-butyl, t-butyl, neopentyl, isopentyl, 2,2-dimethylpropyl, and isostearyl groups. As used herein, the term "alkyl" and "alkylene" encompasses n-alkyl and n-alkylene; isoalkyl and isoalkylene; and anteisoalkyl and anteisoalkylene groups as well as other branched chain forms of alkyl and alkylene.

The term "alkenyl" and "alkenylene," as used herein, refer to substituted or unsubstituted straight and branched chain and cyclic alkyl and alkylene groups as defined herein, except that at least one double bond exists between two carbon atoms. Thus, alkenyl and alkenylene groups have from 2 to 50 carbon atoms, or 2 to about 20 carbon atoms, or 2 to 12 carbons or, in some embodiments, from 2 to 8 carbon atoms. Examples of alkenyl groups include, but are not limited to vinyl, —CH=CH(CH₃), —CH=C(CH₃)₂, —C(CH₃)=CH₂, —C(CH₃)=CH(CH₃), —C(CH₂CH₃) =CH₂, cyclohexenyl, cyclopentenyl, cyclohexadienyl, butadienyl, pentadienyl, and hexadienyl among others.

The term "alkynyl" and "alkynylene," as used herein, refer to substituted or unsubstituted straight and branched chain alkyl and alkylene groups, except that at least one triple bond exists between two carbon atoms. Thus, alkynyl and alkynylene groups have from 2 to 50 carbon atoms, 2 to about 20 carbon atoms, or from 2 to 12 carbons or, in some embodiments, from 2 to 8 carbon atoms. Examples include, but are not limited to —C≡CH, —C≡C(CH₃), —C≡C (CH₂CH₃), —CH₂C≡CH, —CH₂C≡C(CH₃), and —CH₂C≡C(CH₂CH₃) among others.

The term "acyl" as used herein refers to a group containing a carbonyl moiety wherein the group is bonded via the carbonyl carbon atom. The carbonyl carbon atom is also bonded to another carbon atom, which can be part of an alkyl, aryl, aralkyl cycloalkyl, cycloalkylalkyl, heterocyclyl, heterocyclylalkyl, heteroaryl, heteroarylalkyl group or the like. In the special case wherein the carbonyl carbon atom is bonded to a hydrogen, the group is a "formyl" group, an acyl group as the term is defined herein. An acyl group can include 0 to about 12-20 or 12-50 additional carbon atoms bonded to the carbonyl group. An acyl group can include double or triple bonds within the meaning herein. An acryloyl group is an example of an acyl group. An acyl group can also include heteroatoms (e.g., —O—, —NH—, and —S—). A nicotinoyl group (pyridyl-3-carbonyl) is an example of an acyl group within the meaning herein. Other examples include acetyl, benzoyl, phenylacetyl, pyridylacetyl, cinnamoyl, and acryloyl groups and the like. When the group containing the carbon atom that is bonded to the carbonyl carbon atom contains a halogen, the group is termed a "haloacyl" group. An example is a trifluoroacetyl group.

The term "aryl" and "arylene," as used herein, refer to substituted or unsubstituted cyclic aromatic hydrocarbons that do not contain heteroatoms in the ring. Thus aryl groups include, but are not limited to, phenyl, azulenyl, heptalenyl, biphenyl, indacenyl, fluorenyl, phenanthrenyl, triphenylenyl, pyrenyl, naphthacenyl, chrysenyl, biphenylenyl, anthracenyl, and naphthyl groups. In some embodiments, aryl and arylene groups contain about 6 to about 14 carbons in the ring portions of the groups. Representative substituted aryl groups can be mono-substituted or substituted more than once, such as, but not limited to, 2-, 3-, 4-, 5-, or 6-substituted phenyl or 2-8 substituted naphthyl groups.

The term "heterocyclyl," as used herein, refers to substituted or unsubstituted aromatic and non-aromatic ring compounds containing 3 or more ring members, of which, one or more is a heteroatom such as, but not limited to, N, O, and S. Thus, a heterocyclyl can be a cycloheteroalkyl, or a heteroaryl, or if polycyclic, any combination thereof. In some embodiments, heterocyclyl groups include 3 to about 20 ring members, whereas other such groups have 3 to about 15 ring members. A heterocyclyl group designated as a $C_2$-heterocyclyl can be a 5-ring with two carbon atoms and three heteroatoms, a 6-ring with two carbon atoms and four heteroatoms and so forth. Likewise a $C_4$-heterocyclyl can be a 5-ring with one heteroatom, a 6-ring with two heteroatoms, and so forth. The number of carbon atoms plus the number of heteroatoms equals the total number of ring atoms. A heterocyclyl ring can also include one or more double bonds. A heteroaryl ring is an embodiment of a heterocyclyl group. The phrase "heterocyclyl group" includes fused ring species including those that include fused aromatic and non-aromatic groups. Examples of heterocyclyl groups include pyridinyl, pyrimidinyl, pyrazinyl, triazinyl, tetrazinyl, quinolinyl, quinazolinyl, quinoxalinyl, thienyl, pyrazolyl, imidazolyl, oxazolyl, thiazolyl, isoxazolyl, isothiazolyl, oxadiazolyl, thiadiazolyl, triazolyl (e.g., 1,2,4-triazolyl), benzimidazolyl, benzoxazolyl, benzthiazolyl, benzisoxazolyl, benzisothiazolyl, and the like. Examples of heterocyclyl groups also include tetrahydrofuryl, pyrrolidinyl, tetrahydropyranyl, piperidinyl, morpholinyl, piperazinyl, homopiperazinyl, quinuclidinyl, and the like.

The term "alkoxy" as used herein refers to an oxygen atom connected to an alkyl group, including a cycloalkyl group, as are defined herein. Examples of linear alkoxy groups include but are not limited to methoxy, ethoxy, propoxy, butoxy, pentyloxy, hexyloxy, and the like. Examples of branched alkoxy include but are not limited to isopropoxy, sec-butoxy, tert-butoxy, isopentyloxy, isohexyloxy, and the like. Examples of cyclic alkoxy include but are not limited to cyclopropyloxy, cyclobutyloxy, cyclopentyloxy, cyclohexyloxy, and the like. An alkoxy group can include one to about 12-20 or about 12-40 carbon atoms bonded to the oxygen atom, and can further include double or triple bonds, and can also include heteroatoms. For example, an allyloxy group is an alkoxy group within the meaning herein. A methoxyethoxy group is also an alkoxy group within the meaning herein, as is a methylenedioxy group in a context where two adjacent atoms of a structure are substituted therewith.

The terms "halo," "halogen," or "halide" group, as used herein, by themselves or as part of another substituent, mean, unless otherwise stated, a fluorine, chlorine, bromine, or iodine atom.

The term "haloalkyl" group, as used herein, includes mono-halo alkyl groups, poly-halo alkyl groups wherein all halo atoms can be the same or different, and per-halo alkyl groups, wherein all hydrogen atoms are replaced by halogen atoms, such as fluoro. Examples of haloalkyl include trifluoromethyl, 1,1-dichloroethyl, 1,2-dichloroethyl, 1,3-dibromo-3,3-difluoropropyl, perfluorobutyl, —$CF(CH_3)_2$ and the like.

As used herein, the term "salts" and "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic groups such as amines; and alkali or organic salts of acidic groups such as carboxylic acids. Pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, and nitric; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, and isethionic, and the like.

Pharmaceutically acceptable salts can be synthesized from the parent compound which contains a basic or acidic moiety by conventional chemical methods. In some instances, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in Remington's Pharmaceutical Sciences, 17th ed., Mack Publishing Company, Easton, Pa., 1985, the disclosure of which is hereby incorporated by reference.

EXAMPLES

The present invention can be better understood by reference to the following examples which are offered by way of illustration. The present invention is not limited to the examples given herein.

Materials. PLURONIC® triblock copolymers F127 (EO 200, PO 65), F68 (EO 153, PO 29), L35 (EO 22, PO 16), L64 (EO 26, PO 30), and L81 (EO 6, PO 43) were purchased from Sigma Aldrich and dried by azeotropic distillation from benzene under vacuum before use. 2-Hydroxypropyl-β-cyclodextrin, carbonyldiimidazole (CDI), triethylamine (TEA), tris(2-aminoethyl)amine (TAEA), were also purchased from Sigma-Aldrich and were used directly. 2,4,6-Trinitrobenzenesulfonic acid (TNBS) solution, 10% w/v in water, was obtained from Research Organics in Cleveland, Ohio and used as received. All solvents were distilled from an appropriate desiccant prior to use. Dialysis cellulose membranes were obtained from Spectrum Labs Inc. and immersed in deionized water for at least 30 min prior to use. Ultra-pure water (resistivity=18.0 MΩ/cm$^{-1}$) was generated from a NANOpure Ultrapure water system.

Ultraviolet-Visible spectroscopy. Absorption spectra, recorded using a HP8453 UV-Vis spectrophotometer equipped with tungsten and deuterium lamps, were measured to confirm the effectiveness of, e.g., TNBS endcapping reactions of polyrotaxanes of the various embodiments of the present invention. The samples were dissolved in water (1 mg/mL) and spectra were recorded at 20° C.

Matrix Assisted Laser Desorption Ionization Time-Of-Flight, MALDI-TOF. MALDI-MS spectra were acquired over a mass range of 1500-35000 Da in positive-ion reflector mode on an Applied Biosystems/MDS Sciex 4800 MALDI-TOF/TOF Analyzer with 4000 Series Explorer v3.5 software using a laser power of 6000 and 6500 laser shots in linear mode. The matrix included a freshly prepared ionic liquid matrix (ILM) made using a previously described protocol with some modifications. Briefly, 2',4',6'-trihydroxyacetophenone monohydrate (THAP) and 1,1,3,3-tetramethylguanidine (TMG) were mixed at a molar ratio of 1:2 in methanol. The solution was then sonicated for 15 min at 40° C. After removal of methanol by centrifugal evaporation in a SpeedVac for 3 h at 20° C., ILMs were left under a 50 m Hg vacuum overnight. Final ILM solutions were then prepared at a concentration of 90 mg/mL in DMF for use as a matrix. The polyrotaxanes samples were prepared at 3 mg/mL in DMF and then mixed in a 1:80 polyrotaxane:ILM ratio for MALDI-MS analysis. Then, 0.6 μL of a polyrotaxane:ILM mixture was deposited onto a mirror-polished stainless steel MALDI target and allowed to dry at 20° C. under atmospheric pressure overnight before analysis.

Atomic Force Microscopy. Topology (size, height) of polyrotaxane particles were determined in air at 22° C. by tapping-mode atomic force microscopy using a Multimode AFM equipped with Nanoscope IIIa controller (Veeco Instruments, USA), an uncoated probe tip of 10 nm of less (NSC15/A1BS, MikroMasch, USA), and cantilevers having a spring constant of 40 N/m. In a typical measurement, 7.0 μL of a polyrotaxane sample (1.0×10$^{-9}$ mg/mL in water) were deposited onto a mica surface after cleaning by probe sonication and water removal using a TechSpray duster containing 1,1,1,2-tetrafluoroethane gas.

High-Performance and Ultra-Performance Liquid Chromatography, HPLC/UPLC. An Agilent Series 1200 HPLC coupled with an ESA Corona detector was employed for the dethreading studies of polyrotaxanes of the various embodiments of the present invention. In this assay, the cyclodextrin peak in the chromatogram was integrated and the concentration of HP-β-CD, obtained from the polyrotaxanes cleavage, was determined by comparison with a standard curve for 1 mL aliquots of aqueous solution of polyrotaxane solution that were treated with one of two different buffers (pH 7.4 and pH 5.5) at 37° C. The aqueous solutions of polyrotaxanes (2.0 mg/mL) were filtered through a 0.2 μm cellulose membrane filter before injection. The calibration curve was constructed by analyzing different concentrations of HP-β-CD standard dissolved in water. The separation was performed at 50° C. on an Agilent reversed-phase Zorbax Eclipse XDB-phenyl column (2.1 mm×150 mm, particle size 5 μm). The mobile phase composition was a mixture of water (A) and acetonitrile (B) in the gradient elution at a flow-rate of 0.25 mL/min. The water/acetonitrile mixture composition was as follows: 0-9 min, water (100%), 9-11 min, water/acetonitrile (40/60, v/v), 11-12 min, water/acetonitrile (29/71, v/v), and 12-25 min, water (100%). UPLC-MS analysis was performed as an independent measurement to determine the percentage of free cyclodextrin in the samples using a Thermo Accela UPLC system (Thermo Fisher Scientific, Waltham, Mass., USA) coupled to a Thermo LTQ Velos mass spectrometer. A lab-made hydrophilic interaction column (2.1×30 mm, 700 nm nonporous silica particles coated with polyacrylamide) was used as the stationary phase. The temperature of the column oven was maintained at 25° C. Stock solutions of HP-β-CD were prepared at different concentrations in the range of 0.05-2 mg/mL in water as calibration standards.

Cell culture rescue study of polyrotaxanes. To assess the therapeutic potential of, among other polyrotaxanes of the various embodiments of the present invention, HP-β-CD:PLURONIC® polyrotaxanes in an appropriate tissue culture model, human NPC2 deficient fibroblast cells (npc2$^{-/-}$) were grown and treated with the polyrotaxanes. Each compound was solubilized in DMSO and diluted in fibroblast cell culture media (MEM/15% FBS/pen/strep) to a concentration yielding the equivalent of 25 μM free HP-β-CD and a final DMSO concentration of 0.001%. The old medium was removed from cells and the media containing each polyrotaxane sample was added before fixing the cells at 30 min, 1.0 h, 3.0 h, and 6.0 h post-treatment. The fixed cells were then stained with 0.05 mg·ml$^{-1}$ Filipin followed by slide preparation. The reduction of cholesterol accumulation was monitored qualitatively by imaging the filipin stain in the cells, and quantitatively by the determination of filipin stain area to total cell area. Results are expressed relative to control untreated cells and are represented as mean±SE (n=3).

Example 1

The synthesis of HP-β-CD:poloxamer polyrotaxanes was performed via the sequence shown in Scheme 2, wherein d, q, n are as defined herein and A, B, C, and C' are as shown.

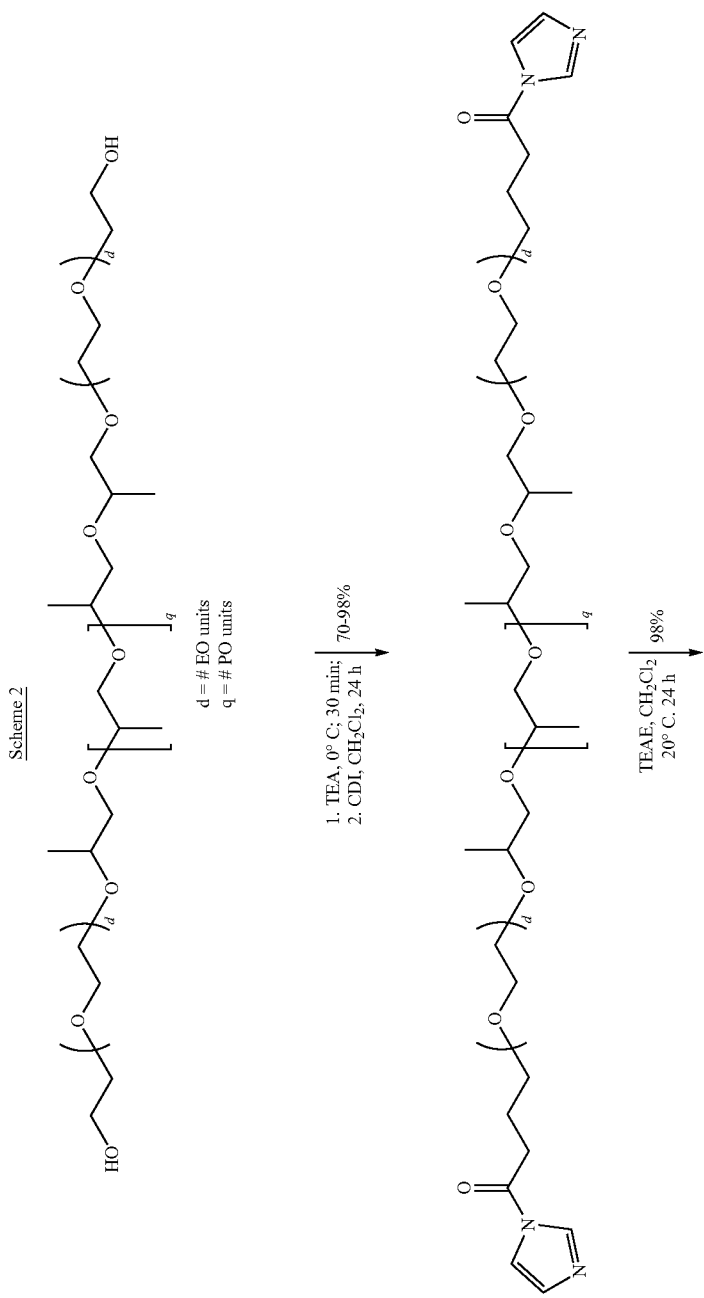

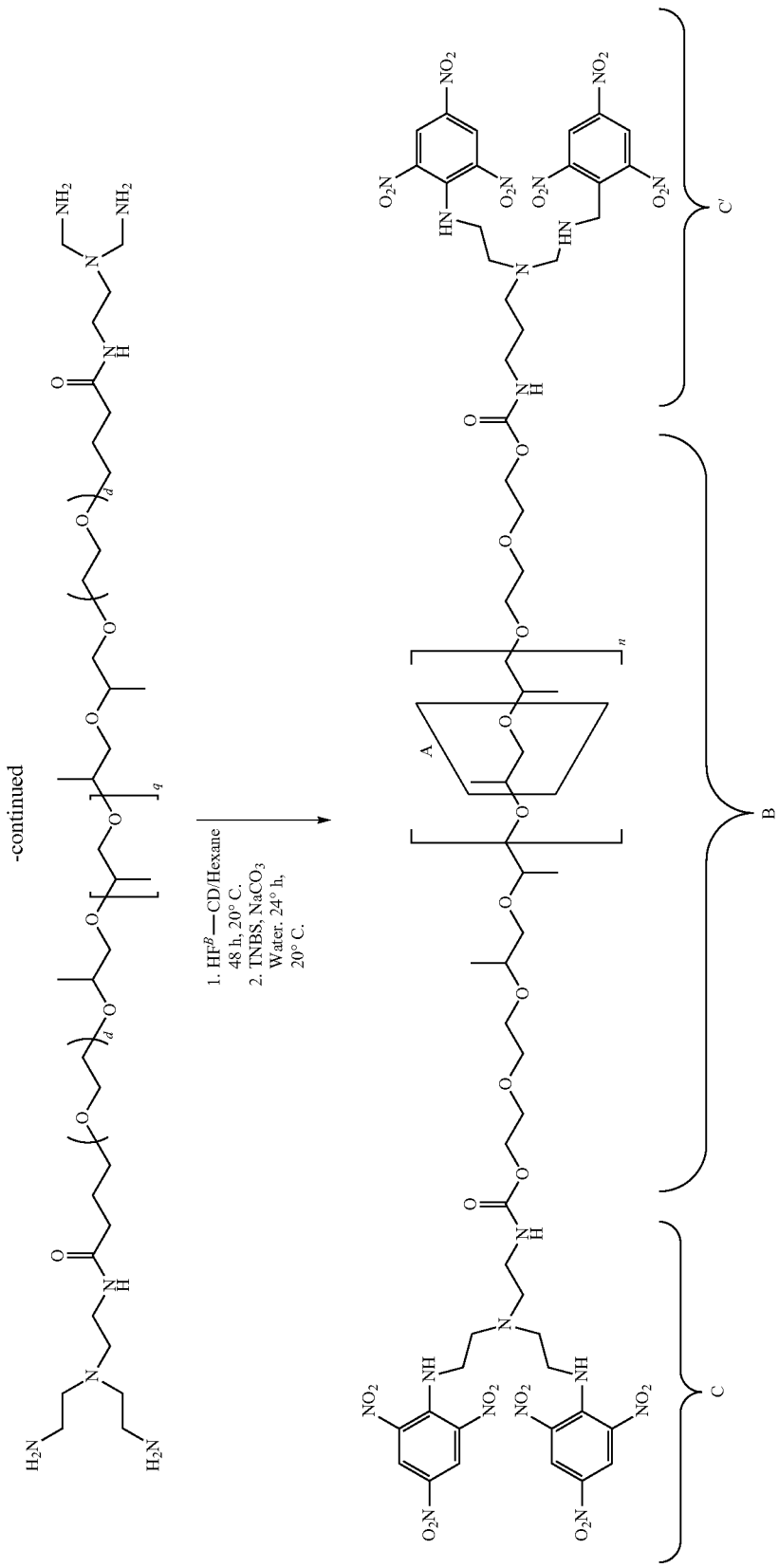

Preparation of a, w-bis-tris(2-aminoethyl)amine PLURONIC® triblock copolymer (TAEA-PLURONIC®). The typical synthetic procedure of the TAEA-PLURONIC® derivatives is described as follows. Dried PLURONIC® copolymer (0.400 mmol) was dissolved in 30 mL dry $CH_2Cl_2$. Triethylamine (1.5 equiv.) was slowly added over 30 min on an ice bath. The mixture was allowed to slowly warm up to 20° C. before addition of excess of CDI (20.0 mmol). This mixture was then stirred under nitrogen for 24 h at 20° C. and concentrated with a rotary evaporator. The product was precipitated in 500 ml ether and filtered in the cases of solid PLURONICs® (F127 and F68). The crude product was washed with ether, filtered, and vacuum dried to afford 70-98% of white powder of a, w-bis-carbonylimidazole PLURONIC® triblock copolymer. In the case of liquid PLURONICs® (L35, L64, L81), the products were washed by centrifugation (8000 rpm, 5 min, 20° C.). The crude CDI-activated PLURONIC® intermediates (3.53 g; 0.276 mmol) were dissolved in 30 mL dry $CH_2Cl_2$ before addition of tris(2-aminoethyl)amine (13.8 mmol). The mixture was then stirred under dried $N_2$ at 20° C. for 24 h. The product was precipitated in 300 mL ether and washed three times with diethyl ether by either centrifugation (liquid PLURONICs®) or filtration (solid PLURONICs®). The final product was dried under a 50 m Hg vacuum for 72 h to yield either white powders or yellow liquids of α,ω-bis-tris (2-aminoethyl)amine PLURONIC® intermediates (PLURONIC®-TAEA). $^1$H NMR ($D_2O$): δ=1.00 ppm (m, $CH_3$ of PPG), 2.60-2.80 ppm (m, 16H, $CH_2$ of TAEA), 3.54-3.65 ppm (m, $CH_2$ of PEG, and PPG, CH of PPG).

Preparation of TNBS-endcapped Polyrotaxanes. General protocol. Dried PLURONIC®-TAEAs (0.04 mmol) and 2-hydroxypropyl-β-cyclodextrin (i.e., ratio of CD:PPG unit=1:2) were dissolved (or suspended) in 15 mL hexane and the mixture vortexed for 3 min before vigorously stirring for 2 h. Then, bath sonication for 30 min at 30° C. followed by 5 min probe sonication (Model W-350, 50 w, ½" probe) were performed to improve the threading efficiency of the PLURONIC® copolymers. The mixture then was stirred for 48 h at 20° C. and shaken on a rocking plate for an additional 24 h before removal of hexane and addition of water to make a slurry solution to which 2,4,6-trinitrobenzenesulfonic acid solution (10% w/v in water, 0.24 mmol) and $NaHCO_3$, (0.24 mmol) were added. The mixture was stirred at 20° C. for 24 h and then mixed an additional 24 h on a rocking plate to allow the products to aggregate and precipitate. The unreacted reagents and unthreaded cyclodextrins were removed by twice dissolving the crude product in 10 mL of methanol and precipitating the product by addition of 500 ml diethyl ether. The product was purified by dialysis using 3,500-14,000 MWCO regenerated cellulose membranes in deionized water for 8 d and dried by lyophilization to generate yellow-orange powders of polyrotaxanes. $^1$H NMR (DMSO-$d_6$): δ=8.7 μm (s, 8H, meta H of phenyl), 5.0 ppm (b, $C_1$—H of CD), 4.0 ppm (t, 4H, phenyl C—NH) 3.5-3.8 ppm (m, $C_{3,5,6}$—H of CD), 2.6-2.8 ppm (m, 16H, $CH_2$ of TAEA) 1.0 ppm (d, $CH_3$ of PPG).

Example 2

The preparation of tris(2-aminothyl)amine-modified poloxamers was achieved by slight modification of the method reported by Li and coworkers. Li, J. et al., *Advanced Materials* 18: 2969-2974 (2006). Organic solvents were evaluated for the threading reaction. Several solvents (3 mL) were used to dissolve 100 mg of PLURONIC® F127-TAEA and HP-β-CD in a 2:1 PPG:CD ratio. The turbid solutions were sequentially bath and probe sonicated, followed by stirring at 20° C. for 48 h. Low boiling solvents (e.g., DCM, methanol, diethyl ether, ethyl acetate, and hexane) were removed under reduced pressure to yield white pseudopolyrotaxane intermediates. Subsequent addition of an excess 2,4,6-trinitrobenzene sulfonate (TNBS) slurry solution in the presence of $NaHCO_3$, followed by stirring of the orange viscous solutions at 20° C. for 24 h, produced endcapped polyrotaxanes that were purified by solvent washing and dialysis. For rotaxanation reactions in higher boiling solvents such as water, DMSO, and DMF, the TNBS endcapping reagent was added directly, followed by a washing and dialysis purification procedure. A summary of the impact of solvent type on the reaction yield of polyrotaxane and corresponding percent coverage of the PLURONIC® PPG block is shown below in Table 1.

TABLE 1

Solvent effect on yield of HP-β-CD:PLURONIC ® F127.

| Solvent | $ε^a$ | mg | No. of $CD^b$ | Coverage ratio (%)$^c$ |
|---|---|---|---|---|
| water | 79 | 2.2 | 0 | 0 |
| $D_2O$ | 78 | 5.2 | 0 | 0 |
| DMSO | 46 | 14 | 0 | 0 |
| DMF | 37 | 39 | 0 | 0 |
| methanol | 33 | 1.4 | 0 | 0 |
| dichloromethane | 9.1 | 6.8 | 1 | 3 |
| Ethyl acetate | 6.0 | 24 | 4 | 12 |
| diethyl ether | 4.2 | 17 | 9 | 28 |
| hexane | 1.9 | 86 | 11 | 34 |

PLURONIC® F127 (Mn 12600, 100 mg), HP-β-CD (Mw 1460, 0.34 g, 1 CD/2 PO units), stirred in solvent (3 mL) for 48 h at 20° C. before addition of TNBS (0.046 mmol, 0.14 mL) and stirring at 20° C. for 24 h. a ε: dielectric constant, b Number of HP-β-CD units threaded, c Determined by 1H NMR integration, based on the ratio of $C_1$—H protons of HP-β-CD and methyl protons of PPG (assuming 1 CD/2 PPG units).

$^1$H NMR spectroscopy analysis was used to determine the number of cyclodextrins "threaded" onto the PLURONIC® axle by comparing integral intensities of the HP-β-CD $C_1$—H (5.05 ppm) and PPG $CH_3$ (1.0 ppm) signals. The coverage ratio was calculated based on the assumption that two PPG units are included per CD unit. Our data show that non-polar solvents such as hexane and diethyl ether promote higher threading efficiencies than water, $D_2O$, methanol, DMSO, or DMF, which show little or no sign of HP-β-CD in the product NMR spectra. It can be inferred from these findings that polar solvents drive the polar cyclodextrins to aggregate through hydrogen bond interactions between the "wide" and "narrow" faces of the toroid, thereby forming hydrophobic tunnels that enable inclusion of the PLURONIC® chains. Additionally, while not being bound by any particular theory, non-polar solvents appear to prevent self-association of the PLURONIC® copolymers by solvating their lipophilic PPG blocks. The polyrotaxane structure, obtained by threading HP-β-CD onto PLURONIC® F127 in hexane solution, was confirmed by $^1$HNMR. A proton peak at ~1.0 ppm is assigned to the PPG methyl groups on the copolymer, whereas proton signals in the 3-3.5 ppm region are attributed to the methylene units ($CH_2$) of the PEG and some of the HP-β-CD protons. A broad signal displayed in the 4.5-5.0 ppm region is assigned to the HP-β-CD $C_1$—H proton as well as the OH-8 proton of the hydroxypropyl cyclodextrin modification. The aromatic TNB proton signals can be observed further downfield in the region of 7-8 ppm. The average number of HP-β-CD units that were threaded onto the PPG block was estimated from the relative intensities of the $^1$H NMR signals attributed to the $C_1$—H, OH-8 HP-β-CD peaks and the PPG/CH$_3$ doublet.

To further confirm the rotaxanation reaction between HP-β-CD and the F127 PLURONIC® axle, two-dimensional-NOESY $^1$H NMR spectra were collected. The inner $C_{3,5}$—H protons of HP-β-CD display a spatial correlation with the PPG methyl groups. This result is consistent with previous reports for β-CD-polymer complexes, suggesting that HP-β-CD molecules were threaded onto the F127 PLURONIC® chains. Furthermore, to prove that the end capping reaction was effective, UV-visible spectroscopy was performed on aqueous solutions (0.5 mg/mL) of HP-β-CD: F127 PLURONIC® polyrotaxane and free TNBS. The absorption maxima of the polyrotaxane complex (ca. 345 nm, 422 nm) differ completely from that of the unreacted TNBS precursor. This finding confirms that the corresponding HP-β-CD:F127 PLURONIC® pseudopolyrotaxane was fully endcapped.

The same reaction conditions in hexane were implemented to prepare polyrotaxanes based on other poloxamers (PLURONIC® copolymers F68, L35, L64, L81, with differing PEG and PPG block lengths). In these cases, 0.04 mmol was used for all the other poloxamers, dissolved in 15 mL of hexane for the threading reaction.

Table 2 summarizes the effect of PPG block size on the percent coverage relative to the maximum theoretical coverage possible for the PPG block. As it can be seen, the threading efficiency is inversely proportional to the hydrophilic-lipophilic balance (HLB) of the poloxamer axle, with high coverages observed for PLURONIC® L81 and PLURONIC® L64. These findings are consistent with our hypothesis that non-polar solvents favor the rotaxanation reaction by promoting interactions between the hydrophobic PPG block and the hydrophobic cavity of the self-associated HP-β-CD monomers. PLURONIC® F127 is an exception to this trend, likely due to the large PEG blocks that flank the PPG core, thereby suppressing the rotaxanation reaction due to weaker hydrophobic interactions between the cyclodextrin cavity and the PEG blocks.

core as determined by $^1$H NMR integration. The free CD values (w/v) were determined by UPLC chromatography using HP-β-CD as standard. The average size and height of the polyrotaxane products were determined from AFM images of the final products. HLB: Hydrophilic-Lipophilic Balance, CAC: critical aggregation concentration, where the values have been adapted from P. Laibinis et al., *J. Coll. Interface. Sci.* 1991, 142, 74, which is incorporated by reference herein in its entirety.

MALDI-TOF MS Analysis of HP-β-CD:poloxamer Polyrotaxanes. MALDI-TOF mass spectrometry was used to determine the distribution of molar masses of the polyrotaxane products formed by the sequence shown in Scheme 2.

NMR spectroscopy and SEC chromatography are the most common methods employed for polyrotaxane characterization, however, analysis of polydimethyl siloxane:cyclodextrin polyrotaxane compositions and molecular weights using MALDI-TOF can also be used. 1:80 polyrotaxane: ILM matrix composition, initially evaluated for HP-β-CD: PLURONIC® F127 polyrotaxane, with the THAP/TMG mixture (1:2 ratio in methanol) was found to produce the best signal-to-noise ratios. The NMR spectra of polyrotaxanes show a range of peaks corresponding to different degrees of HP-β-CD threading ($n_{CD}$). The peak intensity was found to decrease with increasing polyrotaxane m/z values, until the signal was no longer discernible from the base line. For all polyrotaxanes, the observed m/z values corresponded to the sum of TNB-endcapped poloxamer chains+1460×$n_{CD}$. Interestingly, the spectra reveal stepwise increment of mass differing by 1460 Da, corresponding to the molar mass of the HP-β-CD monomer. Furthermore, the most intense ion peak families were in agreement with the values calculated by NMR as summarized in Table 2, however, the spectral profiles show that the polyrotaxane products are polydisperse compounds (MALDI-TOF spectra can be seen in the supporting information).

AFM Imaging of Polyrotaxanes. Using tapping-mode AFM, microstructures of aggregated 100% HP-β-CD polyrotaxanes were observed. All the polyrotaxanes appear as large globular aggregates of different sizes, with average diameters ranging between 47 to 80 nm and heights varying between 0.5-2 nm. These data show that the polyrotaxane molecules cluster into spherical assemblies, presumably due to lateral hydrogen bond interactions between the rotaxanated hydroxypropyl-β-cyclodextrins. The combination of

TABLE 2

Molecular Weight and Purity of Polyrotaxanes

| Polyrotaxane | HLB[a] | CAC(%)[a] | % Free CD (UPLC) | $n_{CD}$ | Threading efficiency | Mw (NMR) | Mw (MALDI) | Average height (nm) | Average size (nm) |
|---|---|---|---|---|---|---|---|---|---|
| 07HP.F127 | 22 | 0.004 | 3.3 | 7 | 22 | 24008 | 24939 | 2.20 | 80 |
| 02HP.F68 | 29 | 0.04 | 0.90 | 2 | 15 | 12458 | 13059 | 1.30 | 50 |
| 04HP.L35 | 19 | 1 | 2.3 | 4 | 44 | 8928 | 8109 | 0.81 | 61 |
| 06HP.L64 | 15 | 0.14 | 6.0 | 6 | 43 | 12848 | 13248 | 1.30 | 70 |
| 11HP.L81 | 2 | 0.0063 | 1.5 | 11 | 52 | 20048 | 17611 | 0.39 | 48 |

In Table 2, and elsewhere herein, the notation nHP.XXX refers to the number n of HP-β-CD molecules that are "threaded" onto a poloxamer "axle," wherein XXX denotes the type of poloxamer "axle."

The threading efficiency was calculated based on a presumed 1 HP-β-CD:2 PO unit ratio. nCD refers to the number of HP-β-CD molecules threaded onto the PLURONIC® low threading efficiencies and flexible, unthreaded PEG ends promotes the aggregation of the hydrophobic PPG-HP-β-CD domains into spherical particles that are surrounded by a PEG corona as reported by Zhang et al. The spherical appearance of these particles suggests that they may possess attractive long-circulation properties in vivo by avoiding their rapid clearance from blood via renal filtration.

Example 3

NPC2$^{-/-}$ Fibroblast Cell Response to Polyrotaxane Exposure. The non-covalent association of HP-β-CD with poloxamer-based polyrotaxanes confers these polymers with the ability to readily dethread the cyclodextrin units from the polymer axles upon removal of the endcapping group due to, e.g., enzymatic activation. Several enzymatic activation schemes have been evaluated recently, however, none have been reported for NPC cells. To investigate polyrotaxanes that will release HP-β-CD upon activation within NPC cells to promote cholesterol solubilization and efflux from the lysosome, the endcap cleavage reaction and dethreading kinetics were investigated of HP-β-CD:poloxamer polyrotaxane complexes that were exposed to buffers of different pHs as a mimic of their response to neutral (pH 7.4) and acidic endosome compartments (pH 5.5). HPLC analysis of F127 based-polyrotaxane (07HP.F127, 2 mg/mL) exposed to either PBS buffer, pH 7.4 or citrate buffer, pH 5.5 at 37° C. revealed that the HP-β-CD: PLURONIC® F127 polyrotaxane is stable toward both mildly acidic and neutral pH conditions. Although this result was encouraging in terms of the stability of the polyrotaxane particles under physiological conditions prior to endocytosis, it suggested that endcap cleavage from the polyrotaxane carrier within acidic late endosomes/lysosomes would be slow under these conditions. Surprisingly, however, treatment of npc2$^{-/-}$ fibroblasts, that have substantial pools of aberrantly stored cholesterol, with polyrotaxanes, produced a substantial and rapid decrease in filipin staining, providing a qualitative indication of cholesterol reduction within these cells. Time-dependent evaluation of filipin staining in these cells provided further evidence of reduced cholesterol accumulation for all the polyrotaxane compounds to levels that were similar to the extent of cholesterol reduction that is produced by 25 μM free HP-β-CD, i.e., 60 to 80% of untreated controls.

While not being bound by any particular theory, this finding suggests that the polyrotaxanes were internalized and dethreaded within the npc2$^{-/-}$ cells, thereby releasing free HP-β-CD that could then mobilize aberrantly stored cholesterol. Based on these findings, it is believed that the TNB group is cleaved from the polyrotaxane by either an enzymatic or reduction reaction occurring within the cells. There is a significant body of data indicating that nitrobenzene substrates are reduced by nitroreductase enzymes that are present in numerous human tissues. While not being bound by any particular theory, based on these findings, and the sequential reduction mechanism of aromatic nitro compounds, it can be inferred that the carbamyl-linked trinitrobenzene endcaps of the polyrotaxanes are reduced to sterically smaller amine substituents that enable the cyclodextrins to slip off the polymer axles. An alternative explanation is that the carbamate linkage attaching the endcap to the polyrotaxane scaffold may serve as a substrate to tyrosinase hydrolysis, thus triggering endcap removal and subsequent dethreading of the polyrotaxane.

Example 4

A polyrotaxane-based Gd$^{3+}$ magnetic resonance (MR) imaging agent constructed from hydroxypropyl-β-cyclodextrin and a poloxamer (e.g., a triblock copolymer such as PEG-PPG-PEG) is described herein. A family of β-CD based polyrotaxanes possessing cleavable carbamate linkages to the polyrotaxane (PRTx) endcap were synthesized, having the formula:

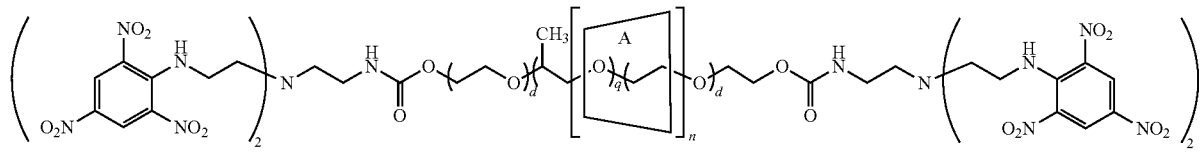

wherein d, q, n, and A are as defined herein.

These compounds have a poloxamer (e.g., a triblock copolymer such as PEG-PPG-PEG) core that has been threaded with either 5-15 copies of β-cyclodextrin (β-CD) (n=5-15) or 3-11 copies of 2-hydroxypropyl-R-cyclodextrin (HP-β-CD) (n=3-11) as shown in Tables 3 and 4:

TABLE 3

| Polymer Base (PLURONIC ®) | n β-CD | % Threading | MW (NMR) | MW (GPC) | MW (AUG) |
|---|---|---|---|---|---|
| F127 | 15 | 71 | 30.8 kD | 33.3 kD | 30.0 |
| F68 | 14 | 100 | 25.5 kD | 28.5 kD | — |
| L64 | 12 | 92 | 11.0 kD | 13.1 kD | — |
| L35 | 5 | 62 | 17.7 kD | 17.1 kD | — |

TABLE 4

| Polymer Base (PLURONIC ®) | n HP-β-CD | % Threading | MW (NMR) |
|---|---|---|---|
| F127 | 11 | 34 | 29.8 kD |
| F68 | 4 | 29 | 15.3 kD |
| L64 | 4 | 27 | 7.5 kD |
| L35 | 3 | 36 | 10.0 kD |
| L81 | 5 | 23 | 11.3 kD |

Also synthesized were compounds of the formula:

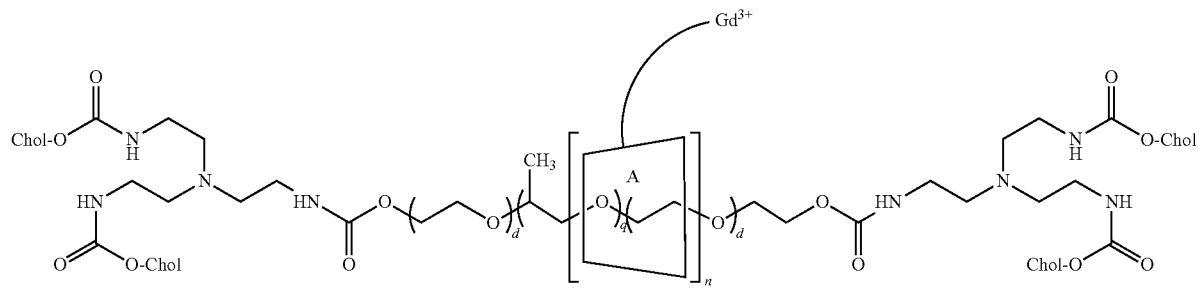

wherein Chol refers to a cholesteryl group; d, q, and n are as defined herein; and

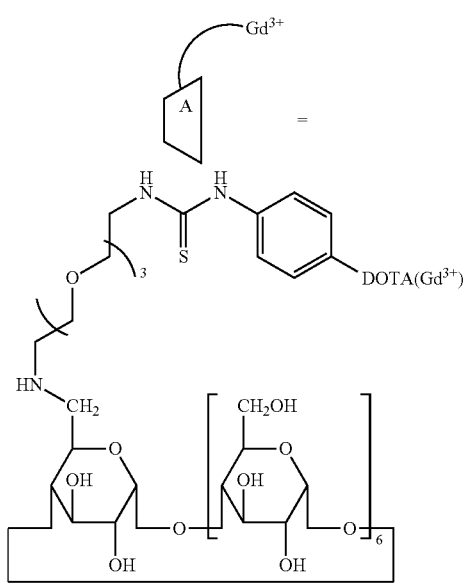

Such compounds are sometimes referred herein as "PRTx-DOTA" and "PRTx-DOTA(Rad)," when the compounds comprise one or more nuclides (Rad) chelated by the DOTA.

Inclusion of the PPG blocks of the poloxamer by HP-β-CD was utilized to construct a polyrotaxane that retains the CD units via bis-carbamylcholesterol endcaps. While not being bound by any particular theory, the polyrotaxanes described herein appear to have a flexible rod-like morphology that can enhance their pharmacokinetics greatly by conferring them with long-circulating properties. Since HP-β-CD is known to form inclusion complexes with the PPG blocks of the poloxamer, this property was utilized to construct a polyrotaxane bearing cholesterol endcaps that were attached via carbamate linkages (HP-β-CD:F127-Chol).

Analysis by $^1$H NMR, 2D Nuclear Overhouser Effect Spectroscopy, and Matrix Assisted Laser Desorption/Ionization Mass Spectrometry (MALDI-MS) indicated that the polyrotaxane carried 15 copies of HP-β-CD, with a molecular weight of 35 kDa and PPG block coverage of ~46%. The polyrotaxane was also analyzed for presence of free HP-β-CD contamination by reverse phase high-pressure liquid chromatography and hydrophilic interaction liquid chromatography; both of these techniques indicated ≤10% free HP-β-CD. The HP-β-CD:F127-Chol was then modified with an excess of oligo(ethylene glycol) via CDI activated coupling to increase the water solubility of the material. Finally, this was conjugated to DOTA-Bn-NCS via a thiocarbamate linkage and then complexed with $Gd^{3+}$ to obtain the final PRTx-DOTA($Gd^{3+}$) with ~14 DOTA($Gd^{3+}$) moieties attached. The AFM images of the samples indicated that the polyrotaxane prepared had a rod-like morphology with lengths in the range of 30-40 nm AFM. Particles with dimensions below 3-7 nm are known to undergo rapid clearance from the bloodstream due to the effective pore size of the glomerular wall being around 8 nm. It was anticipated, therefore, that that the $Gd^{3+}$:DOTA-β-CD:poloxamer PRTx would have a much slower clearance rate from blood than the monomeric $Gd^{3+}$:DOTA-β-CD control due to flow alignment and enlargement of the effective PRTx rod diameter to ~4.6 nm due to the PEG-DOTA grafting.

The synthesized materials were then evaluated in a mouse model to determine their contrast enhancement capabilities. The MRI data reveals that PRTx-DOTA($Gd^{3+}$) had a 2-fold enhancement ratio (ER) in the heart for as long as 30 min. On the contrary, the ER of the control β-CD-DOTA($Gd^{3+}$) dropped from 1.5 to 1 over a period of 30 min. Furthermore, the MRI data also indicated that the ER observed in the kidney with the PRTx-DOTA($Gd^{3+}$) dropped from 2 to 1.6 over a period of 30 min, while that observed with the control β-CD-DOTA($Gd^{3+}$) dropped rapidly from 1.9 to 1.1 over a period of 30 min, indicating rapid renal filtration of the control. The superior MR contrast of the PRTx-DOTA ($Gd^{3+}$) in the heart at 30 min as compared to the control further confirmed the improved pharmacokinetics of the polyrotaxane. The increased molecular weight and dimensions of the β-CD constructs reduces their rate of kidney filtration due to the EPR effect after modification with $Gd^{3+}$:DOTA, leading to a substantially longer circulation half-life and enhancement ratios in mice for the polyrotaxane scaffold compared to the HP-β-CD monomer control. Furthermore, the polyrotaxanes were cleared through the bladder and no acute toxicity was observed. Exposure of Niemann-Pick Type $C_2$-/- fibroblasts to the parent β-CD:poloxamer PRTx compound (i.e., prior to DOTA activation and $Gd^{3+}$ loading) reveals that the carbamyl-endcapped polyrotaxane structures remain intact in serum-supplemented media until they are trafficked to the LE/LY compartment, where the β-CD units are liberated from the polymer backbone via either pH- or enzyme-induced removal of the PRTx endcaps. While not being bound by any particular theory, these findings suggest that the PRTx may be excreted as an intact species. Further, these results taken together suggest that the PRTx-DOTA($Gd^{3+}$) can be potential agents for vascular enhancement due to their lack of acute toxicity and long-circulating properties.

Example 5

A library of β-CD:Pluronic polyrotaxane (PR) compounds was prepared by thoroughly mixing 4-sulfobutylether-β-cyclodextrin (SBE-β-CD) with the desired second β-CD derivative in the solid state by extensive grinding together of the two β-CD powders before initiating the polymer threading and endcapping reactions. The pseudopolyrotaxane intermediates generated by this procedure were endcapped with cholesterol chloroformate to generate the corresponding PR product as depicted in Scheme 3. $^1$H NMR analysis was used to determine the number of β-CD units threaded onto the Pluronic axle by comparing the integral intensities of the HP-β-CD C1-H (5.05 ppm) and PPG $CH_3$ (1.0 ppm) signals. For compounds containing SBE-β-CD, the broad peak of the sulfobutyl $CH_2$ moiety at 1.7 ppm was used to determine the number of SBE-β-CD units incorporated. The coverage ratio was calculated based on the assumption that two PPG units are included per CD unit. The estimated number of total β-CD units threaded onto each copolymer and the percent β-CD coverage of samples corresponding to Pluronic L81 PR obtained from β-CD, HP-β-CD, Me-β-CD, and azido-β-CD alone or as mixed β-CD species are shown in Table 5.

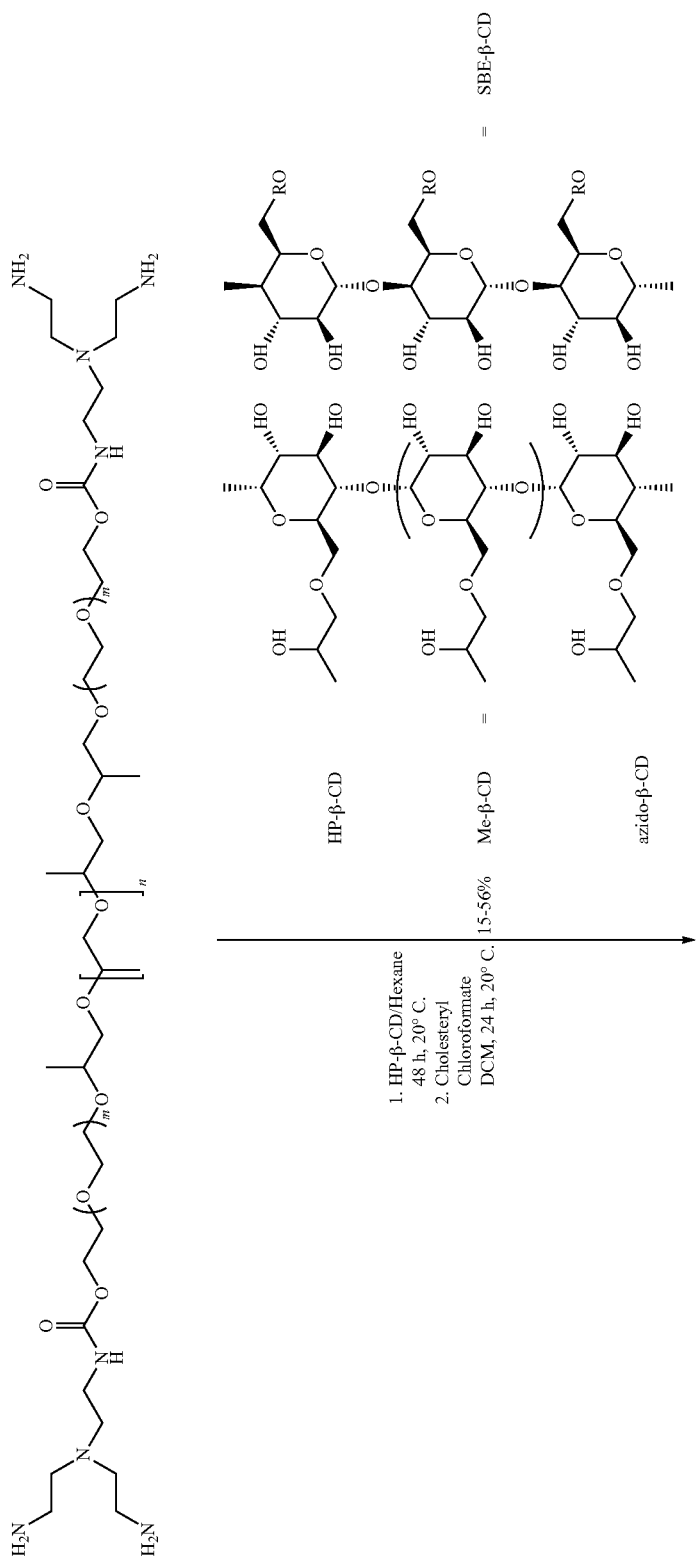

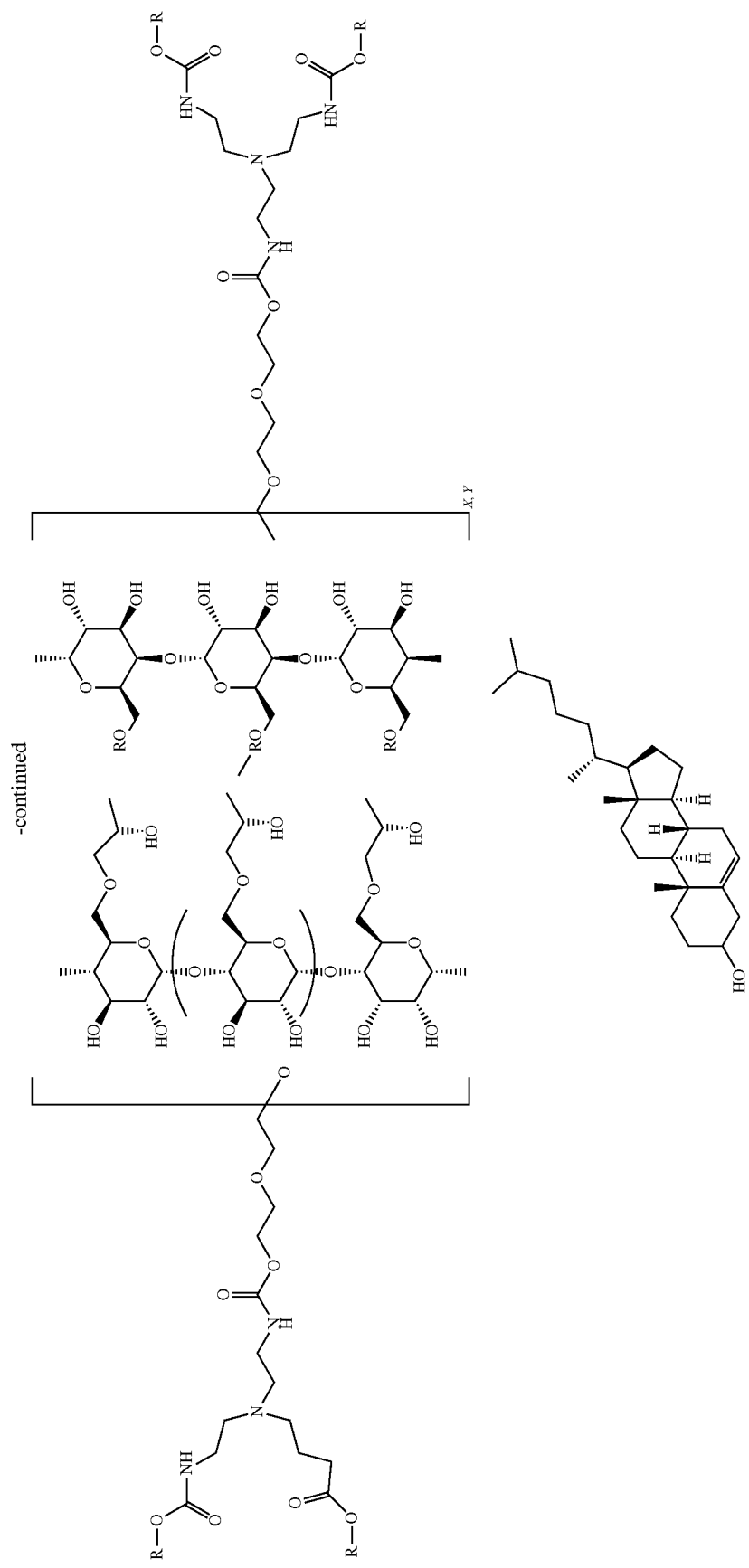

TABLE 5

| Pluronic L81-based PR | βCD/SBE-β-CD Composition[a] | | Coverage[a] | | PR Yield[b] (%) | Molecular weight | |
|---|---|---|---|---|---|---|---|
| | Feed ratio | Total CD Found | Tot CD (%) | SBE-βCD (%) | | $M_w$, NMR | $M_w$, GPC[c] |
| β-CD-PR | 100 | 18 | 82 | — | 44 | $2.60 \times 10^4$ | $8.03 \times 10^4$ |
| HP-β-CD-PR | | 11 | 50 | — | 13 | $2.17 \times 10^4$ | $3.60 \times 10^4$ |
| Me-β-CD-PR | 100 | 8 | 36 | — | 20 | $1.61 \times 10^4$ | $1.70 \times 10^4$ |
| azido-β-CD-PR | 100 | 8 | 36 | — | 25 | $1.49 \times 10^4$ | $2.26 \times 10^4$ |
| β-CD/SBE-βCD-PR | 50:50 | 21 | 95 | 41 | 35 | $3.70 \times 10^4$ | $5.40 \times 10^4$ |
| HP-β-CD/SBE-β-CD-PR | 50:50 | 19 | 86 | 46 | 37 | $3.85 \times 10^4$ | $1.50 \times 10^4$ |
| Me-β-CD/SBE-β-CD-PR | 50:50 | 19 | 86 | 64 | 27 | $4.00 \times 10^4$ | $1.16 \times 10^4$ |
| azido-β-CD/SBE-β-CD-PR | 50:50 | 18 | 82 | 64 | 35 | $3.91 \times 10^4$ | $5.19 \times 10^4$ |
| SBE-β-CD-PR | 100 | 21 | 95 | 100 | 63 | $4.72 \times 10^4$ | NA |

The molecular weights of the PR estimated by $^1$H NMR analysis products were then compared with GPC-MALS/RI results using DMSO as eluent (Table 5). The molecular weights determined by GPC analysis are in general agreement with the values calculated from NMR except for β-CD/PR, which appears to be self-aggregating in DMSO based on the appearance of a very high MW peak in the GPC chromatogram.

To assess the role of 0-CD competition in the mixed rotaxanation reaction, binary mixtures containing β-CD, HP-β-CD, Me-β-CD, or Azido-β-CD mixed with SBE-β-CD, were prepared at different molar ratios starting with 0% SBE-β-CD. Solid mixtures of the β-CD were suspended in hexane such that the Pluronic L81 copolymer was afforded ready access to both β-CD hosts in the mixture. When the percent threading efficiency of each β-CD pair is plotted against the percent molar ratio of SBE-β-CD in the reaction feed, the threading efficiency of the uncharged β-CD derivatives remains roughly constant while the amount of SBE-β-CD threaded onto the polymer axle increases with increasing feed ratio. While not being bound by any specific theory, it is believed that since the structural modifications of the β-CD derivatives can vary significantly across the β-CD derivatives described herein, the CD-entrapped hexane solvent is more readily displaced from the SBE-β-CD cavity by the PEG ends of the polymer strand than the cavities of the other less polar, non-ionic β-CD derivatives.

FTIR was used to analyze the PR compounds; these spectra were compared to those of the pure β-CD monomeric precursors and the Pluronic L81 precursor. The peak corresponding to the cholesterol endcap carbamate appears at 1672 cm$^{-1}$ and the C—O—C and C—N—C stretching vibrations of carbonyl group in carbamate linkage emerge at 1109 cm$^{-1}$ and 1230 cm$^{-1}$, respectively, for all PR. The broad absorption between 3100-3500 cm$^{-1}$ corresponds to the CD hydroxyl stretching vibrations. A strong peak at 2103 cm$^{-1}$ was also observed in the Azido-β-CD:Pluronic L81 PR and Azido-β-CD/SBE-β-CD:Pluronic L81 PR compounds, corresponding to the azide stretching mode, indicating that the PR isolated from these reactions has significant Azido-β-CD content.

PR product structures were further characterized using wide-angle X-ray scattering (WAXS). A unique peak is observed near 2θ=20°; this peak is different from those found in the corresponding pure β-CD or Pluronic L81. Amorphous HP-β-CD, Me-β-CD, SBE-β-CD, and β-CD samples show peaks at 12.04°, 14.36°, 18.24°, and 21.76°. Taken together, these data suggest the presence of a channel-type crystalline structure for all β-CD PR generated in this study, similar to the channel-like structures that were previously reported in the literature.

Pluronic inclusion within the β-CD units was further supported by differential scanning calorimetry (DSC) analysis. The DSC thermograms of pure β-CD (except Azido-β-CD), as well as the unmodified Pluronic L81 polymer, do not produce any significant endothermic transitions. This is likely due to disordering of the β-CD microcrystalline powder during the first heating phase, producing an amorphous solid that has no melting transitions. For Azido-β-CD, the peak at 140° C. can be attributed to N$_2$ extrusion. On the other hand, clear endothermic transitions are observed for the PR. This corresponds to the aggregation of rod-like segments of the nearest neighbor PR species into microcrystalline domains that melt at elevated temperatures. Enthalpy exchanges corresponding to all SBE-β-CD-based PR appear to be smaller than those of single CD and mixed PR materials. It is possible that the charge repulsion caused by the SBE-β-CD sulfonate groups prevents these macromolecules from packing into ordered structures.

PR thermal stability was also evaluated by thermal gravimetric analysis (TGA). The pure β-CD, with the exception of Azido-β-CD and SBE-β-CD, had a single thermal decomposition event. Azido-β-CD produces a different profile with a sharp weight loss at 440° C. indicating the decomposition of the azide group and loss of N$_{2(g)}$ from the CD. The multiple weight losses seen for SBE-β-CD are likely due to dehydration, extrusion and/or cracking (e.g. loss of H$_2$O, SO$_2$ and butanesultone) processes of the β-CD modifications.

The PR thermograms showed two or more steps in the thermal degradation process. The first step is attributed to the thermal decomposition of the corresponding cyclodextrins, while the second one is related to the Pluronic L81 copolymer degradation. Apparently, the weight losses of the inclusion polymer complexes are slower than those for the free β-CD, suggesting that the β-CD bound to the PPG block confer greater thermal stability for the β-CD than the monomeric CDs species. In addition, the decomposition temperatures of the Pluronic L81 during the second phase of PR degradation increases relative to that of the free polymer. One can infer from these observations, without being bound by any specific theory, that inclusion of the PPG chains within the CD cavities affords greater thermal stability for the copolymer by dampening out thermally-induced polymer segment vibrations via PPG-O-CD wall collisions. These findings, i.e., that the thermal stability of both the β-CD species and the Pluronic L81 triblock copolymer are increased upon rotaxanation, suggest that the polymer is included within the hydrophobic β-CD cavity.

Using negative-stain TEM microscopy, microstructures of the PR dispersions are observed. TEM micrographs were obtained for HP-β-CD:Pluronic L81 PR and HP-β-CD/SBE-β-CD:Pluronic L81 PR, which were chosen as models for all PR prepared. Both compounds show self-aggregation to produce spherical particles. HP-β-CD:Pluronic L81 PR gave rise to nanoparticles with diameters of 10-88 nm, whereas under the same conditions, HP-β-CD/SBE-β-CD:Pluronic L81 PR aggregated into more regular and small particles that were 6-12 nm in diameter. While not being bound by any specific theory, the net difference seen between these two samples can be explained by electrostatic charge repulsion between the sulfonated CDs, thereby preventing more extensive aggregation of the PR in the case of HP-β-CD/SBE-β-CD:Pluronic L81 PR.

Experiments were conducted to test whether the solubilities of HP-β-CD PR is sufficiently improved to enable screening studies in Niemann Pick Type C cells. The negative charges introduced by the SBE-β-CD units in the PR complexes are believed to reduce their aggregation and improve their water solubility. To test this assumption, the samples obtained from HP-β-CD/SBE-β-CD mixtures were dissolved in nanopure water and the appearance of the solutions monitored. It was found that increasing the amount of SBE-β-CD in the PR structure leads to a significant improvement in their water solubility, particularly for the samples with SBE-β-CD molar ratios of ≥25%. It is well known that CD-based PR are generally insoluble in water due to the aggregation of their rod-like structures. The incorporation of SBE-β-CD, a highly water soluble material, leads to weaker intermolecular interactions and improved water solubilities of the mixed PR products.

Since SBE-β-CD incorporation significantly increases PR solubility, experiments were conducted to determine whether PR with mixed β-CD compositions were also biologically active in an in vitro model of Niemann-Pick Type C disease. PR carrying an increasing percentage of SBE-β-CD were administered to Niemann-Pick C1-deficient (npc1−/−) fibroblasts to examine their ability to mobilize cholesterol from sites of aberrant accumulation. Each PR family member, generated with a 0%, 30%, 50%, 60%, or 100% SBE-β-CD feed ratio, was administered at a total β-CD concentration of 25 µM and compared to administration of 25 µM SBE-β-CD or HP-β-CD monomers as controls. Comparisons were made at equivalent β-CD concentrations in these experiments, such that each PR construct carrying 10 copies of β-CD was administered at a 10-fold lower molar concentration than for the β-CD monomer controls, so that any apparent differences in cholesterol mobilization could be attributed to the PR agent (a type of β-CD prodrug) rather than the total drug concentration added to the cells.

Analysis of cholesterol mobilization 6 h after treatment revealed that these PR family members perform roughly equivalently to their respective monomers in cholesterol mobilization assays. HP-β-CD and SBE-β-CD monomers decreased the average filipin staining in npc1−/− fibroblasts to approximately 75% of the untreated control levels after 6 h. PR comprised of 100% HP-β-CD and 100% SBE-β-CD performed equivalently, each decreasing filipin staining to ~78% of control. PRs carrying 30:70 SBE-β-CD:HP-β-CD ratio decreased fluorescence to ~65% of the untreated group. PR carrying either a 50:50 or 60:40 SBE-β-CD:HP-β-CD drug load were less effective, decreasing fluorescence to 86% and 83%, respectively. A broader screen of PR concentrations would be necessary to determine if incorporation of low SBE-β-CD ratios (e.g., 30%) is able to significantly improve cholesterol efflux relative to β-CD monomers or PR with higher SBE-β-CD percentages. DMSO control experiments showed no effect of DMSO treatment on filipin staining. These experiments clearly show that PRs generated from mixed threading reactions retain their cholesterol mobilization activity in vitro.

In summary, these experiments represent an efficient synthetic method for the construction of mixed β-CD based PR using a heterogeneous strategy. Competition between S-CD monomers during the rotaxanation reaction is likely dictated by a balance between electrostatic repulsion between neighboring SBE-β-CD units, the intermolecular hydrogen bonding capability of the various β-CD derivatives, and their relative solubilities in the organic solvent used during the heterogeneous threading reaction. A cooperative threading process of the β-CD during the rotaxanation reaction is inferred, leading to threading of mixed CDs on the polymer core. Rotaxanation of SBE-β-CD increased as a function of its increasing molar ratio in the feed. Interestingly, the water solubilities of the PR were significantly improved due to the presence of SBE-β-CD units in the PR product. Incorporation of SBE-β-CD within the PR scaffold does not significantly affect their ability to mobilize aberrantly stored cholesterol relative to monomeric β-CD controls. The synthesis of water soluble PR with defined units of azide may open possibilities for controlled and orthogonal post-modifications for a wide variety of applications, including a more easily administered and retained form of R-CD derivatives for improved Niemann-Pick Type C therapeutics.

Example 6

Synthesis of HP-β-CD and SBE-β-CD based Polyrotaxanes Contrast Agents ($Gd^{3+}$-HP-β-CD/SBE-β-CD-PR). The schematic approaches used to synthesize the polyrotaxane contrast agents are depicted in Scheme 4.

Scheme 4
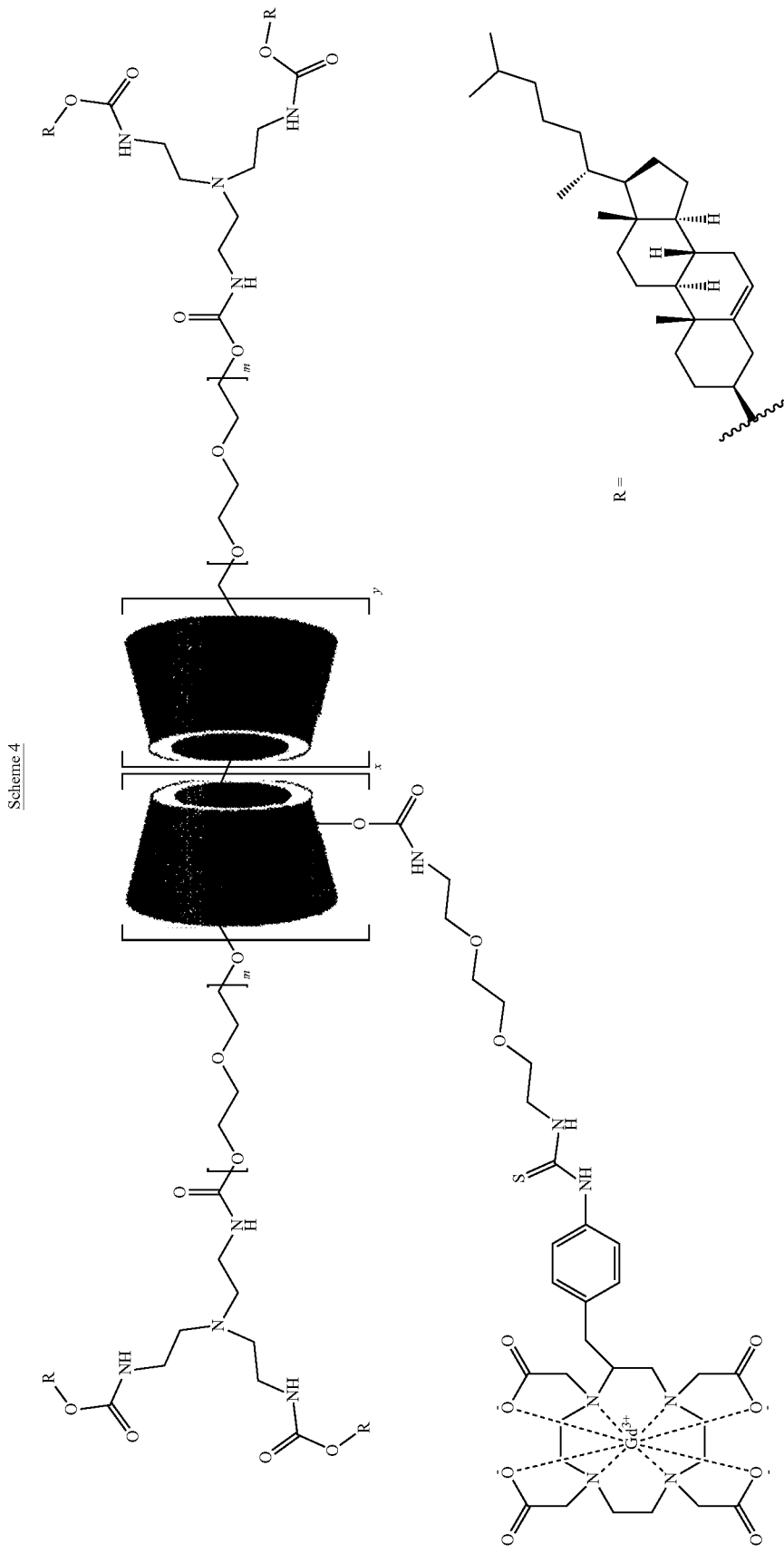

First, the synthesis of a family of HP-β-CD/SBE-β-CD: Pluronic® polyrotaxanes was performed according to previously reported procedures in heterogeneous conditions. Five Pluronic® copolymers including F-127, F-68, L-35, L-64, L-81 were considered based on the size as well as the polyethylene oxide (PEG) and polypropylene oxide (PPG) blocks of the polymers. Compounds were prepared by thoroughly mixing SBE-β-CD and the HP-β-CD with a molar ratio of 30% of SBE-β-CD in their solid state by extensive grinding the two cyclodextrins into finely powdered mixture before initiating the polymer threading and endcapping reactions using hexane as solvent. The pseudopolyrotaxane intermediates generated by this procedure were endcapped through carbamate linker with cholesterol chloroformate to generate the corresponding polyrotaxane products. $^1$H NMR spectroscopy analysis was used to quantify the number of cyclodextrins threaded onto the Pluronic® axles by comparing the integral intensities of the cyclodextrins, HP-β-CD $C_1$—H (4.5-5.0 ppm) and HP-β-CD (1.6 ppm), and PPG $CH_3$ (1.0 ppm) of Pluronic® signals. The coverage ratio was calculated based on the assumption that one CD molecule was capable of inclusion of two PPG units in its cavity. The proton peak at ~1.0 ppm is assigned to the PPG methyl groups on the copolymer, whereas the proton signals in the 3-3.5 ppm region are attributed to the methylene units ($CH_2$) of the PEG and some of the HP-β-CD protons. The broad signal displayed in the 4.5-5.0 ppm region is assigned to the cyclodextrins $C_1$—H proton. The broadening of peaks in this region confirms that the Pluronic® copolymers were successfully threaded with the cyclodextrins. Table 6 summarizes the number of CDs held by each Pluronic® axles, the percent coverage as well as the percent amount of SBE-β-CD contained in the molecules. The efficiency of threading tends to improve with polymers having high ratio of PPG to PEG units. This can be seen with L-35, L-64, and L-81 with PPG/PEG ratio of 0.72, 1.2, and 7.2 respectively. The proportions of the cyclodextrins in the polyrotaxanes seems to be controlled across the compounds in the range of 40 to 50% SBE-β-CD. The HP-β-CD/SBE-β-CD:Pluronic® PR intermediates were then activated with CDI before modification with an excess of 1,8-diamino-3,6-oxo-octane to increase the water solubility of the materials and incorporate amine functionality for further chemical conjugations. Finally, the DADO-HP-β-CD/SBE-β-CD-PR intermediate were coupled with DO3A-Bn-SCN and then treated with $GdCl_3$ to obtain the final $Gd^{3+}$—HP-β-CD/SBE-β-CD-PR with different DO3A chelator attached as determined by $^1$H NMR (Table 6).

TABLE 6

Summary of number and coverage of CDs of $Gd^{3+}$-HP-β-CD/SBE-β-CD based polyrotaxanes contrast agents.

| Polyrotaxane | # of CDs [a] | # of HPβCD [a] | # of SBEβCD [a] | % CD Coverage | # of DO3A [b] |
|---|---|---|---|---|---|
| $Gd^{3+}$-HPβCD/SBEβCD-F127 | 10 | 6 | 4 | 31 | 12 |
| $Gd^{3+}$-HPβCD/SBEβCD-F68 | 5 | 3 | 2 | 38 | 15 |
| $Gd^{3+}$-HPβCD/SBEβCD-L35 | 16 | 10 | 6 | 100 | 14 |

TABLE 6-continued

Summary of number and coverage of CDs of $Gd^{3+}$-HP-β-CD/SBE-β-CD based polyrotaxanes contrast agents.

| Polyrotaxane | # of CDs [a] | # of HPβCD [a] | # of SBEβCD [a] | % CD Coverage | # of DO3A [b] |
|---|---|---|---|---|---|
| $Gd^{3+}$-HPβCD/SBEβCD-L64 | 11 | 6 | 5 | 73 | 22 |
| $Gd^{3+}$-HPβCD/SBEβCD-L81 | 20 | 10 | 10 | 91 | 22 |

[a] Determined by $^1$H NMR.
[b] Estimated using NMR integration of the phenyl protons of DOTA normalized with PPG methyl protons.

The molecular weights of the compounds were estimated by $^1$H NMR analysis, GPC-MALS/RI, and Analytical Ultracentrifugation Analysis (AUC) with DMSO as eluent was used for comparison (Table 7).

TABLE 7

Average molecular weight of $Gd^{3+}$-DOTA-HP-β-CD/SBE-β-CD polyrotaxanes.

| Polyrotaxane | Mw (NMR) | Mw (GPC) | Mw (AUG) | # of DO3A [a] | % Gd Content [b] |
|---|---|---|---|---|---|
| $Gd^{3+}$-HPβCD/SBEβCD-F127 | 39251 | 34120 | 33300 | 12 | 4.5 |
| $Gd^{3+}$-HPβCD/SBEβCD-F68 | 29529 | 24770 | 11800 | 15 | 11 |
| $Gd^{3+}$-HPβCD/SBEβCD-L35 | 40232 | 52630 | 29100 | 14 | 6.2 |
| $Gd^{3+}$-HPβCD/SBEβCD-L64 | 39065 | 30610 | 11800 | 22 | 8.0 |
| $Gd^{3+}$-HPβCD/SBEβCD-L81 | 54705 | 49430 | — | 22 | 5.2 |

[a] Estimated using NMR integration of the phenyl protons of DOTA normalized with PPG methyl protons.
[b] ICP-MS analysis.

The relative molecular weights determined by GPC analysis are in general agreement with the values calculated from the NMR while the AUC values are lower for most of the compounds. This can be explained by the centrifugation sample preparation used to circumvent the solubility issues. Since the polyrotaxanes are highly polydisperse, the supernatants considered for the AUC analysis presumably content low molecular weight polyrotaxane molecules. In Table 7, the weight percentage of Gd contents in the samples, evaluated with ICP-MS analysis are indicated. These values are relatively low presumably due to the loss of Gd during the dialysis purification that required to maintain the pH of the water at 7 for several days. The physical properties of the samples were characterized with DLS analysis (Table 8).

TABLE 8

Hydrodynamic diameters and zeta-potentials $Gd^{3+}$-DOTA-HP-β-CD/SBE-β-CD polyrotaxanes.

| Polyrotaxane | Size (nm) | PDI | ζ-Potential (v) |
|---|---|---|---|
| $Gd^{3+}$-HPβCD/SBEβCD-F127 | 230 | 0.46 | −3.5 |
| $Gd^{3+}$-HPβCD/SBEβCD-F68 | 138 | 0.49 | −13 |
| $Gd^{3+}$-HPβCD/SBEβCD-L35 | 116 | 1.0 | −6.0 |

TABLE 8-continued

Hydrodynamic diameters and zeta-potentials Gd$^{3+}$-DOTA-HP-β-CD/SBE-β-CD polyrotaxanes.

| Polyrotaxane | Size (nm) | PDI | ζ-Potential (v) |
|---|---|---|---|
| Gd$^{3+}$-HPβCD/SBEβCD-L64 | 120 | 0.40 | −9.4 |
| Gd$^{3+}$-HPβCD/SBEβCD-L81 | 173 | 1.0 | −11 |

The hydrodynamic diameters of the compounds dissolved in water are in the range of 116 to 140 nm except for Gd$^{3+}$—HP-β-CD/SBE-β-CD-F127 and Gd$^{3+}$—HP-β-CD/SBE-β-CD-L64 that probably underwent aggregation. The DLS data also revealed that the compounds are widely polydisperse as it was observed before in our previous works. The zeta-potential measurements indicated that the polyrotaxanes contrast agents are slightly negatively charged due to the sulfonate negative charge of SBE-β-CD improving significantly water solubility of the compounds.

Molar Relaxitivity of Gd$^{3+}$-HP-β-CD/SBE-β-CD-PRs. The proton nuclear magnetic relaxation dispersion ($^1$H NMRD) was utilized to measure the T$_1$ relaxivity of the polyrotaxane contrast agents. This technique is a non-destructive low-field magnetic method usually used to collect molecular dynamics of a substance through measurement of the nuclear spin-lattice constant 1/T$_1$ over a range of magnetic field strengths. The profiles obtained at 30° C. covering 30 values of magnetic fields from 0.24 mT to 0.97 T from all the compounds, except for Gd$^{3+}$—HP-β-CD/SBE-β-CD-L64, dissolved in non-deuterated are depicted in FIG. 1 and show a slight increases from 20 MHz to 40 MHz for all the compounds. This level off of the curves of r$_1$ around 30 MHz is characteristic of macromolecular contrast agents such as dendrimers that show an NMRD maximum of profiles around this region. Gd(III) chelate monomers such as DOTAREM® and Prohance® have $^1$H NMRD profiles that do not show any increment or maximum in the same regions. The lowest and highest relaxivities were observed for Gd$^{3+}$—HP-β-CD/SBE-β-CD-F68 (12.2 mM$^{-s}$s$^{-1}$, 40 MHz) and Gd$^{3+}$—HP-β-CD/SBE-β-CD-L35 (6.7 mM$^{-1}$s$^{-1}$, 40 MHz). These values are relatively low compared to those of dendrimers. This can be explained by the high flexibility, i.e. free rotation and translation of CDs around the polymers axle of the polyrotaxane constructs, which induces a long residence time, τ$_M$. Generally, the residence time should be reasonably short in order to increase the relaxivity of macromolecules. In addition, the rotational time, τ$_R$ of these flexible structures are expected to be short leading to lower relaxivity when compared to rigid nanoparticles such as dendrimers that have a compact structure that imposes isotropic rotational dynamic restrictions and therefore, increasing r$_R$. Measurement of the relaxivity of the polyrotaxane contrast agents at discrete higher fields (1.5 T or clinical field, 3 T) is necessary to assess their MR imaging properties.

Figure 2:
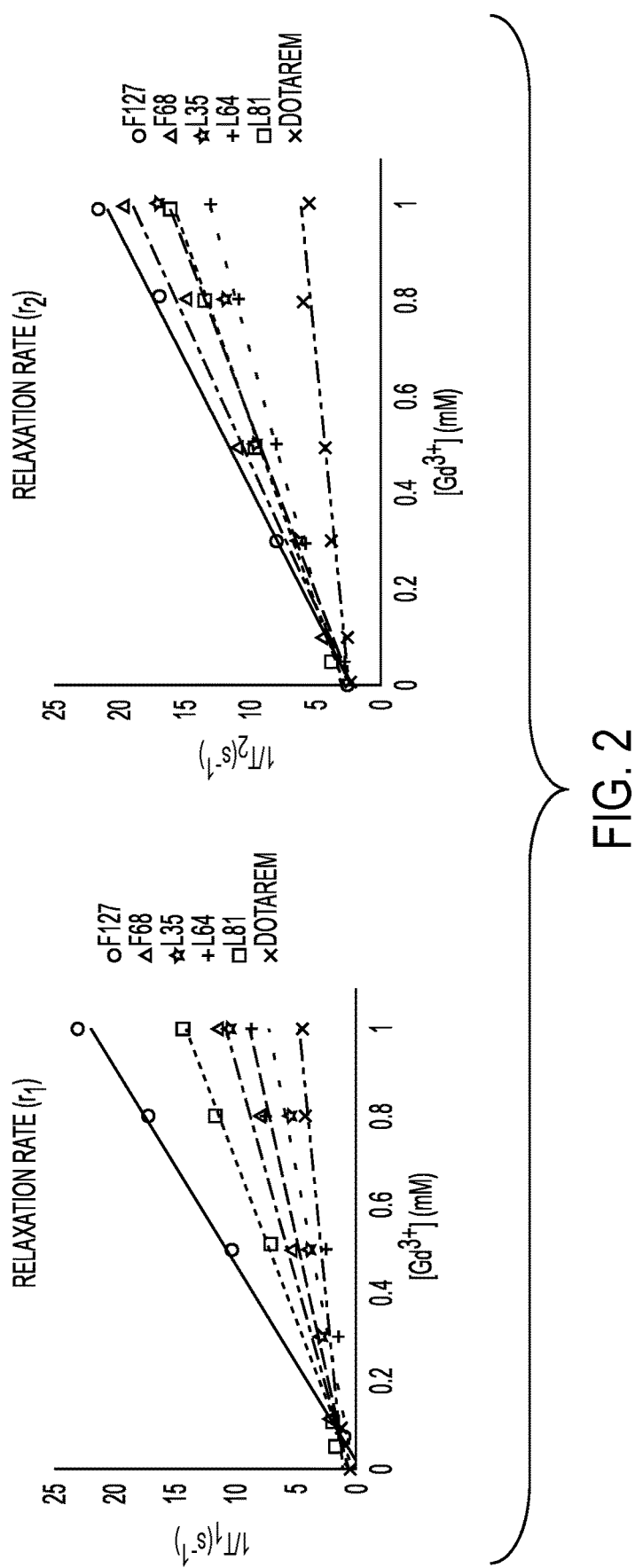
FIG. 2 is a plot of showing the relaxivity determination of $Gd^{3+}$-HP-β-CD/SBE-β-CD based polyrotaxanes and DOTAREM® at 7 T, 25° C.
Figure 3A:
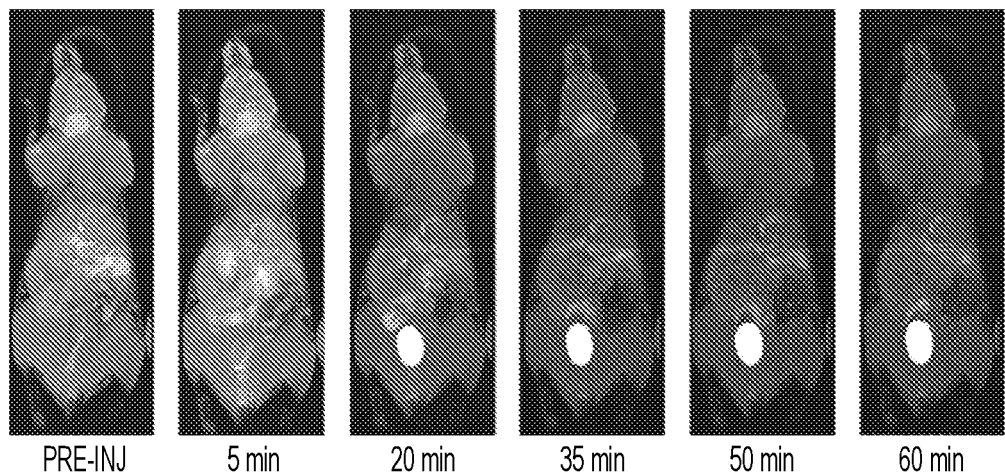
FIGS. 3A-3E are 3D-MR images of polyrotaxanes. A: DOTAREM, B: $Gd^{3+}$—HP-β-CD/SBE-β-CD-F127, C: $Gd^{3+}$—HP-β-CD/SBE-β-CD-F68, D: $Gd^{3+}$—HP-β-CD/SBE-β-CD-L35, E: $Gd^{3+}$—HP-β-CD/SBE-β-CD-L81. Images were recorded with Bruker 7 T.
Figure 3B:
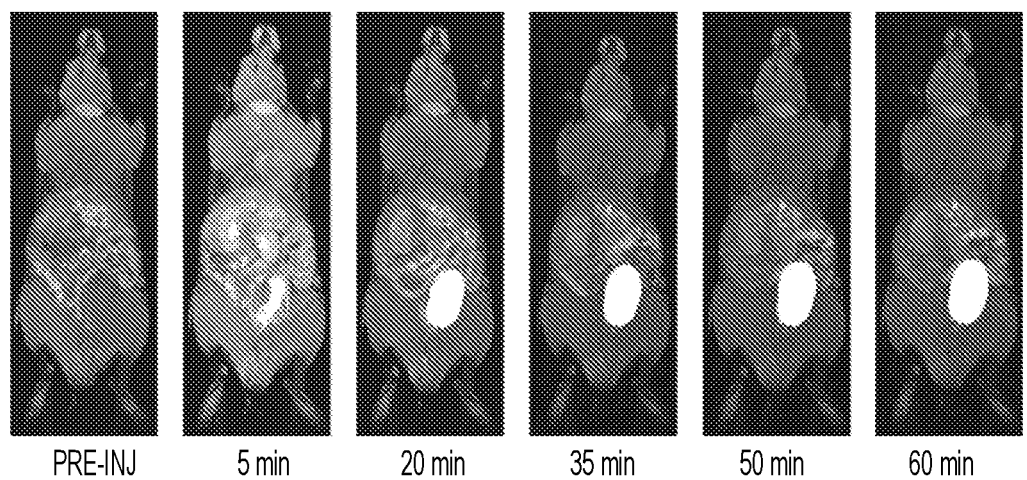
Figure 3C:
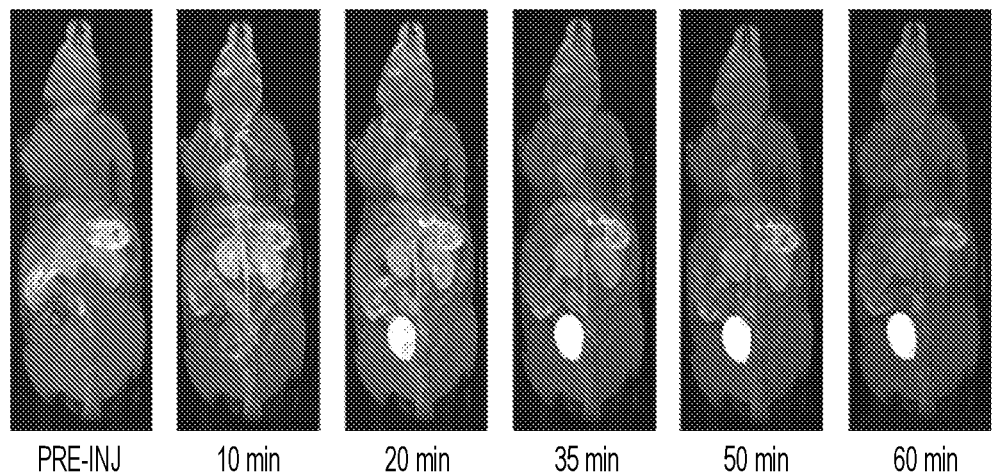
Figure 3D:
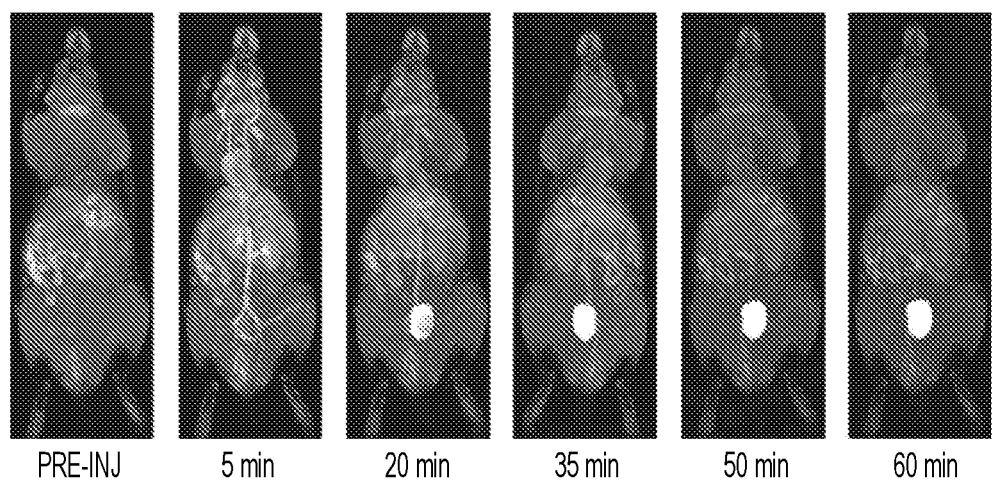
Figure 3E:
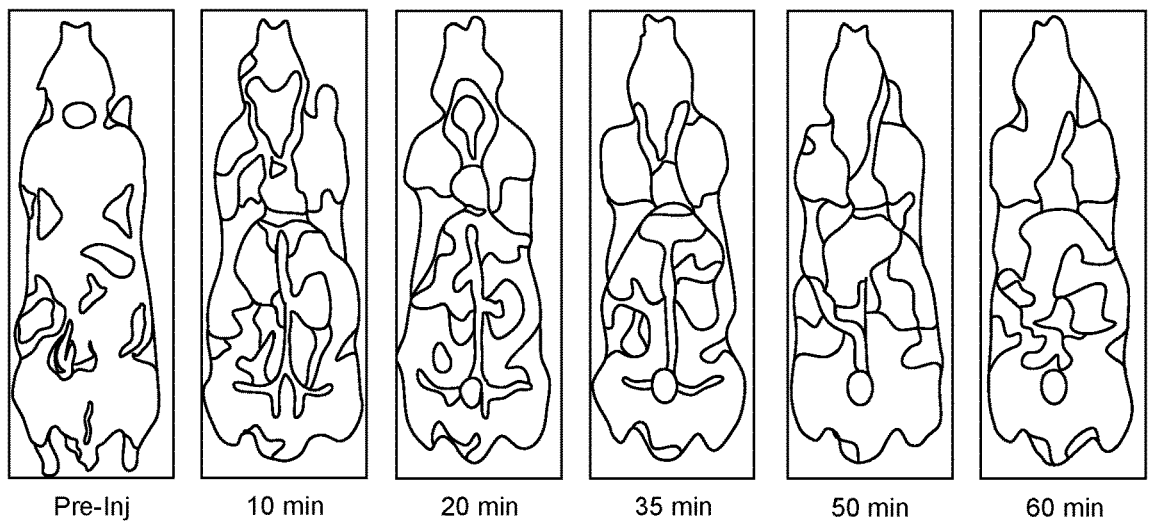

A fixed field measurement of relaxivity was also performed on aqueous solutions of the polyrotaxane contrast agents in the range of 0.05 to 1.0 mM using a 7 T (261 MHz) Bruker BioSpec scanner at 23° C. The relaxivity r$_1$ and r$_2$ were determined by plotting the inverse longitudinal (1/T$_1$) and transversal (1/T$_2$) relaxation times, respectively, as a function of Gd concentrations. As shown in FIG. 2, the r$_1$ and r$_2$ of the polyrotaxane contrast agents is higher than that of DOTAREM® (Table 9), indicating that these compounds have macromolecular MRI contrast agent characters.

TABLE 9

Molar relaxivity of Gd$^{3+}$-HP-β-CD/SBE-β-CD based polyrotaxanes and DOTAREM ®

| Polyrotaxane | r$_1$ (mM$^{-1}$s$^{-1}$) (1H NMRD) | r$_1$ (mM$^{-1}$s$^{-1}$) (1/T$_1$) | r$_2$ (mM$^{-1}$s$^{-1}$) (1/T$_2$) |
|---|---|---|---|
| DOTAREM | — | 3.8 | 3.7 |
| Gd$^{3+}$-HPβCD/SBEβCD-F127 | 7.9 | 22 | 19 |
| Gd$^{3+}$-HPβCD/SBEβCD-F168 | 12 | 10 | 17 |
| Gd$^{3+}$-HPβCD/SBEβCD-L35 | 6.9 | 8.2 | 14 |
| Gd$^{3+}$-HPβCD/SBEβCD-L64 | — | 7.0 | 10 |
| Gd$^{3+}$-HPβCD/SBEβCD-L81 | 11 | 14 | 14 |

These high relaxivities obtained for the polyrotaxane compounds at high field likely can be attributed to an increase of their rotational tumbling time τ$_R$, which in this case is a combination of both the overall motion of the macromolecules and the internal motions of side chains that influence the relaxations rates as Lipari and coworkers have demonstrated. Additionally, since polyrotaxanes are known to have poor water solubility, their aggregation could have severe impact on the increment of the relaxivity. This phenomenon was recently observed by Elhabiri et al. The higher values obtained for Gd$^{3+}$-HP-β-CD/SBE-β-CD-F127 and Gd$^{3+}$—HP-β-CD/SBE-β-CD-L35 with this technique compared to that from $^1$H NMRD is probably due to the higher field at which the measurement was performed. Wood and Bologh groups have reported that high-field applications to complexes with shorter τ$_M$ can produce high relaxivity. The relaxivity values, r$_1$ and r$_2$, of Gd$^{3+}$—HP-β-CD/SBE-β-CD-F127, Gd$^{3+}$—HP-β-CD/SBE-β-CD-F68, and Gd$^{3+}$—HP-β-CD/SBE-β-CD-L81 are greater than that of Gd$^{3+}$—HP-β-CD/SBE-β-CD-L35 and Gd$^{3+}$—HP-β-CD/SBE-β-CD-L64. This can be explained in part by the size of the PEG blocks of the compounds. The large PEG blocks of the Gd$^{3+}$—HP-β-CD/SBE-β-CD-F127 and Gd$^{3+}$—HP-β-CD/SBE-β-CD-F68 (200 and 152 ethylene oxide units respectively) likely facilitate access of water molecules to the Gd chelate inside the particles. Kodjima et al. observed the same effect of the size of PEG on the relaxivity of PEGylated dendrimers. In the case of Gd$^{3+}$—HP-β-CD/SBE-β-CD-L81, its high threading coverage (90%) probably imparts to the molecule a rod shape-like structure, which could limit certain degrees of freedom of the CDs along the polymer axle and therefore, lower the molecule tumbling rate and shorten its relaxation time as results.

In some embodiments, polyrotaxanes of the various embodiments described herein have a concentration-dependent molar relaxivity (1/T$_1$ and/or 1/T$_2$ measured in deionized water at 7 T and 25° C.) of from about 5 to about 200 mM$^{-1}$s$^{-1}$ (e.g., about 5 mM$^{-1}$s$^{-1}$ to about 50 mM$^{-1}$s$^{-1}$, about 25 mM$^{-1}$s$^{-1}$ to about 35 mM$^{-1}$s$^{-1}$, about 50 mM$^{-1}$s$^{-1}$ to about 100 mM$^{-1}$s$^{-1}$, or about 50 mM$^{-1}$s$^{-1}$ to about 150 mM$^{-1}$s$^{-1}$).

In Vitro MR Imaging of Gd (III) Polyrotaxanes. To evaluate the signal enhancement properties of the polyrotaxane samples, a T$_1$-weighted spin-echo MR images were recorded for aqueous solutions of the samples with increasing concentrations of Gd. DOTAREM® and pure water images were also obtained in the same conditions. High positive contrast enhancement was observed for all the Gd³⁺—HP-β-CD/SBE-β-CD-based polyrotaxanes with the spots that become brighter with the increase of the Gd concentration as compared to those obtained from DOTAREM®. However, the brightness of the signals are observed from the lowest concentration with Gd³⁺—HP-β-CD/SBE-β-CD-F127 and Gd³⁺—HP-β-CD/SBE-β-CD-L35. These results showed that the prepared samples have similar or better contrast imaging than DOTAREM®.

In Vivo MRI Contrast Enhancement of Gd³⁺—HP-β-CD/SBE-β-CD-PRs. To investigate the MR contrast enhancement and the circulation fate in vivo of the polyrotaxanes, 3D T1-weighted MR images of Balb/C mice after intravenous injection were acquired with 7 T Bruker small animal scanner before injection and 10, 20, 35, 50, and 60 min post injection. The tissue contrast enhancement of the compounds has different fates dependent on the threading efficiency, molecular weight, size and surface charge of each contrast agent. FIGS. 3A-3E, where the maximum intensity projection images obtained from all the polyrotaxane contrast agents, except for Gd³⁺—HP-β-CD/SBE-β-CD-L64 are presented, shows great contrast enhancements for most of the polyrotaxane compounds in heart, liver, kidney, after 15 min, and bladder after 35 min. In general, the contrast intensities progressively decrease over time in heart and circulation system but significantly increase in bladder after renal clearance. As expected, DOTAREM® was completely eliminated within 20 min, a typical trend commonly observed for small contrast agents.

Surprisingly, Gd³⁺—HP-β-CD/SBE-β-CD-F127 has shown lower contrast enhancement when compared to the rest of the polyrotaxanes. This is probably do to the low theading (31%) that exposes the large PEG blocks and nearly half of the PPG block of the Pluronic F127. Apparently, the hydrophobic PPG block wrapped around the few Gd(III) chelates along with PEG blocks that form a corona shield them from having access to water. Kojima et al. have observed a strong effect of large PEG blocks (PEG 5 k) in reduction of relaxivity and enhancement of PEGylated dendrimers when compared to short PEG 2 k.[71] Conversely, high threaded polyrotaxanes contrast agents such as Gd³⁺—HP-β-CD/SBE-β-CD-L35 and Gd³⁺—HP-β-CD/SBE-β-CD-L81 show highest enhancements, likely due to their high threading efficiency that confers a rod-shape like morphology in circulation, and as a consequence, they avoid macrophage uptake and remain in circulation longer.

Figure 4:
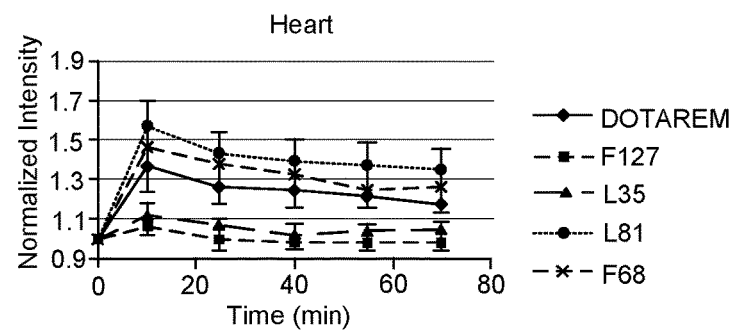
FIG. 4 is plots of normalized intensity of $Gd^{3+}$—HP-β-CD/SBE-β-CD based polyrotaxane contrast agents.
Figure 4:
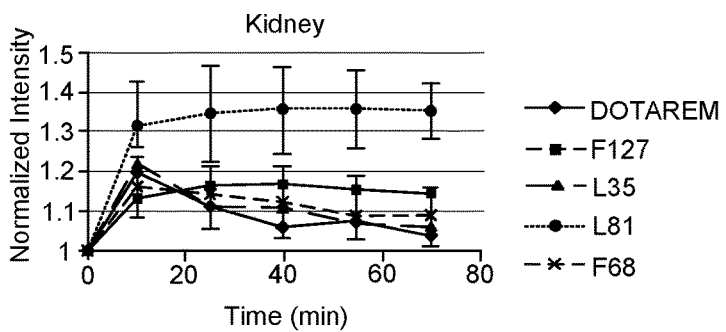
Figure 4:
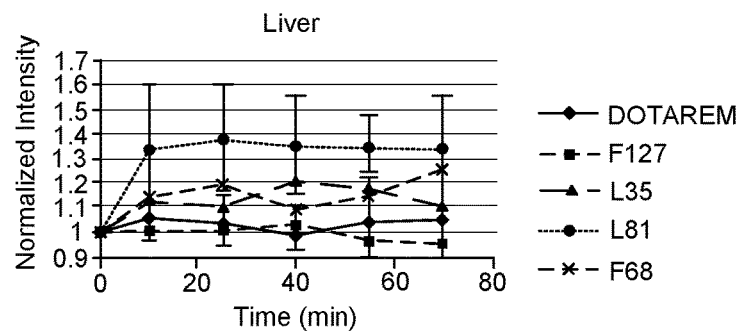

To quantify the contrast enhancements, the contrast signal-to-noise ratio (CNR) was calculated from regions of interest (ROIs) carefully drawn in the cross-section images of heart, liver, and kidney obtained from the 2D $T_1$-weighted scans. There was insignificant signal enhancement in all these tissues (FIG. 4). In heart, meaningful signal enhancements were observed for all polyrotaxanes, with the most notable increases obtained with Gd³⁺—HP-β-CD/SBE-β-CD-F68, Gd³⁺—HP-β-CD/SBE-β-CD-L35 and Gd³⁺—HP-β-CD/SBE-β-CD-L81. It appears that these compounds persist in circulation longer than DOTAREM® and Gd³⁺—HP-β-CD/SBE-β-CD-F127. These observations can be explained by the threading efficiency and high molecular weight of the former compounds. Kidney profiles look different in a way that Gd³⁺—HP-β-CD/SBE-β-CD-F127 and Gd³⁺—HP-β-CD/SBE-β-CD-L81 show accumulation and remain longer in tissue. For the liver, apart from Gd³⁺—HP-β-CD/SBE-β-CD-L81, which shows a high level of accumulation and demonstrates sustained persistence, the rest of the polyrotaxanes show low to medium presence in the tissues. Indeed, Gd³⁺—HP-β-CD/SBE-β-CD-L35 and Gd³⁺—HP-β-CD/SBE-β-CD-F68 accumulated in liver overtime with 25% increament of the contrast intensity for the later and 10% for the former 70 min after injection. Gd³⁺—HP-β-CD/SBE-3-CD-F127 SNR lines below that of DOTAREM®.

Figure 5:
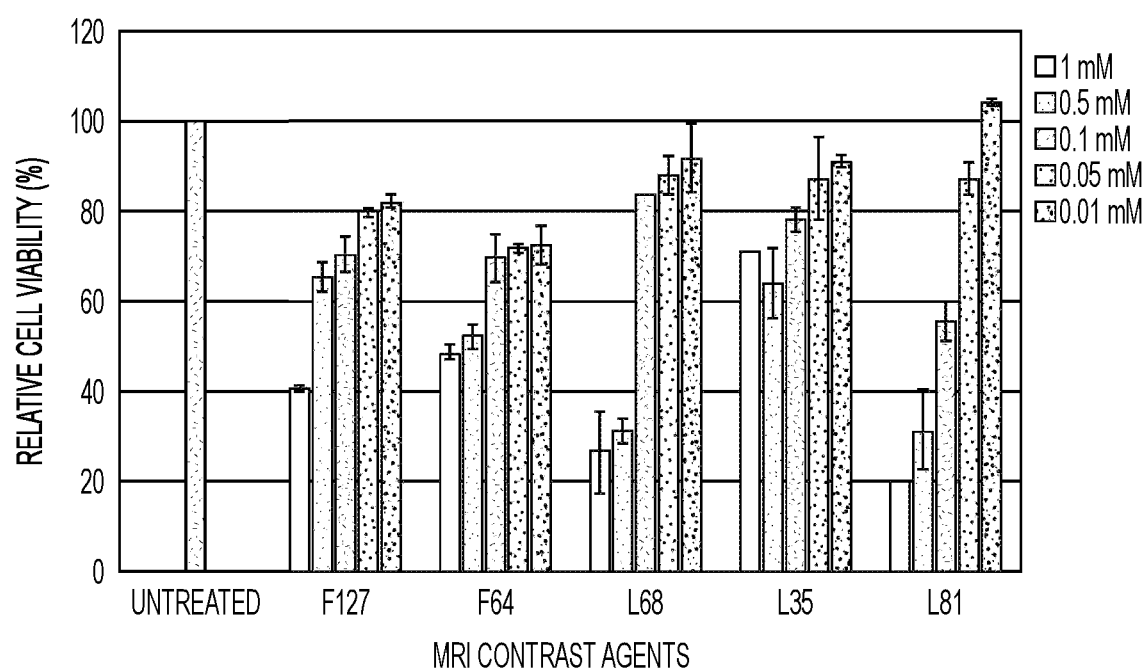
FIG. 5 is a plot of cell viability of the $Gd^{3+}$—HP-β-CD/SBE-β-CD based polyrotaxanes incubated with J774 macrophage cells.

In Vitro Cytotoxicity. To evaluate the biocompatibility of the Gd-polyrotaxanes, their cell viability was evaluated using MTS assay on J774 macrophage cells. The results shown in FIG. 5 were normalized to a control sample of cells incubated without sample. Overall, Gd³⁺—HP-β-CD/SBE-β-CD-PRs have a moderate effect on cell proliferation at Gd concentration of 0.1 mM indicating a reasonable tolerance of the polyrotaxane contrast agents safe for in vivo experiments. At this concentration, cell viabilities range from 70 to 83% for all the polyrotaxanes except for Gd³⁺—HP-β-CD/SBE-β-CD-L81. This could be attributed to the very small PEG block held by the L81 Pluronic copolymers since it has been demonstrated that PEG can decrease cytotoxicity in Gd-based macromolecule contrast agents.

Figure 6:
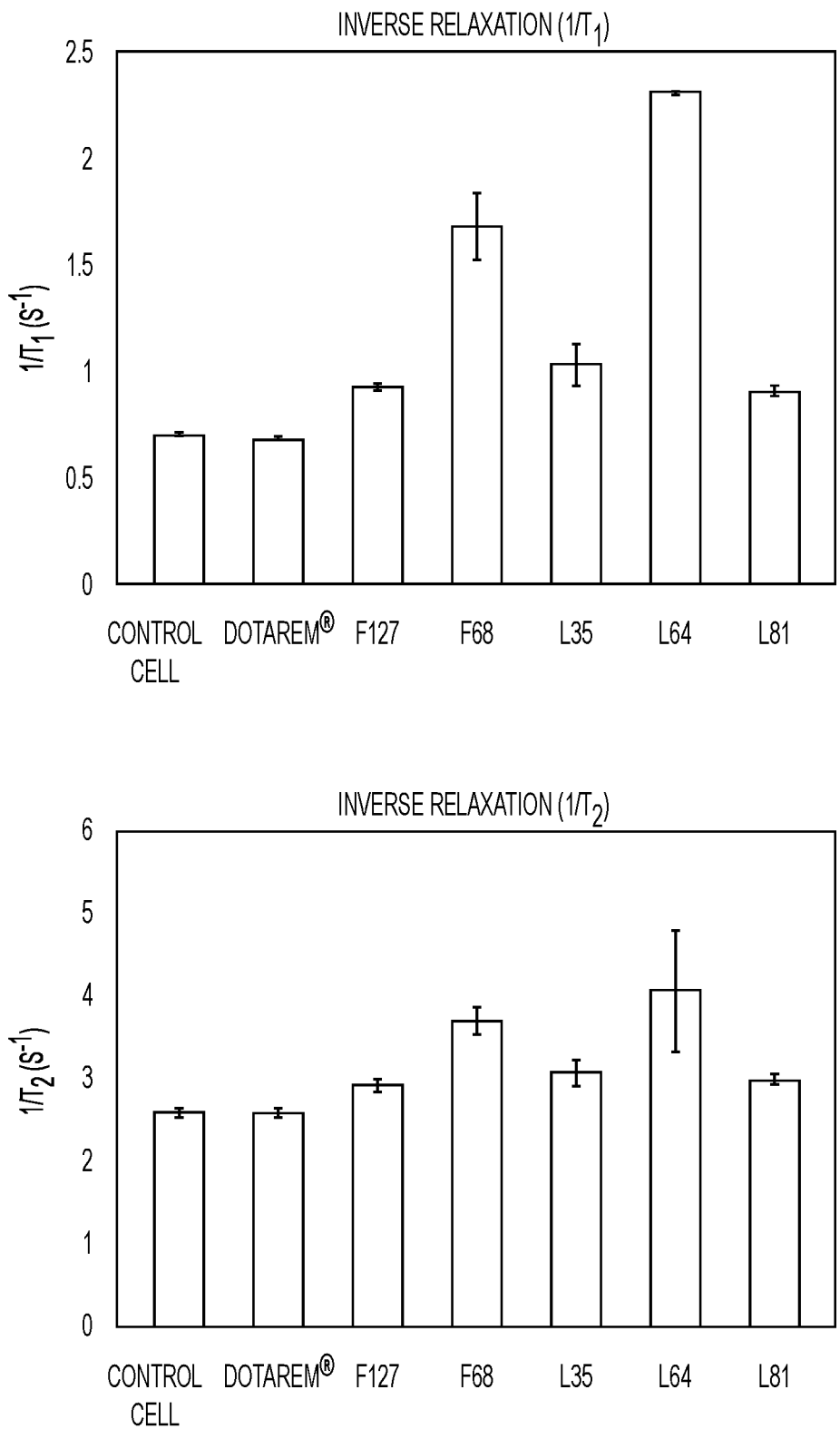
FIG. 6 is plots of cellular uptake of polyrotaxanes in J774 macrophage cells. F127: $Gd^{3+}$—HP-β-CD/SBE-β-CD-F127, F68: $Gd^{3+}$—HP-β-CD/SBE-β-CD-F68, L35: $Gd^{3+}$—HP-β-CD/SBE-β-CD-L35, L64: $Gd^{3+}$—HP-β-CD/SBE-β-CD-L64, L81: $Gd^{3+}$—HP-β-CD/SBE-β-CD-L81 Images were recorded with Bruker 7 T.

Cellular Uptake Studies. Since macromolecular constructs such as polyrotaxanes can trigger the innate immune system (monocytes, macrophages, dendritic cells) in vivo, their uptake of the polyrotaxane contrast was evaluated by macrophages using the MR imaging modality. In addition, one can take advantage of the biological properties of these materials to image macrophages in human diseases including cancer, atherosclerosis, myocardial infarction, diabetes and other conditions. Macrophages are known to play an important role in host system defense leading to the detrimental fate of most nanomaterials. Similarly, overexpression of macrophages are linked to many diseases including tissue regulation and angiogenesis in cancer,[76-78] destabilization of lesions leading to rupture of plaques of artery leading to stroke, and inflammatory diseases. MR imaging has been used to monitor tumor growth and cancer therapy, predict risk in cardiovascular disease, and visualize diabetes progression using macrophages accumulation at the tumor or lesion sites. Based on these reports, cellular uptake in J774 macrophages of the polyrotaxane contrast agents was assessed. The compounds were incubated with J774 cells at a final concentration of 0.1 mM Gd for 12 h at 37° C. in serum free media and lysed for MR imaging. $T_1$ and $T_2$ values from the lysed cells contained in 300 μL eppendorf tubes were measured using an inversion recovery sequence at 7 T and the inverse of spin-lattice ($1/T_1$) and spin-spin ($1/T_2$) relaxation times were evaluated. As shown in FIG. 6, the relaxation times are shortened with macrophages treated with the Gd³⁺—HP-β-CD/SBE-β-CD-PRs while DOTAREM® did not show any endocytosis as compared to the control cell that was not treated with samples. Since the polyrotaxanes are not endowed with any targeting capability to improve their endocytosis via receptor-mediated route, their high uptakes observed are nonspecific and probably resulting from the partition of the end-cap cholesterol of the polyrotaxanes in cell membranes favoring their internalization. This assumption is supported by the low uptake of DOTAREM® which does not possess any lipophilic property. These results suggest that polyrotaxane contrast agents are attractive for in vivo imaging and diagnosis of several macrophage associated diseases.

Polyrotaxane Protein Hard Corona Proteomics Analysis. The charge and surface chemistry of the polyrotaxanes described in this example was evaluated through incorporation of β-CD derivatives as mixtures of species on a Pluronic L81 core. Seeing how incorporation of different CD derivatives influence their biological performance will provide insight into the importance of overall physiochemical aspects and inform candidate selection for specific target conditions. To that end, four different polyrotaxanes that contain different β-CD derivatives were developed and characterized, namely, β-CD, HP-β-CD, Metylated beta cyclodextrin (Me-β-CD), and a mixture of HP-β-CD and sulfobutyl ether beta Cyclodextrin (SBE-β-CD) based polyrotaxanes (Table 10).

TABLE 10

Summary of number and coverage of CDs of polyrotaxanes for Proteomics Analysis

| Polyrotaxane | CD Feed Ratio | Total CD | SBE-β-CD | MW (NMR) (KDa) |
|---|---|---|---|---|
| β-CD | 100 | 18 | 0 | 26 |
| HP-β-CD | 100 | 11 | 0 | 22 |
| Me-β-CD | 100 | 8 | 0 | 16 |
| HP-β-CD/SBE-β-CD | 50:50 | 19 | 8 | 58 |

Incorporation of SBE-β-CD onto a PR scaffold would introduce electrostatic repulsion. While not wishing to be bound by any specific theory, it is anticipated that the sulfonate groups on the polyrotaxanes have the potential to drastically change the way PRs behave and interact with blood components. On the other hand, HP-β-CD provide excess of hydroxyl groups on the surface of the polyrotaxanes that could induce more hydrogen bonding interactions while introduction of Me-β-CD would undeniably reduce these hydrogen bonding interactions.

Figure 7:
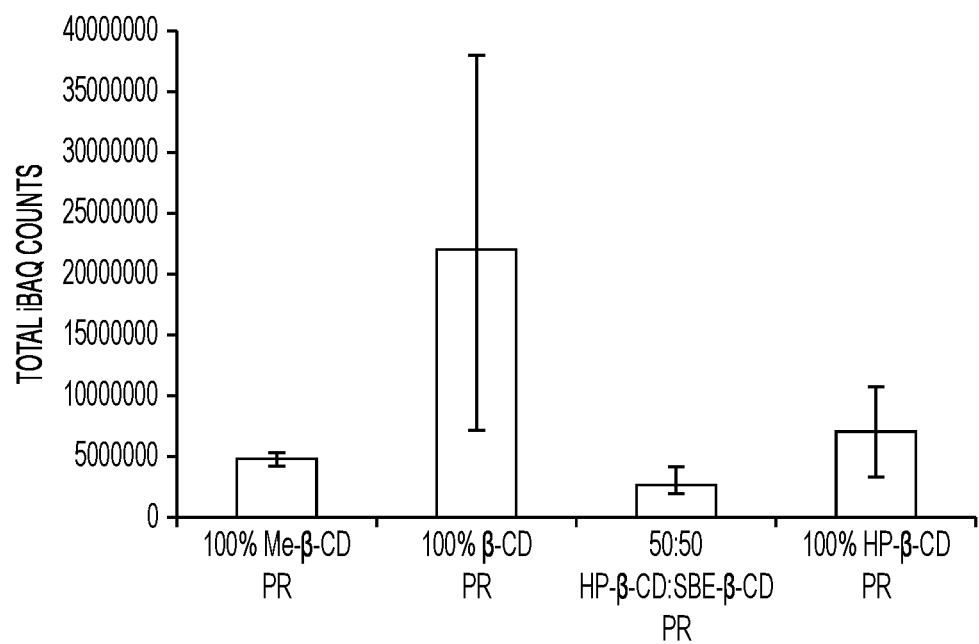
FIG. 7 is a plot of total protein adsorption onto polyrotaxanes (PRs) of different CD derivatives.

Changes in the CD derivatives carried by the PR scaffolds yielded differences in the amounts and identities of proteins composing the PR hard corona. Total amounts of adsorbed protein varied greatly across the CDs incorporated on the polyrotaxanes and therefore their surface chemistry as shown in FIG. 7. Unmodified β-CD amassed the largest quantity of surface proteins, possibly because of the rigidity of the hydrogen bonded backbone and the availability of reactive surface alcohols on the CD rim. HP-β-CD PRs had the second highest average protein adsorption, potentially for similar reasons. Decrease in HP-β-CD relative to unmodified β-CD PR may be mediated by a brush-like shielding originating from the HP modifications or a less regular availability of reactive alcohols. Me-β-CD and mixed threading PRs picked up roughly the same amount of protein despite exhibiting very different surface chemistries. Decreased adsorption in Me-β-CD may originate from the capping of surface alcohols. It also appears that incorporation of charged CDs also reduces adsorption by some mechanism, potentially by increased repulsion or the reduction of hydrophobic interactions. Further careful study is necessary to definitively pinpoint the mechanisms behind these differences.

In order to discern whether certain polyrotaxane architectures will interact specifically within certain pathways, proteins present in each corona were sorted into certain their respective families. When comparing protein groups, CD variation again led to changes in preferential protein family deposition (FIG. 7). Across the entire family, polyrotaxanes had high percentages of adsorbed lipoproteins. The corona featuring the lowest percentage of lipoprotein content was unmodified β-CD-based polyrotaxane with this family accounting for ~30% of the total corona. Incorporation of unmodfied CD appears to drive the recruitment of other protein families, reducing the percentage occupied by lipoprotein dysopsonins. In addition, because all members of this polyrotaxane family adsorb similar percentages of lipoproteins, it appears that association with these proteins is modified by the PR core or endcaps, not the specific CD chemistries. Lipoproteins are known to carry cholesterol, cholesterol esters, and fatty acids through the blood stream and may therefore be prone to association with the polyrotaxane cholesterol endcaps. Notably, β-CD PR and HP-β-CD PR achieve significantly greater immunoglobulin deposition than their counterparts. This may be due to antibody recognition of the 1,4-glucose architectures, as the rigid sugar backbones could resemble surfaces present on invading bacteria. This could indicate that these materials will be prone to more rapid clearance from the body. HP-β-CD PRs also represent the largest fractions of serum album of the group, with ~20% albumin content, although every PR picked up this protein to some extent. Again, this association may be explained by endcap association with albumin hydrophobic pockets.

HP-β-CD PRs also featured significantly diminished levels of complement adsorption despite unmodified alcohols on the CD surface, with Complement C3 only representing ~2% of the corona relative to other architectures. In contrast, Me-β-CD PRs were amongst the highest complement protein recruiters despite the reduction of alcohol surface chemistry implying a mechanism of adsorption other than covalent modification. All four scaffolds exhibit little deposition of coagulation pathway proteins. It is likely that this is partially due to the use of human serum, which is depleted of fibrinogen, and not human plasma.

Figure 8:
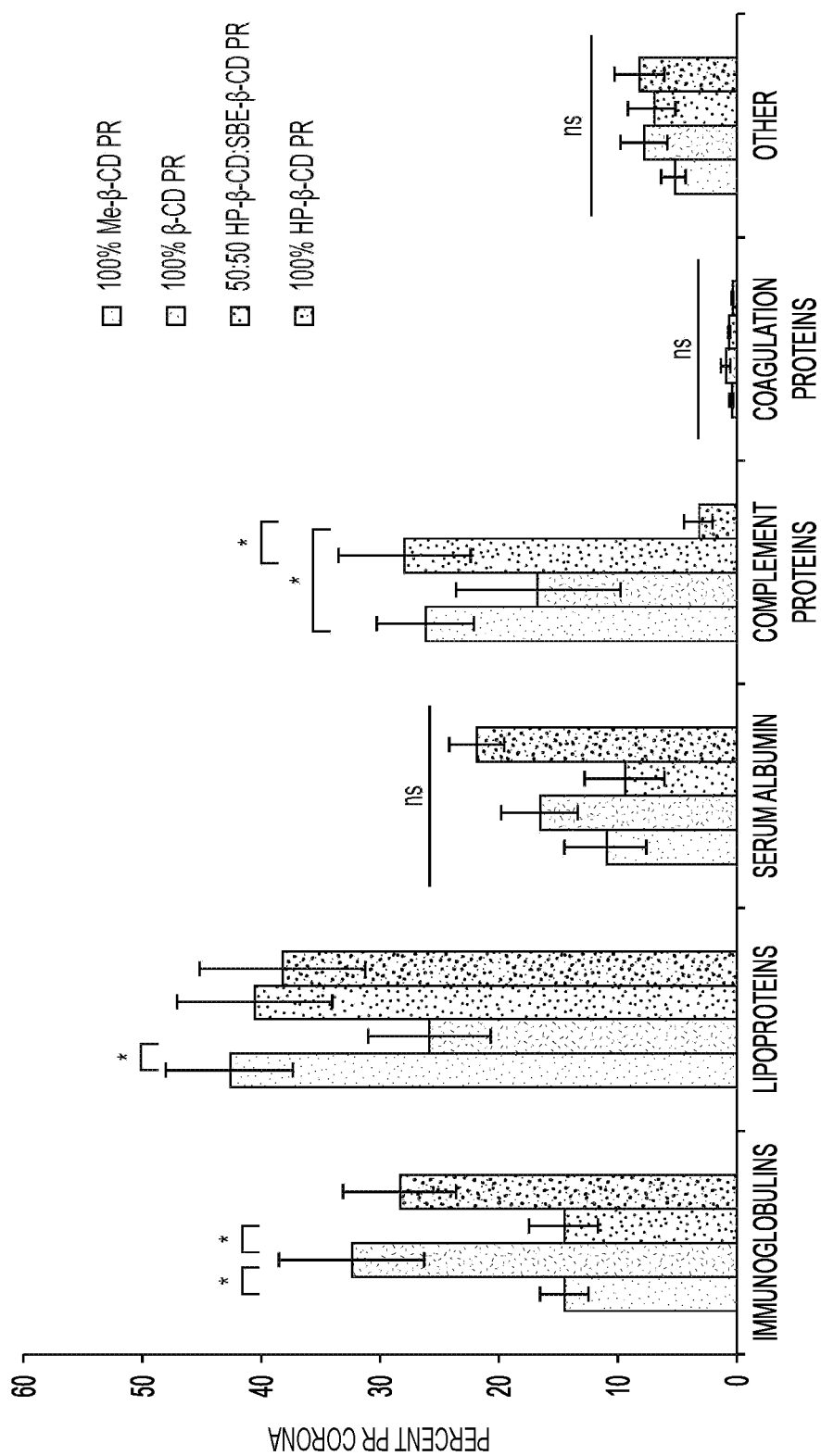
FIG. 8 is a plot of average percent of polyrotaxane protein corona.

A table showing the most abundant proteins in the corona of each PR is shown in FIG. 8. The most abundant protein in the corona of unmodified β-CD and HP-β-CD PRs is serum albumin. This increased representation of surface albumin may lend these architectures an extended circulation time relative to other architectures. In both cases, the second most abundant protein is immunoglobulin kappa, reflecting the high percentage of their coronas represented by albumins and immunoglobulins. Both architectures feature large numbers of lipoproteins in their top 20 proteins. Additionally, both polyrotaxanes coronas feature serotransferrin and apolipoprotein E (ApoE), increasing the potential for blood-brain barrier (BBB) penetration.

Me-β-CD and mixed SBE-β-CD PR share their top three most abundant proteins, making up ~45.2% and ~41.5% of their total coronas respectively. These proteins are complement C3, apolipoprotein E, and serum albumin, respectively. It is interesting that complement C3 relatively more abundant despite the capping of reactive surface alcohols, again suggesting an alternative mechanism to covalent attachment. Having complement C3 occupy the predominant fraction of the protein corona may lead to complement pathway mediated hypersensitivity reactions. The high percentage of apolipoprotein E on Me-β-CD and the mixed threading polyrotaxane, 16.9% and 12.2% respectively, increases the chances for these architectures to cross the BBB. The fact that these architectures share such large fractions of their coronas is interesting given the physiochemical differences in the CDs they carry.

Collectively, all of the PR family members share ten of their top twenty most abundant proteins. Among these proteins are complement C3, serum albumin, three immunoglobulins and four lipoproteins. Many of the other proteins overlap multiple architectures but are not present in all four coronas. Each pairing of PRs share between 13 and 15 identified proteins. This shows that serum protein response to PR incubation is similar despite differences in CD character. Overall, then, the similarities between the PR structures (polymer structure, endcap chemistry, and shape) may be playing a larger part in protein recruitment than CD character.

The composition and chemistry of the polyrotaxanes surface obviously controls the binding of the serum proteins on their hard coronas. The actual identities of the proteins in the corona, however, can be very similar. This indicates that the overall polyrotaxanes structure may be similar enough in most cases to promote recruitment of similar proteins onto their surface.

In summary, five gadolinium HP-β-CD/SBE-β-CD based polyrotaxane contrast agents were synthesized and characterized with the relative proportions of CDs threaded controlled across the compounds in the range of 40 to 50% SBE-β-CD. DLS results suggested that the polyrotaxanes are polydisperse with sizes ranging 110 to 290 nm. Zeta-potential measurements indicated that the compounds are slightly negatively charged due to the sulfonate negative charge of SBE-β-CD. This negative charge contributes to improving their water solubility significantly. Nuclear Magnetic Relaxation Dispersion ($^1$H NMRD) and molar relaxivity measurement revealed at 23° C. that all the polyrotaxanes had high spin-spin relaxation ($T_1$) and spin-lattice relaxation ($T_2$) rate as compared with commercial DOTAREM® (Gd-DOTA). Macrophage cell viability and uptake studies demonstrated low toxicity of all the macromolecular agents and high cellular uptake while DOTAREM® showed almost no cellular uptake. In vivo $T_1$-weighted images acquired at 7 T on Balb/c mice injected intravenously at 0.05 mmol Gd/kg body weight with the Gd-HPβ-CD/SBE-βCD-PRs saline solutions showed an increase in contrast intensity for all polyrotaxanes with longer circulation times in blood pool than that of DOTAREM®. A macrophage uptake analysis reveals that these macromolecular contrast agents can be attractive for in vivo imaging and diagnosis of several macrophage associated diseases such as cancer. Additionally, a proteomics study of the polyrotaxanes indicates that the composition and chemistry of their surface controls the binding of the serum proteins on their hard coronas their overall structure may be similar enough to promote recruitment of similar proteins onto their surface.

Materials. Pluronic triblock copolymers F127 (EO 200, PO 65, MW=12600), F68 (EO 153, PO 29, MW=8350), L35 (EO 22, PO 16, Mw=1900), L64 (EO 26, PO 30, MW=2900), and L81 (EO 6, PO 43, MW=2800) were purchased from Sigma-Aldrich and dried by azeotropic distillation from benzene under vacuum before use. 2-Hydroxypropyl-β-Cyclodextrin, with 6.8 average degree of substitution, carbonyldiimidazole (CDI), triethylamine (TEA), tris(2-aminoethyl)amine (TAEA), cholesteryl chloroformate, were also purchased from Sigma-Aldrich and were used directly. 4-Sulfobutylether-β-cyclodextrin (SBE-β-CD or Captisol) was obtained from Cydex Pharmaceuticals (Lawrence, Kans.) with an average degree of SBE substitution of 6.0-7.1 and was also used without further purification. S-2-(4-Isothiocyanatobenzyl)-1,4,7,10-tetraazacyclododecane tetraacetic acid (p-SCN-Bn-DOTA) was obtained from Macrocyclics (Dallas, Tex.). All solvents were reagent grade, purchased from commercial sources, were dried over $CaH_2$, filtered, distilled at reduced pressure and stored under Argon prior to use. Cellulose dialysis membranes were obtained from Spectrum Labs and immersed in deionized water for at least 30 min prior to use. Ultra-pure H2O (resistivity=18.0 MΩ/cm$^{-1}$) was generated using a NANOpure Ultrapure water system.

Synthesis of Bis-Cholesterol-End-Capped HP-β-CD/SBE-β-CD Pluronic Polyrotaxanes (HP-β-CD/SBE-β-CD-PR). Before the synthesis of the polyrotaxanes, all the Pluronic copolymers were modified to obtain α,ω-bis-tris (2-aminoethyl)amine Pluronic. The synthesis of the polyrotaxanes were then carried out according the heterogeneous cyclodextrin threading procedure described previously with slight modification. Typically, 2 g of each dried α,ω-bis-tris (2-aminoethyl)amine Pluronic triblock copolymer was suspended in 70 mL hexane and dispersed by bath sonication for about 5 min, before stirring until the solution appeared homogeneous. HP-β-CD and SBE-β-CD were mixed with a molar ratio of 30% of SBE-β-CD using the ratio of CD:PO unit=1:2 for each type of Pluronic and finely ground for 30 min. The powdered cyclodextrin mixtures were added to the polymer suspension before vigorously stirred for 2 h. The mixtures were then bath sonicated for 1 h at 20° C., followed by 10 min probe sonication (Model W-350, 50 W, ½" probe) to improve the dispersion of the Pluronic copolymers. The mixtures were allowed to stir for 72 h at 20 C before the solvent was removed under reduced pressure and the resulting materials were redissolved in 40 to 60 mL of dried $CH_2Cl_2$ before cholesteryl chloroformate (12 equiv) was added. The reaction mixtures were stirred at 20° C. for 24 h, concentrated, and then precipitated in diethyl ether (700 mL). To remove unreacted reagents and unthreaded cyclodextrins, the crude products were dissolved in $CH_3OH$ (300 mL) and precipitated in 500 mL diethyl ether then filtered. Finally, the products were purified by sequential dialysis using 12,000-14,000 and 6,000-8,000 MWCO regenerated cellulose membranes in DMSO first and progressively exchanged with deionized water for 5 days before lyophilization to generate white HP-β-CD/SBE-β-CD-PR-Chl powders. $^1$H NMR (500 MHz, Cryo probe, DMSO-d6): δ=6.92 ppm (S, H—NCO carbamate), 5.25 ppm (t, 1H, Chl-ethylene H), 4.5-5.0 ppm (b, $C_1$—H of CDs), 4.5 ppm (b, OH propyl of HP-β-CD), 3.5-3.8 ppm (m, $C_{3,5,6}$—H of CDs), 3.5 ppm (m, PEG-$CH_2$), 2.6-2.8 ppm (m, 16H, $CH_2$ of TAEA), 1.6 ppm (b, ($CH_2$)—$SO_3$—), 1.2 ppm (d, $CH_3$-HP-β-CD), 1.0 ppm (d, $CH_3$ of PPG), 0.8-0.6 ppm (m, Chl-$CH_3$).

Synthesis of 1,8-diamino-3,6-dioxooctane Modified Polyrotaxane (DADO-HP-β-CD/SBE-β-CD-PR). Dried polyrotaxane (200 mg) from the previous step was dissolved in 20 mL DMSO and stirred under Argon atmosphere. To this mixtures, TEA (1.5 equivalent of OH groups) was added and the reactions were stirred for 30 min before excess of 1,1'-carbonyldiimidazole was added and allowed to stir for 24 h. Next, excess of 1,8-diamino-3,6-dioxooctane was slowly added to the solutions and the mixtures were allowed to stir for 24 h at 20° C. The products were purified by dialysis using 12,000-14,000 and 6,000-8,000 MWCO regenerated cellulose membranes in DMSO and deionized water for 3 days, then freeze-dried by lyophilization to generate the white powder of the 1,8-diamino-3,6-dioxooctane modified polyrotaxanes (DADO—HP-β-CD/SBE-β-CD-PR). $^1$H NMR (500 MHz, Cryo probe, DMSO-d6): δ=6.92 ppm (S, H—NCO carbamate), 5.25 ppm (t, 1H, Chl-ethylene H), 4.5-5.0 ppm (b, $C_1$—H of CDs), 4.5 ppm (b, OH propyl of HP-β-CD), 3.5-3.8 ppm (m, $C_{3,5,6}$—H of CDs), 3.5 ppm (m, PEG-$CH_2$), 2.6-2.8 ppm (m, 16H, $CH_2$ of TAEA), 1.8 ppm (b, $NH_2$ of DADO), 1.6 ppm (b, ($CH_2$)—$SO_3^-$), 1.2 ppm (d, $CH_3$—HP-β-CD), 1.0 ppm (d, $CH_3$ of PPG), 0.8-0.6 ppm (m, Chl-$CH_3$).

Synthesis of p-SCN-Bn-DOTA modified Polyrotaxanes (DOTA-HP-β-CD/SBE-βCD-PR). HP-β-CD/SBE-β-CD-PRs (150 mg) from the previous step was dissolved in 5 mL DMSO and stirred under Ar. To this mixture, p-SCN-Bn-DOTA (50 mg, 0.073 mmol) was added and allowed to stir for 24 h at 20° C. The reaction was stopped and the products purified by dialysis to remove any unreacted reagents using 12,000-14,000 and 6,000-8,000 MWCO regenerated cellulose membranes in DMSO, followed by water, before lyophilization to generate powdered samples of p-SCN-Bn-DOTA modified polyrotaxane (DOTA-HP-β-CD/SBE-@CD-PR). $^1$H NMR (500 MHz, Cryo probe, DMSO-$d_6$): δ=13 ppm (Ben-NH-urea), 9.5 ppm (urea-NH—) 7.5-7.0 ppm (d, 4H—Ar-DOTA), 6.92 ppm (S, H—NCO carbamate), 5.25 ppm (t, 1H, Chi-ethylene H), 4.5-5.0 ppm (b, $C_1$—H of CDs), 4.5 ppm (b, OH propyl of HP-β-CD), 3.5-3.8 ppm (m, $C_{3,5,6}$—H of CDs), 3.5 ppm (m, PEG-$CH_2$), 2.6-2.8 ppm (m, 16H, $CH_2$ of TAEA), 1.8 ppm (b, $NH_2$ of DADO), 1.6 ppm (b, $(CH_2)$—$SO_3$—), 1.2 ppm (d, $CH_3$-HP-β-CD), 1.0 ppm (d, $CH_3$ of PPG), 0.8-0.6 ppm (m, Chl-$CH_3$).

Preparation of Polyrotaxanes Gadolinium Complexes ($Gd^{3+}$—HP-β-CD/SBE-β-CD-PR). The gadolinium complexation was performed as follows: $GdCl_3.6H_2O$ (2 equiv of one DOTA) was dissolved in $H_2O$ (5 mL) and mixed with the DOTA-HP-β-CD/SBE-RCD-PR samples previously dissolved in $H_2O$ (10 mL) and the pH of the solutions was maintained around 5.5-6.50 using NaOH and HCl solutions. The reaction mixtures were stirred at 50° C. for 48 h and the products were dialyzed against water (pH 7) for 3 days using membrane with MWCO of (6.0-8.0 kD). To remove non-chelated gadolinium, the samples were run through a Sephadex G 25 column and Xylenol orange was used to detect traces of free Gd(III) ions. No color change should be observed (from yellow to pink or purple) with Xylenol orange in the polyrotaxane sample solutions after dialysis. A UV-visible instrument (CARY 50 Bio UV-Visible Spectrophotometer) was utilized to estimate the absorbance at two wavelengths (435 and 578 nm). Pink and purple colors of the 50 μL of aqueous solutions of the samples and 500 μL of an acetate buffer of the dye indicating presence of free Gd. The fractions collected were freeze-dried to give the final products.

Nuclear Magnetic Resonance, NMR. $^1$H NMR spectra were collected using Bruker AV-Ill-500-HD equipped with a CryoProbe. Spectra were recorded at 25° C. using DMSO-$d_6$ as solvent unless otherwise indicated, using approximately 15 mg of each polyrotaxane dissolved in 1 mL of DMSO deteuriated solvent.

Gel Permeation Chromatography. Absolute masses of the polyrotaxane contrast agents were obtained from an Agilent Technologies 1200 series chromatograph equipped with a Shodex SB-803-HQ column with DMSO as eluant at a flow rate of 0.1 mL/min using RI and light scattering detections. Pullulan (MW 12,000 kD), and three dextrans (MW 11,600; 48,600; and 667,800 kD) were used as standards. The samples were dissolved in DMSO (2 mg/mL) and eluted for 150 min.

Analytical Ultracentrifugation Analysis. AUC (Becman Coulter optimer-XL1) technique was used to determine the molecular weight of the polyrotaxane molecules. A velocity sedimentation method was performed with a speed of 50000 rpm for 20 h. The samples were dissolved in DMSO at a concentration of 1 mg/mL and introduced in 7.15 cm cells. The reference cell was filled with pure DMSO.

Inductively Coupled Plasma Mass Spectroscopy. ICP-MS (Quadrapole ICP-MS (Agilent Technologies 7500am, West Lafayette, Ind.) was utilized to analyze gadolinium content in the polyrotaxanes. Samples were digested with 2% nitric acid (TraceMetal Grade, Fisher Scientific) and diluted from a gadolinium, 2% $HNO_3$ Certiprep ME 1 standard solution of 1 mg/mL (SPX CertiPrep, Metuchen, N.J.) using a standard additive method and introduced into a temperature controlled spray chamber with a MicroMist Nebulizer (Glass Expansion 4 Barlow's Landing Rd.

Measurement of the Hydrodynamic Diameter and Surface Zeta-Potential of the $Gd^{3+}$—HP-β-CD/SBE-βCD-PR. The sizes, size distributions and zeta potentials of the materials were evaluated by dynamic light scattering using a particle size analyzer (Zetasizer Nano S, Malvern Instruments Ltd.) at 20° C. with a scattering angle of 900. At least 3 measurements were made and averaged for each sample for zeta potential as well as size determination.

$^1$H NMRD. The longitudinal relaxation rate curves of all the samples were acquired on about 0.5 mM aqueous solutions in non-deuterioted water using a Stelar SPINMASTER 1 T fast field cycling (FFC) relaxometer (Stelar Mede, Pavia, Italy) according to the conventional FFC method covering 30 values of magnetic fields from 0.24 mT to 0.97 T corresponding to proton Larmor frequency range of 0.010-40 MHz. Standard Pre-Polarized (PP/S) and Non-Polarized (NP/S) acquisition sequences were used at 30° C. The samples were polarized in a high magnetic field Bpol (25 MHz) until the nuclear magnetization of $^1$H nucleus reached saturation. Then the magnetic field was switched to the detection field Bacq (16 MHz) and the magnetization was measured by a 90° pulse followed by acquisition of the time dependence decay curves.

Relaxivity Measurements. The longitudinal and transversal relaxation rate of the contrast agents and J774 macrophage cells were measured using a 7 T Bruker BioSpec scanner (Bindley Bioscience Center, West Lafayette, Ind.) 47/30 equipped with a Bruker Biospin MRI GmbH volume coil, 86 mm ID, operating at 300 MHz at 23° C. (RES 300 1 H 112/086 QNS TO AD). The polyrotaxane samples were dissolved in deionized water and 5 solutions (300 μL) with concentrations of 0.05, 0.10, 0.30, 0.50, 0.80, and 1.0 mM of Gd content were prepared. In the case of the Cellular uptake experiment, the lysed macrophage cells were transferred into 300 μL appendurf container. $T_1$ and $T_2$ values were measured using inversion recovery sequence and multi-slice-multi-echo (MSME) sequence respectively. For each image obtained from the solutions of the samples, nonlinear magnetization regression equations, $M_z=M_o(1-e^{-t/T_1})$ for $T_1$ and $M_{xy}=(e^{-t/T_2})$ for $T_2$ by fitting a least-squares curves. The parameters used are as followed. $r_1$: Repetition times, $T_E$=50.72, 100, 350, 750, 1250, 2500, 3500, and 5000 ms, echo time, $T_E$=22.22 ms, FOV=10×10 mm$^2$, matrix=128×128, slice thickness=1.0 mm, acquisition number=1. $r_2$: $T_R$=2000 ms, $T_E$=15, 30, 45, 60, 75, 90, 105 ms, FOV=20×20 mm$^2$, matrix=128×128, slice thickness=1 mm, acquisition number=1. $r_1$ and $r_2$ values were determined by as the slopes of the lines for the plot of $1/T_1$ and $1/T_2$ against Gd concentrations, respectively, using the same ROI.

In Vitro MRI Imaging. MR images of the solutions of the polyrotaxane samples previously analyzed during the relaxivity study, and the macrophage cells were acquired with the same instrument 7 T Bruker BioSpec scanner (Bindley Bioscience Center, West Lafayette, Ind.) 47/30 equipped with a Bruker Biospin MRI GmbH volume coil, 86 mm ID, operating at 300 MHz. $T_1$-weighted (T1w) spin echo images were collected under the following parameters: $T_R/T_E$=100/4 ms, FOV=58×58 mm2, matrix=256×256, slice thickness=2 mm, FA=90°, acquisition number=1. The images obtained were treated with ImageJ.

In Vivo MR Imaging. Animals. In vivo studies of the polyrotaxanes contrast agents were performed with 7-9 weeks old female BALBc mice (20 g each) following the protocol (1112000342) approved by Purdue Animal Care and Use Committee (PACUC). The mice (n=3) were anesthetized with isofluorane (Abbott Laboratories, Abbott Park, Ill.) which was mixed with 100% oxygen by a SomnoSuite instrument. The induction conditions were fixed to 250 mL/min of oxygen with 2.5% isofluorane while the mice were immobilized in the scanner with 250 mL/min oxygen, 1.8% isofluorane. The temperature of the mice was maintained by a water heating bath bed system while the respiration rate was monitor by a SA system equipped with an air pad inserted under the mice. Methods. A high resolution $T_1$-weighted 3D gradient echo sequence was run to scan the mice in a 7 T Bruker BioSpec scanner (Bindley Bioscience Center, West Lafayette, Ind.) 47/30 equipped with a Bruker Biospin MRI GmbH volume coil, 86 mm ID, operating at 300 MHz, and interfaced to a ParaVision software to collect coronal images. The mice were then injected intravenously vial tail vein with 200 μL of saline solution of sample at 0.05 mmol/kg body weight before postinjection images were acquired at 5 different time points with the same high resolution $T_1$-weighted 3D sequence under the following parameters: $T_R/T_E$=15/3.0 ms, FOV=80×30×30 mm$^3$, matrix=384×192×32, slice thickness=30 mm with no slice gap, FA=20°, acquisition number=3, resolution=0.20×0.15× 0.90 mm$^3$. Similarly, a 2D T1-weighted transversal images were acquired at different time points to reveal different vascular organs under the following parametrs: $T_R/T_E$=500/ 1.5 ms, FOV=50×50 mm$^2$, matrix=256×256, slice thickness=2 mm, FA=30°, acquisition number=2, resolution=0.20×0.20 mm$^2$, slice gap=1.0 mm with. Image Analysis. To quantify the changes in tissues signal intensity, regions of interest (ROIs) were drawn in images of different organs obtained from the 2D T1-weighted scans and ParaVision software was used to evaluate the mean intensities. The contrast-to-noise ratio (CNR) was calculated for the tissues using the following equation:

$$CNR = \frac{MSI(\text{tissue}) - MSI(\text{muscle})}{StD(\text{background})}$$

Where MSI stands for mean signal intensity and StD denotes standard deviation.

Cell Viability. Cell viability studies were performed to examine the potential for toxicity with PR in J774 cells using MTS assay. Cell viability were measured as a function of amount of PR. The cells were cultured in complete DMEM medium supplemented with 10% FBS at 37° C., 5% $CO_2$, and 95% relative humidity. The cells were seeded in 96-well microtiter plates (Nunc, Wiesbaden, Germany) at densities of 10,000 cells/well. After 24 h, the culture media was replaced with serum-free culture media containing increasing concentrations of PR and the cells were incubated for 24 h before addition of MTS reagent (15 μL) and incubated for 2 h. The absorbance was then measured using a microplate reader (SpectraMax Plus 384 plate reader) at a wavelength of 492 nm. The cell viability (%) relative to control cells cultured in media without PR was calculated as $[A]_{test}/[A]_{control}$×100%, where $[A]_{test}$ is the absorbance of the wells with PR and $[A]_{control}$ is the absorbance of the control wells (untreated cells). All cytotoxicity values were measured in triplicate and averaged.

Cellular Uptake Studies. MRI scanning was used to determine cellular internalization of the compounds. This method is perfect to study cellular uptake of samples that are not considered as cationic or not complexed with nucleotides. To do this, J774 macrophage cell line were used to study the uptake of the complexes by plating 100,000 cells per well in 24-well plates and incubating for 24 h before the experiment. PR compounds were incubated with the cells at final concentration of 0.1 mM for 12 h at 37° C. in serum free media. After 12 h, the spent media was removed and the cells were washed with PBS and trypsinized and lysed. These cells were then collected and analyzed using reverse spin echo scanning on Bruker 7 T Biospect small animal scanner (Bindley Bioscience Center, West Lafayette, Ind.). The relaxations $T_1$ and $T_2$ values were collected from samples images recorded from the cells contained in 300 μL plastic containers using the scanning conditions similarly to those employed for In vitro imaging of polyrotaxane solutions.

Protein Hard Corona Proteomics. Normal human serum was purchased from Complement Technology, Inc (Tyler, Tex.) and thawed immediately before use. PRs (100 μg) were taken up in PBS and sonicated for 10 min before incubation with undiluted human serum (1:1 v/v) for 1 h at 37□C. After incubation, samples were centrifuged for 10 min at 4000×g and PR pellets were washed four times with 150 μL cold PBS. Three separate incubations were done for each PR family member.

Tryptic peptides were separated on a nanoLC system (1100 Series LC, Agilent Technologies, Santa Clara, Calif.). The peptides were loaded on the Agilent 300SB-C18 enrichment column (5×0.3 mm, 5 μm) for concentration and the enrichment column was switched into the nano-flow path after 5 min. Peptides were separated with the C18 reversed phase ZORBAX 300SB-C18 analytical column (0.75 μm×150 mm, 3.5 um) from Agilent. Column was connected to the emission tip from New Objective and coupled to the nano-electrospray ionization (ESI) source of the high-resolution hybrid ion trap mass spectrometer LTQ-Orbitrap XL. (Thermo Scientific). The peptides were eluted from the column using acetonitrile/0.1% formic acid (mobile phase B) linear gradient. For the first 5 min, the column was equilibrated with 95% H2O/0.1% formic acid (mobile phase A) followed by the linear gradient of 5% B to 40% B in 65 min. at 0.3 ul/min, then from 40% B to 100% B in additional 10 minutes. Column was washed with 100% of ACN/0.1% FA and equilibrated with 95% of H2O/0.1% FA before next sample was injected (total method time=95 min.). A blank injection was run between samples to avoid carryover. The LTQ-Orbitrap mass spectrometer was operated in the data-dependent positive acquisition mode in which each full MS scan (30,000 resolving power) was followed by eight MS/MS scans where the eight most abundant molecular ions were selected and fragmented by collision induced dissociation (CID) using a normalized collision energy of 35%. Database searching was conducted using MaxQuant for LFQ (Label Free Quantitation—LFQ). The Human (SwissProt) annotated database was used for the search. Initial Spectral Counting was performed using the Mascot Database search results.

The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those of ordinary skill in the art, and that such modifications and variations are considered to be within the scope of this invention as defined by the appended claims.

The present invention provides for the following embodiments, the numbering of which is not to be construed as designating levels of importance:

Embodiment 1 relates to a polyrotaxane comprising a poloxamer core and at least one cyclodextrin, wherein the polyrotaxane has the general formula:

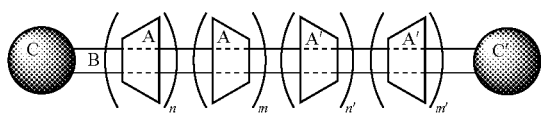

or salts thereof,
wherein:
each m and n is, independently, an integer from 0 to 30, with the proviso that m+m'+n+n' is from about 4 to about 30;
C and C' are the same or different and represent end capping groups of the formula:

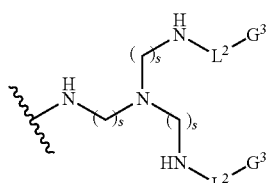

wherein each $L^2$ is independently a bond or $(C_1-C_6)$acyl; each $G^3$ is a substituted or unsubstituted $(C_5-C_{50})$ hydrocarbyl group, interrupted by 0 to 5 groups chosen from —O—, —NH—, and —S—, wherein the $(C_6-C_{50})$hydrocarbyl group is sterically bulky; and each s is independently an integer from 1 to 6;
B represents:

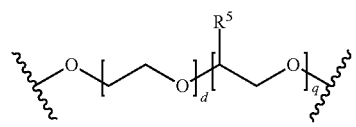

to which the endcapping groups are covalently attached to B via a $(C_1-C_6)$hydrocarbylene group or B represents carbohydrates, polypeptides, polycarbonate, polyamide, or polyester polymers;
wherein $R^5$ is methyl; d is an integer from about 1 to about 800; and q is an integer from about 6 to about 800; and
A represents the macrocyclic host molecule of the general formula (I):

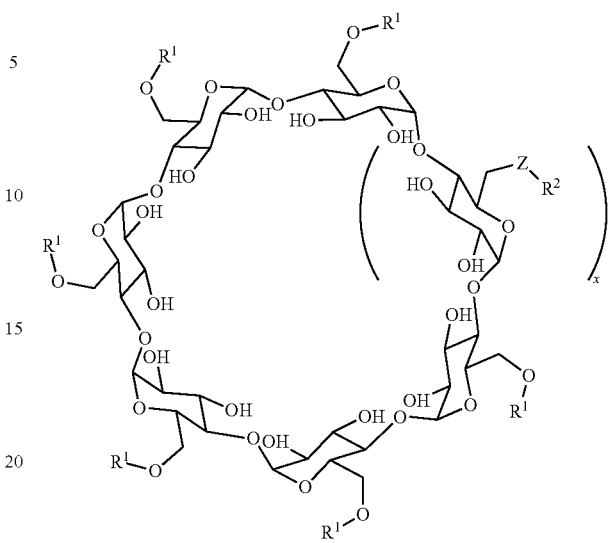

wherein:
x is an integer from 0 to 8; Z is O or NH;
each $R^1$ and $R^2$ is, independently, hydrogen, a substituted or unsubstituted $(C_1-C_6)$hydrocarbyl group or a group of the formula (IIIc):

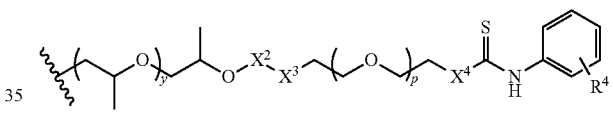

wherein y is an integer from 0 to 10; p is an integer from 1 to 10; $X^2$ represents $(C_1-C_6)$acyl, a short-chain polypeptide, a short-chain carbohydrate, a polyester or a polyamide; $X^3$ and $X^4$ are each, independently, —O—, —NH—, a carbamyl group, a heterocyclyl group, a disulfide (—S—S—), amide or ester; and $R^4$ is a reporter group, with the proviso that at least one $R^2$ group is a group of the formula (IIIc).

Embodiment 2 relates to the polyrotaxane of Embodiment 1, wherein C and C' are the same or different and represent end capping groups of the formula:

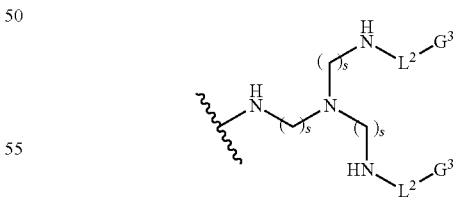

wherein each $L^2$ is independently a $(C_1-C_6)$acyl.

Embodiment 3 relates to the polyrotaxane of Embodiments 1-2 wherein $L^2$ is C=O.

Embodiment 4 relates to the polyrotaxane of Embodiments 1-3, wherein each s is 2.

Embodiment 5 relates to the polyrotaxane of Embodiments 1-4, wherein each $G^3$ is, independently, a cholesteryl group, a 2,4,6-trinitro phenyl group, a cyclodextrin radical or a fluorescein radical.

Embodiment 6 relates to the polyrotaxane of Embodiments 1-5, wherein B represents:

[structure: —O—CH₂CH₂—(O—)_d—O—(CHR⁵—CH₂—O—)_q—]

to which the endcapping groups are covalently attached to B via a carbamyl group, a heterocyclyl group, a disulfide (—S—S—), amide or ester.

Embodiment 7 relates to the polyrotaxane of Embodiments 1-6, wherein $R^1$ is a substituted ($C_1$-$C_6$)hydrocarbyl group and $R^2$ is a group of the formula (IIIc).

Embodiment 8 relates to the polyrotaxane of Embodiments 1-7, wherein x is 1 and Z is O.

Embodiment 9 relates to the polyrotaxane of Embodiments 1-8, wherein $X^2$ represents ($C_1$-$C_6$)acyl.

Embodiment 10 relates to the polyrotaxane of Embodiments 1-9, wherein $X^2$ is C=O.

Embodiment 11 relates to the polyrotaxane of Embodiments 1-10, wherein $X^3$ and $X^4$ are each NH.

Embodiment 12 relates to the polyrotaxane of Embodiments 1-11, wherein m+m'+n+n' is from about 5 to about 20.

Embodiment 13 relates to the polyrotaxane of Embodiments 1-12, wherein A is hydroxypropyl-β-cyclodextrin (HPβCD).

Embodiment 14 relates to the polyrotaxane of Embodiments 1-13, wherein A' is 4-sulfobutylether-β-cyclodextrin (SBEβCD).

Embodiment 15 relates to the polyrotaxane of Embodiments 1-14, wherein A is hydroxypropyl-β-cyclodextrin and m+n is from about 2 to about 10; and A' is 4-sulfobutylether-β-cyclodextrin and m'+n' is from about 2 to about 10.

Embodiment 16 relates to the polyrotaxane of Embodiments 1-15, wherein the reporter group is a chelating moiety.

Embodiment 17 relates to the polyrotaxane of Embodiment 16, wherein the chelating moiety is a radionuclide chelating moiety comprising a radionuclide.

Embodiment 18 relates to the polyrotaxane of Embodiment 17, wherein the radionuclide chelating moiety is a paramagnetic nuclide chelating moiety comprising a paramagnetic nuclide.

Embodiment 19 relates to the polyrotaxane of Embodiment 18, wherein the chelating moiety is a DOTA radical or a DO3A radical.

Embodiment 20 relates to the polyrotaxane of Embodiment 1, wherein the polyrotaxane is HPβCD/SBEβCD-F127 (wherein d=200 and q=65); HPβCD/SBEβCD-F68 (wherein d=151 and q=29); HPβCD/SBEβCD-L35 (wherein d=22 and q=16); HPβCD/SBEβCD-L64 (wherein d=26 and q=30); or HPβCD/SBEβCD-L81 (wherein d=6.25 and q=43), wherein:

the polyrotaxane has a weight average molecular weight of about 20,000 g/mol to about 50,000 g/mol as determined by GPC analysis;

HPβCD is a macrocyclic host of the formula (I) wherein each $R^1$ is H, Z is O, and $R^2$ is a group of the formula (IIIc), wherein y is 0; $X^2$ is C(O)O; $X^3$ and $X^4$ are each —NH—; p is 2; and $R^4$ is DOTA; and the groups C and C' of the formula:

[structure showing endcap with NH, N, L², G³ groups]

wherein each s is 2; each $L^2$C(O); and each $G^3$ represents a cholesteryl group, is covalently attached to the group B of the formula:

[structure: —O—CH₂CH₂—(O—)_d—O—(CHR⁵—CH₂—O—)_q—]

wherein the variables d and q are defined as above, for each polyrotaxane, via a C(O) group.

Embodiment 21 relates to the polyrotaxane of Embodiment 20, wherein the polyrotaxne comprises from about 1 to about 10 HPβCD molecules and from about 1 to about 10 SBEβCD.

Embodiment 22 relates to a pharmaceutical composition comprising the polyrotaxane of Embodiments 1-21 and a pharmaceutically acceptable carrier.

Embodiment 23 relates to a method for treating Niemann-Pick type C (NPC) comprising administering a therapeutically effective amount of a polyrotaxane as in Embodiments 1-21 or a pharmaceutical composition of Embodiment 22 to a subject in need thereof.

Embodiment 24 relates to a method for imaging comprising administering an amount sufficient for imaging of a polyrotaxane as in Embodiments 1-21 or a pharmaceutical composition of Embodiment 22 to a subject in need thereof.

What is claimed is:

1. A polyrotaxane having the general formula:

[structure: C—B—(A)_n—(A)_m—(A')_{n'}—(A')_{m'}—C']

or salts thereof,
wherein:
each m, m', n and n is, independently, an integer from 0 to 30, with the proviso that m+m'+n+n' is from about 4 to about 30;
C and C' are the same or different and represent end capping groups of the formula:

[structure showing endcap with NH, N, (L²-G³)_s groups]

wherein each $L^2$ is independently a bond or $(C_1-C_6)$acyl; each $G^3$ is a steroid group; and each s is independently an integer from 1 to 6;

B represents:

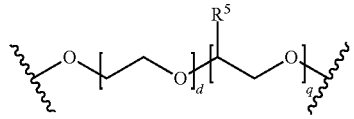

to which the endcapping groups are covalently attached to B via a $(C_1-C_6)$hydrocarbylene group;

wherein $R^5$ is methyl; d is an integer from about 1 to about 800; and q is an integer from about 6 to about 800; and A and A' each independently represent the macrocyclic host molecule of the general formula (I):

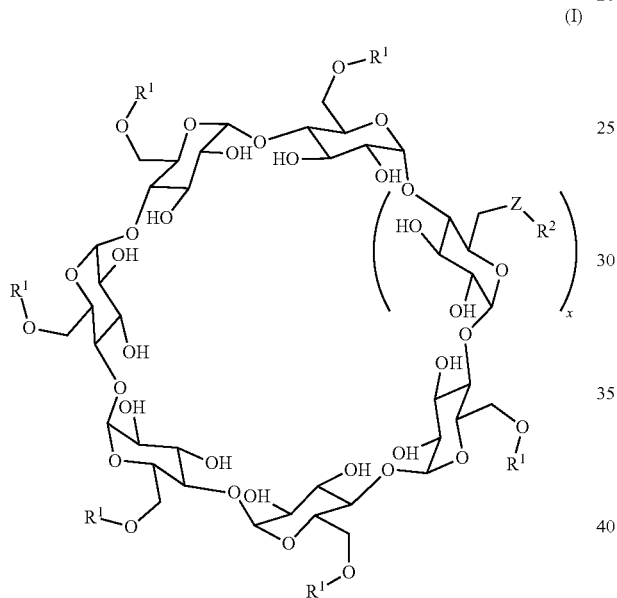

wherein:

A and A' can be the same or different;

x is an integer from 0 to 8; Z is O or NH;

each $R^1$ and $R^2$ is, independently, hydrogen or a substituted or unsubstituted $(C_1-C_6)$hydrocarbyl group.

2. The polyrotaxane of claim 1, wherein C and C' are the same or different and represent end capping groups of the formula:

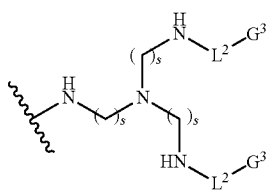

wherein each $L^2$ is independently a $(C_1-C_6)$acyl.

3. The polyrotaxane of claim 1, wherein $R^1$ is a substituted $(C_1-C_6)$hydrocarbyl group.

4. The polyrotaxane of claim 1, wherein m+m'+n+n' is from about 5 to about 20.

5. The polyrotaxane of claim 1, wherein A is hydroxypropyl-β-cyclodextrin (HPβCD).

6. The polyrotaxane of claim 1, wherein A' is 4-sulfobutylether-β-cyclodextrin (SBEβCD).

7. The polyrotaxane of claim 1, wherein A is hydroxypropyl-β-cyclodextrin and m+n is from about 2 to about 10; and A' is 4-sulfobutylether-β-cyclodextrin and m'+n' is from about 2 to about 10.

8. The polyrotaxane of claim 1, wherein the polyrotaxane is HPβCD/SBEβCD-F127 (wherein d=200 and q=65); HPβCD/SBEβCD-F68 (wherein d=151 and q=29); HPβCD/SBEβCD-L35 (wherein d=22 and q=16); HPβCD/SBEβCD-L64 (wherein d=26 and q=30); or HPβCD/SBEβCD-L81 (wherein d=6.25 and q=43), wherein:

the polyrotaxane has a weight average molecular weight of about 20,000 g/mol to about 50,000 g/mol as determined by GPC analysis;

HPβCD is a macrocyclic host of the formula (I) wherein each R' is H, and Z is O; and the groups C and C' of the formula:

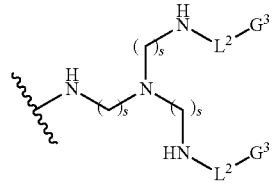

wherein each s is 2; each $L^2$ is C(O); and the steroid group is a cholesteryl group that is covalently attached to the group B of the formula:

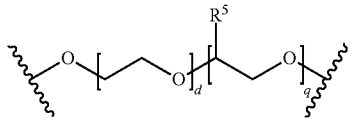

via a C(O) group.

9. The polyrotaxane of claim 8, wherein the polyrotaxne comprises from about 1 to about 10 HPβCD molecules and from about 1 to about 10 SBEβCD.

10. A pharmaceutical composition comprising the polyrotaxane of claim 1 and a pharmaceutically acceptable carrier.

11. A method for treating Niemann-Pick type C (NPC) comprising administering a therapeutically effective amount of a polyrotaxane as in claim 1 to a subject in need thereof.

12. The polyrotaxane of claim 1, wherein the steroid group is a cholesteryl group.

* * * * *

UNITED STATES PATENT AND TRADEMARK OFFICE
CERTIFICATE OF CORRECTION

| | | |
|---|---|---|
| PATENT NO. | : 11,434,330 B2 | Page 1 of 1 |
| APPLICATION NO. | : 15/768365 | |
| DATED | : September 6, 2022 | |
| INVENTOR(S) | : Thompson et al. | |

It is certified that error appears in the above-identified patent and that said Letters Patent is hereby corrected as shown below:

In the Claims

In Column 74, Line 52, in Claim 1, delete "n and n" and insert --n and n'-- therefor In Column 76, Line 26, in Claim 8, delete "R'" and insert --$R^1$-- therefor Signed and Sealed this
Twentieth Day of June, 2023

Katherine Kelly Vidal
*Director of the United States Patent and Trademark Office*